US012174191B2

(12) United States Patent
Haab et al.

(10) Patent No.: US 12,174,191 B2
(45) Date of Patent: Dec. 24, 2024

(54) METHODS FOR DETECTING AND FOR TREATING PANCREATIC CANCER

(71) Applicants: Van Andel Research Institute, Grand Rapids, MI (US); University of Pittsburgh-Of The Commonwealth System of Higher Education, Pittsburgh, PA (US)

(72) Inventors: Brian B. Haab, Jenison, MI (US); Randall E. Brand, Sewickley, PA (US)

(73) Assignees: VAN ANDEL RESEARCH INSTITUTE, Grand Rapids, MI (US); UNIVERSITY OF PITTSBURGH, Pittsburgh, PA (US)

( * ) Notice: Subject to any disclaimer, the term of this patent is extended or adjusted under 35 U.S.C. 154(b) by 788 days.

(21) Appl. No.: 16/928,293

(22) Filed: Jul. 14, 2020

(65) Prior Publication Data
US 2020/0340996 A1 Oct. 29, 2020

Related U.S. Application Data

(62) Division of application No. 15/216,768, filed on Jul. 22, 2016, now Pat. No. 10,753,936.

(51) Int. Cl.
*G01N 33/574* (2006.01)
(52) U.S. Cl.
CPC ............ *G01N 33/57438* (2013.01); *C12Y 204/01065* (2013.01); *G01N 2333/4725* (2013.01); *G01N 2333/91102* (2013.01); *G01N 2440/38* (2013.01)
(58) Field of Classification Search
CPC ..... G01N 33/57438; G01N 2333/4725; G01N 2333/91102; G01N 2440/38; C12Y 204/01065
See application file for complete search history.

(56) References Cited

U.S. PATENT DOCUMENTS

| | | | |
|---|---|---|---|
| 4,389,392 A | 6/1983 | Adachi | |
| 5,329,028 A | 7/1994 | Ashkenazi et al. | |
| 6,440,661 B1 | 8/2002 | Ogreid et al. | |
| 6,828,146 B2 | 12/2004 | Desnoyers et al. | |
| 7,183,118 B2 | 2/2007 | Aebersold et al. | |
| 7,547,424 B2 | 6/2009 | Haab et al. | |
| 9,309,317 B2 | 4/2016 | Umana | |
| 2002/0137104 A1 | 9/2002 | Cosma | |
| 2002/0164824 A1 | 11/2002 | Xiao et al. | |
| 2003/0153014 A1 | 8/2003 | Shen et al. | |
| 2004/0023306 A1 | 2/2004 | Aebersold et al. | |
| 2004/0063624 A1 | 4/2004 | Kage et al. | |
| 2004/0217283 A1 | 11/2004 | Bai | |
| 2005/0095611 A1 | 5/2005 | Chan et al. | |
| 2006/0263825 A1 | 11/2006 | Denny et al. | |
| 2007/0059769 A1 | 3/2007 | Blixt | |
| 2007/0059783 A1 | 3/2007 | Packer et al. | |
| 2007/0178538 A1 | 8/2007 | Haab | |
| 2009/0099036 A1 | 4/2009 | Lubman | |
| 2009/0118641 A1 | 5/2009 | Van Dam et al. | |
| 2011/0143373 A1 | 6/2011 | Hirvonen et al. | |
| 2011/0257029 A1 | 10/2011 | Haab et al. | |
| 2012/0329878 A1 | 12/2012 | Coussens et al. | |
| 2013/0005598 A1 | 1/2013 | Haab | |
| 2013/0189268 A1 | 7/2013 | Du et al. | |
| 2014/0274768 A1 | 9/2014 | Haab | |
| 2015/0099669 A1 | 4/2015 | Zhang | |

FOREIGN PATENT DOCUMENTS

| | | | |
|---|---|---|---|
| JP | 200515439 A | 6/2005 | |
| JP | 2006521567 A | 9/2006 | |
| JP | 2008541060 A | 11/2008 | |
| JP | 2009142238 A | 7/2009 | |
| WO | WO0237106 A2 | 5/2002 | |
| WO | WO03060522 A1 | 7/2003 | |
| WO | WO03087821 A2 | 10/2003 | |
| WO | WO06113245 A2 | 10/2006 | |
| WO | WO09092108 A2 | 7/2009 | |
| WO | WO11082321 A1 | 7/2011 | |
| WO | 2016036705 A | 3/2016 | |

OTHER PUBLICATIONS

Tang et al. (Cellular and Molecular Gastroenterology and Hepatology 2(2): 210-221 and 221.e1-221.e15, Mar. 2016).*
U.S. Appl. No. 11/375,756, filed Mar. 15, 2006, U.S. Pat. No. 7,838,634, Issued.
U.S. Appl. No. 12/951,718, filed Nov. 22, 2010, U.S. Pat. No. 8,632,983, Issued.
U.S. Appl. No. 13/519,766, filed Sep. 10, 2012, Abandoned.
U.S. Appl. No. 14/203,049, filed Mar. 10, 2014, Abandoned.
U.S. Appl. No. 15/216,768, filed Jul. 22, 2016, U.S. Pat. No. 10,753,936, Issued.
U.S. Appl. No. 17/059,660, filed Nov. 30, 2020, Published.
Aljebreen, A.M., et al. "Utility of endoscopic ultrasound, cytology and fluid carcinoembryonic antigen and CA 19-9 levels in pancreatic cystic lesions." World J Gastroenterol. Aug. 7, 2007;13(29):3962-6.
Andrews, P.W., et al. Three monoclonal antibodies defining distinct differentiation antigens associated with different high molecular weight polypeptides on the surface of human embryonal carcinoma cells. Hybridoma 1984;3:347-361.

(Continued)

*Primary Examiner* — Alana Harris Dent
(74) *Attorney, Agent, or Firm* — Honigman LLP; Douglas H. Siegel; Jonathan P. O'Brien

(57) ABSTRACT

A method of diagnosing pancreatic cancer in a patient by detecting a level of one or more glycoforms of a Lewis antigen and a level of the one or more glycoforms of MUC5AC. The patient diagnosed with pancreatic cancer then may be treated for this disease. Also, a method for detecting a level of a glycan in a sample which includes using a capture reagent to immobilize the glycan on a substrate; exposing the immobilized glycan to a detection reagent; detecting the level of the immobilized glycan; and combining the biological sample with one or more pre-capture enzymes and/or exposing the immobilized glycan to one or more pre-detection enzymes.

19 Claims, 21 Drawing Sheets

(56) References Cited

OTHER PUBLICATIONS

Babu, P., et al. "Structural characterisation of neutrophil glycans by ultra-sensitive mass spectrometric glycomics methodology." Glycoconjugate journal. Nov. 2009;26(8):975-86.

Balmana, M., et al. Identification of potential pancreatic cancer serum markers: increased sialyl-Lewis X on ceruloplasmin. Clin Chim Acta 2015; 442C:56-62.

Barone, A., et al. Sialyl-lactotetra, a novel cell surface marker of undifferentiated human pluripo-tent stem cells. J Biol Chem 2014;289:18846-18859.

Basturk, O., et al. "Pancreatic cysts: pathologic classification, differential diagnosis, and clinical implications." Arch Pathol Lab Med. Mar. 2009;133(3):423-38.

Bhattacharyya, S. et al. "Diagnosis of Pancreatic Cancer Using Serum Proteomic Profiling," Neoplasia, vol. 6(No. 5), p. 674-686, (2004).

Blixt, O. et al. "Printed covalent glycan array for ligand profiling of diverse glycan binding proteins," Proc Natl Acad Sci USA 101, pp. 17033-17038 (2004).

Brody, J.R., et al. Adenosquamous carcinoma of the pancreas harbors KRAS2, DPC4 and TP53 molecular alterations similar to pancreatic ductal adenocarcinoma. Mod Pathol 2009;22: 651-659.

Brugge, WR, et al. "Diagnosis of pancreatic cystic neoplasms: a report of the cooperative pancreatic cyst study." Gastroenterology. May 2004; 126(5): pp. 1330-1336.

US Biological Technical Data for CA125 Cancer Antigen (Mucin 16, MUC16, MUC-16, CA125, CA-125, Cancer Antigen 125, FLJ14303, Mucin 16 Cell Surface Associated, Cancer-related Tumor Marker CA125, Ovarian Carcinoma Antigen CA125); printed from www.usbio.net/technicalsheet.php?item=C0050-01D (publication date unknown), printed Feb. 25, 2022.

Cao, Z., et al., "Specific Glycoforms of MUC5AC and Endorepellin Accurately Distinguish Mucinous from Nonmucinous Pancreatic Cysts." Research, Molecular & Cellular Proteomics 12.10 (Jul. 9, 2013), pp. 2724-2734.

Chang, J.W., et al. "Identification of circulating endorepellin LG3 fragment: Potential use as a serological biomarker for breast cancer." Proteomics Clin Appl. Jan. 2008;2(1): pp. 23-32.

Chari, S.T., et al. Early detection of sporadic pancreatic cancer: summative review. Pancreas 2015;44:693-712.

Chen, M., et al. "Molecular pathology of pancreatic neuroendocrine tumors." J Gastrointest Oncol. Mar. 27, 2012; 3(3): pp. 182-188.

Chen, R., et al. "Glycoproteomics analysis of human liver tissue by combination of multiple enzyme digestion and hydrazide chemistry." Journal of proteome research. Feb. 2009;8(2): pp. 651-661.

Chen, S. et al. "Antibody-lectin microarrays reveal altered glycosylation on secreted proteins in pancreatic cancer patients." Proceeding of the Annual Association for Cancer Research 47: pp. 337-338 (Apr. 2006).

Chen, S., et al. "Multiplexed analysis of glycan variation on native proteins captured by antibody microarrays." Nature methods. May 2007;4(5): pp. 437-444.

Cizginer, S., et al. "Cyst fluid carcinoembryonic antigen is an accurate diagnostic marker of pancreatic mucinous cysts." Pancreas. Oct. 2011;40(7): pp. 1024-1028.

Cote, G.A., et al. A pilot study to develop a diagnostic test for pancreatic ductal adeno-carcinoma based on differential expression of select miRNA in plasma and bile. Am J Gastroenterol 2014; 109:1942-1952.

Cuoghi, A., et al. "Role of proteomics to differentiate between benign and potentially malignant pancreatic cysts." J Proteome Res. Mar. 23, 2011;10(5): pp. 2664-2670.

Dennis, J.W., "Glycoprotein glycosylation and cancer progression." Biochimica et biophysica acta. Dec. 6, 1999;1473(1): pp. 21-34.

Fallon, B.P., et al. The marker state space (MSS) method for classifying clinical samples. PLoS One 2013;8:e65905.

Fredman, P., et al. Sialyllactotetraosylceramide, a ganglioside marker for human malignant gliomas. J Neurochem 1988;50:912-919.

Fukuda, M.N., et al. Structures of glycosphingolipids isolated from human embryonal carcinoma cells. The presence of mono- and disialosyl glycolipids with blood group type 1 sequence. J Biol Chem 1986;261:5145-515.

Galustian, C., et al. Sialyl-Lewis(x) sequence 6-0-sulfated at N-acetylglucosamine rather than at galactose is the preferred ligand for L-selectin and de-N-acetylation of the sialic acid enhances the binding strength. Biochem Biophys Res Conunun 1997;240:748-751.

Garud, S.S., et al. "Molecular analysis of cyst fluid aspiration in the diagnosis and risk assessment of cystic lesions of the pancreas." Clin Transl Sci. Dec. 8, 2011; 5(1): pp. 102-107.

Gbormittah, F.O., et al. "Characterization of glycoproteins in pancreatic cyst fluid using a high-performance multiple lectin affinity chromatography platform." J. Proteome Res. Jan. 3, 2013, vol. 1, pp. 289-299.

Gentiloni, N., et al. Pancreatic juice 90K and serum CA 19-9 combined determination can discriminate between pancreatic cancer and chronic pancreatitis. Am J Gastroenterol 1995;90:1069-1072.

Goonetilleke, K.S., et al. Systematic review of carbohydrate antigen (CA 19-9) as a biochemical marker in the diagnosis of pancreatic cancer, Eur J Surg Oncol, 33 (2007), pp. 266-270.

Haab, B. et al. "839.4 Antibody microarray analysis of blood serum from cancer patients," Experimental Biology 2003: Meeting Abstracts, FASEB Journal, p. 1, (Apr. 4, 2003).

Haab, B. et al. "Protein microarrays for highly parallel detection and quantification of specific proteins and antibodies in complex solutions," Genome Biol 264, pp. 33-45 (2004).

Haab, B.B., et al. "Glycosylation Variants of Mucins and CEACAMs as Candidate Biomarkers for the Diagnosis of Pancreatic Cystic Neoplasms." Annals of surgery. [Research]. May 2010; 251(5):937-45.

Haab, B.B., et al. "Glycosylation Variants on Mucins as Candidate Markers for the Diagnosis of Pancreatic Cystic Neoplasms." Abstract from Pancreas, 2008, 37(4), pp. 472-473.

Haab, B.B., et al. "Glycosylation Variants on Mucins as Candidate Markers for the Diagnosis of Pancreatic Cystic Neoplasms." Presentation at the 39th Annual Meeting of the American Pancreatic Association, Nov. 7-8, 2008, Chicago, IL.

Haab, B.B.. "Antibody-lectin sandwich arrays for biomarker and glycobiology studies." Expert review of proteomics. Feb. 2010;7(1): pp. 9-11.

Haab, B.B., et al. Definitive characterization of CA 19-9 in resectable pancreatic cancer using a reference set of serum and plasma specimens. PLoS One 2015;10:e0139049.

Haab, B.B., et al. High-throughput studies of protein glycoforms using antibody-lectin sandwich arrays. Methods Mol Biol 2011;785:223-236.

Haab, B.B. "Using lectins in biomarker research: Addressing the limitations of sensitivity and availability." Proteomics Clin Appl. Aug. 2012, vol. 6(7-8):346-50.

Haab, B. et al. "RCA-Enhanced Protein Detection Arrays," Methods in Molecular Biology 328: 15-29 (2006).

Haglund, C. "Tumour marker antigen CA125 in pancreatic cancer: A comparison with CA19-9 and CEA", Br. J. Cancer, 1986, 54, pp. 897-901.

Haglund, C., et al. Gastrointestinal cancer-associated antigen CA 19-9 in histological specimens of pancreatic tumours and pancreatitis, Br J Cancer, 53 (1986), pp. 189-195.

Hamelinck, D. et al. "Optimized Normalization for Antibody Microarrays and Application to Serum-Protein Profiling," Molecular & Cellular Proteomics 4.6, The American Society for Biochemistry and Molecular Biology, pp. 773-784 (Mar. 25, 2005).

Hammel, P.R., et al. "Detection of gastric mucins (M1 antigens) in cyst fluid for the diagnosis of cystic lesions of the pancreas." International journal of cancer. Jun. 20, 1997;74(3): pp. 286-290.

Hasehira, K., et al. "Structural and quantitative evidence for dynamic glycome shift on production of induced pluripotent stem cells." Molecular & cellular proteomics : MCP. Sept. 4, 2012; 11(12): pp. 1913-1923.

Hasnain, S.Z., et al. "Muc5ac: a critical component mediating the rejection of enteric nematodes." J Exp Med. May 9, 2011; 208(5): pp. 893-900.

(56) References Cited

OTHER PUBLICATIONS

Herlyn, M., et al. Colorectal carcinoma-specific antigen: detection by means of monoclonal antibodies, Proc Natl Acad Sci U S A, 76 (1979), pp. 1438-1442.
Ho, J. et al. "Association of Sialyl-Lewisa and Sialyl-Lewisx with MUC-1 Apomucin in a Pancreatic Cancer Cell Line," Cancer Research 55: pp. 3659-3663, (Aug. 15, 1995).
Hollingsworth, M. et al. "Mucins in Cancer: Protection and Control of the Cell Surface," Cancer 4: pp. 45-60 (Jan. 2004).
Hoshi, H., et al. "Tumor-associated MUC5AC stimulates in vivo tumorigenicity of human pancreatic cancer." Int J Oncol. 38(3): pp. 619-627 (2011).
Iacobuzio-Donahue, C.A., et al. "Genetic Basis of Pancreas Cancer Development and Progression: Insights from Whole-Exome and Whole-Genome Sequencing." American Association for Cancer Research (Aug. 21, 2012) DOI:10.1158/1078-0432.CCR-12-0315; pp. 4257-4265.
Inaguma, S., et al. "GLI1 facilitates the migration and invasion of pancreatic cancer cells through MUC5AC-mediated attenuation of E-cadherin." Oncogene [Research Support, Non-U.S. Gov't]. Feb. 10, 2011;30(6): pp. 714-723.
Irimura,T., et al. "Diverse glycosylation of MUC1 and MUC2: potential significance in tumor immunity." Journal of biochemistry. Dec. 1999;126(6): pp. 975-985.
Iwai, K., et al. Importance of E-selectin (ELAM-1) and sialyl Lewis(a) in the adhesion of pancreatic carcinoma cells to activated endothelium. Int J Cancer 1993;54:972-977.
Jung, Y. et al., "Recent advances in immobilation methods of antibodies on solid supports" Analyst, 2008, 133: pp. 697-701.
Kalthoff, H. et al. "Characterization of CA 19-9 Bearing Mucins as Physiological Exocrine Pancreatic Secretion Products," Cancer Research 46: pp. 3605-3607 (Jul. 1986).
Kato, S., et al. "MUC5AC mucin gene regulation in pancreatic cancer cells." Int J Oncol. Jul. 2006;29(1): pp. 33-40.
Kawa, S. et al. "Preparation of Pancreatic Cancer-Associated Mucin Expressing CA19-9, CA50, Span-1, Sialyl SSEA-1, and Dupan-2." Scand J Gastroenterol, 1991, 26: pp. 981-992.
Kawa, S., et al. Epitope analysis of SPan-1 and DUPAN-2 using synthesized glyco-conjugates sialyllact-N-fucopentaose II and sialyllact-N-tetraose. Pancreas 1994;9:692-697.
Keusch, J. et al. "Analysis of different glycosylation states in IgG subclasses." Clinica Chimica Acta 252: pp. 147-157 (1996).
Khalid, A., et al. "Pancreatic cyst fluid DNA analysis in evaluating pancreatic cysts: a report of the PANDA study." Gastrointestinal endoscopy. May 2009;69(6): pp. 1095-1102.
Khalid, A., et al. "The role of pancreatic cyst fluid molecular analysis in predicting cyst pathology." Clin Gastroenterol Hepatol. Oct. 2005;3(10): pp. 967-973.
Kletter, D., et al. Determining lectin specificity from glycan array data using motif segregation and GlycoSearch software. Curr. Protoc. Chem. Biol. Jun. 2013; 5(2):157-169.
Knezevic, A., et al. "Variability, heritability and environmental determinants of human plasma N-glycome." Journal of proteome research. Feb. 2009;8(2): pp. 694-701.
Kobayashi, M., et al. "Roles of gastric mucin-type O-glycans in the pathogenesis of Helicobacter pylori infection." Glycobiology. May 2009;19(5): pp. 453-461.
Kopf, E., et al. "Antibody arrays—An Emerging Tool in Cancer Proteomics." The International Journal of Biochemistry & Cell Biology 39 (2007) pp. 1305-1317.
Kopf, E., et al. "Panorama Ab Microarray Cell Signaling kit: A unique tool for protein expression analysis." Proteomics 2005, 5, pp. 2412-2416.
Kunkle, J.P., et al. "Comparisons of the Glycosylation of a Monoclonal Antibody Produced under Nominally Identical Cell Culture Conditions in Two Different Bioreactors." Biotechnol. Prog. 2000, 16, pp. 462-470.
Kuno, A. et al. "Evanescent-field fluorescence-assisted lectin microarray: a new strategy for glycan profiling," Nat Methods 2, pp. 851-856 (2005).
Lau, K.S., et al. "N-Glycans in cancer progression." Glycobiology. Oct. 2008;18(10): pp. 50-60.
Lee, K.S., et al. "Prevalence of incidental pancreatic cysts in the adult population on MR imaging." Am J Gastroenterol. Sep. 2010;105(9): pp. 2079-2084.
Lin, Z., et al. "Mass spectrometric assay for analysis of haptoglobin fucosylation in pancreatic cancer." J Proteome Res. 2011; 10(5):2602-11.
MacDonald, F., et al. "Expression of CA125 in pancreatic carcinoma and chronic pancreatitis", Br. J Cancer, 1998, 58, pp. 505-506.
Magnani, J et al. "Identification of the Gastrointestinal and Pancreatic Cancer-associated Antigen Detected by Monoclonal Antibody 19-9 in the Sera of Patients as a Mucin," Cancer Research 43: 5489-5492 (Nov. 1983).
Magnani, J.L., et al. A monoclonal antibody-defined antigen associated with gastrointestinal cancer is a ganglioside containing sialylated lacto-N-fucopentaose II, J Biol Chem, 257 (1982), pp. 14365-14369.
Magnani, J.L., et al. A monosialoganglioside is a monoclonal antibody-defined antigen of colon carcinoma, Science, 212 (1981), pp. 55-56.
Maker, A.V., et al. "Cyst fluid interleukin-1beta (IL1beta) levels predict the risk of carcinoma in intraductal papillary mucinous neoplasms of the pancreas." Clin Cancer Res. Mar. 15, 2011;17(6):1502-8.
Maker, A.V., et al. "Pancreatic Cyst Fluid and Serum Mucin Levels Predict Dysplasia in Intraductal Papillary Mucinous Neoplasms of the Pancreas." Ann Surg Oncol. (2011) 18: pp. 199-206.
Mann, B.F., et al. "Glycomic and proteomic profiling of pancreatic cyst fluids identifies hyperfucosylated lactosamines on the N-linked glycans of overexpressed glycoproteins." Mol Cell Proteomics. Mar. 5, 2012 11(7):M111 015792.
Masaki, et al. "Sialylated MUC1 Mucin Expression in Normal Pancreas, Benign Pancreatic Lesions, and Pancreatic Ductal Adenocarcinoma." Hepato-Gastroenterology, 1999, 46, pp. 2240-2245.
Matthaei, H., et al. "Cystic precursors to invasive pancreatic cancer." Nat Rev Gastroenterol Hepatol. Mar. 2011;8(3): pp. 141-150.
Mazur, P.K., et al. Notch2 is required for progression of pancreatic intraepithelial neoplasia and development of pancreatic ductal adenocarcinoma. Proc Natl Acad Sci U S A 2010;107:13438-13443.
McEver, R.P. Selectin-carbohydrate interactions during inflammation and metastasis. Glycoconj J 1997;14: 585-591.
Melo, S.A., et al. Glypican-1 identifies cancer exosomes and detects early pancreatic cancer. Nature 2015;523:177-182.
Metzgar, R.S., et al. Antigens of human pancreatic adenocarcinoma cells defined by murine monoclonal antibodies. Cancer Res 1982; 42:601-608.
Miller, J. et al. "Antibody microarray profiling of human prostate cancer sera: Antibody screening and identification of potential biomarkers." Proteomics, Wiley-VCH Verlag GmbH & Co., KGaA, Weinheim, pp. 56-63 (2003).
Mitsuoka, C., et al. Identification of a major carbohydrate capping group of the L-selectin ligand on high endothelial venules in human lymph nodes as 6-sulfo sialyl Lewis X. J Biol Chem 1998;273:11225-11233.
Miyoshi, E., et al. "Fucosylated haptoglobin is a novel marker for pancreatic cancer: detailed analyses of oligosaccharide structures." Proteomics Aug. 2008;8(16): pp. 3257-3262.
Mongiat, M., et al. "Endorepellin, a novel inhibitor of angiogenesis derived from the C terminus of perlecan." The Journal of biological chemistry, Feb. 7, 2003;278(6): pp. 4238-4249.
Morris, J.P., et al. Beta-catenin blocks Kras-dependent reprogramming of acini into pancreatic cancer precursor lesions in mice. J Clin Invest 2010; 120:508-520.
Natunen, S., et al. The binding specificity of the marker antibodies Tra-1-60 and Tra-1-81 reveals a novel pluripotency-associated type 1 lactosamine epitope. Glycobiology 2011;21:1125-1130.
Nishihara, S., et al. Alpha (1,3/1,4)fucosyltransferase (FucT-III) gene is inactivated by a single amino acid substitution in Lewis histo-blood type negative individuals, Biochem Biophys Res Commun, 196 (1993), pp. 624-631.

(56) References Cited

OTHER PUBLICATIONS

Ohyama, C., et al. Dual roles of sialyl Lewis X oligosaccharides in tumor metastasis and rejection by natural killer cells. EMBO J 1999;18:1516-1525.
Okuyama, N., et al. "Fucosylated haptoglobin is a novel marker for pancreatic cancer: A detailed analysis of the oligosaccharide structure and a possible mechanism for fucosylation." International journal of cancer, Dec. 29, 2006;118(11): pp. 2803-2808.
Orchekowski, R.P., et al. "Antibody microarray profiling reveals individual and combined serum proteins associated with pancreatic cancer." Cancer Research 2005; 65:(23) pp. 11193-11202.
Parekh, R.B., et al. "Association of rheumatoid arthritis and primary osteoarthritis with changes in the glycosylation pattern of total serum IgG." Nature. Aug. 1-7, 1985;316(6027): pp. 452-457.
Parker, N., et al., "A new enzyme-linked lectin/mucin antibody sandwich assay (CAM 17.1/WGA) assessed in combination with CA 19-9 and peanut lectin binding assay for the diagnosis of pancreatic cancer." Cancer, 1992, 70(5): pp. 1062-1068.
Partyka, K., et al. "Comparison of surgical and endoscopic sample collection for pancreatic cyst fluid biomarker identification." Journal of proteome research. [Research Support, N.I.H., Extramural Research Support, Non-U.S. Gov't]. May 4, 2012;11(5): pp. 2904-2911.
Partyka, K., et al. Diverse monoclonal antibodies against the CA 19-9 antigen show variation in binding specificity with consequences for clinical interpretation. Proteomics 2012;12:2212-2220.
PCT/US2006013557, European Search Report, May 9, 2008.
PCT/US2006013557, ISR, Jan. 24, 2007 (WO2006113245).
PCT/US2010062534, ISR, Mar. 23, 2011.
Porter, A., et al. "A motif-based analysis of glycan array data to determine the specificities of glycan-binding proteins." Glycobiology. 2010 Mar. 2010;20(3): pp. 369-380.
Pour, P.M., et al. Expression of blood group-related antigens ABH, Lewis A, Lewis B, Lewis X, Lewis Y, and CA 19-9 in pancreatic cancer cells in comparison with the patient's blood group type, Cancer Res, 48 (1988), pp. 5422-5426.
Räty, S., et al. "Cyst fluid tumor-associated trypsin inhibitor may be helpful in the differentiation of cystic pancreatic lesions." J Gastrointest Surg. Jul.-Aug. 2004;8(5): pp. 569-574.
Rausch, P., et al. "Colonic mucosa-associated microbiota is influenced by an interaction of Crohn disease and FUT2 (Secretor) genotype." Proceedings of the National Academy of Sciences of the United States of America. Nov. 22, 2011;108(47): pp. 19030-19035.
Rhim, A.D., et al. EMT and dissemination precede pancreatic tumor formation. Cell 2012; 148:349-361.
Ringel, J., et al. "The MUC gene family: Their role in diagnosis and early detection of pancreatic cancer." Molecular Cancer, 2003, 2:1-5.
Rosenfeld, R et al. "U-c Fingerprint: Glycoprotein Analysis Based on a Lectin Array." Glycobiology 13 (No. 11): 845 (Nov. 2003).
Routh, V., et al., "A novel technique for producing antibody-coated microprobes using a thiol-terminal silane and a heterobifunctional crosslinker." J. Neuroscience Methods, 1997, 71: pp. 163-168.
Ryu, J.K., et al. "Elevated microRNA miR-21 Levels in Pancreatic Cyst Fluid Are Predictive of Mucinous Precursor Lesions of Ductal Adenocarcinoma." Pancreatology. Jul. 12, 2011;11(3): pp. 343-350.
Santos-Silva, F. et al. "Thomsen-Friedenreich antigen expression in gastric carcinomas is associated with MUC1 mucin VNTR polymorphism." Glycobiology 15 (No. 5): pp. 511-517 (2005).
Satomaa, T., et al. "Analysis of the human cancer glycome identifies a novel group of tumor-associated N-acetylglucosamine glycan antigens." Cancer research. Jul. 15, 2009;69(14): pp. 5811-5819.
Satomaa, T., et al. "The N-glycome of human embryonic stem cells." BMC cell biology." [Research Support, Non-U.S. Gov't]. 2009;10:42.
Schulenberg, B. et al. "Mapping glycosylation changes related to cancer using the Mutiplexed Proteomics technology: a protein differential display approach." Journal of Chromatography B 793, Elsevier, pp. 127-139 (2003).

Shami, V.M., et al. "The level of carcinoembryonic antigen and the presence of mucin as predictors of cystic pancreatic mucinous neoplasia." Pancreas. May 2007;34(4): pp. 466-469.
Sina, M., et al. Improving the diagnostic accuracy of endoscopic ultrasound-guided fine-needle aspiration using microRNAs. Gastroenterology 2014; 147:930-932.
Singh, M., et al. "Precursor lesions of pancreatic cancer: molecular pathology and clinical implications." Pancreatology. 2007;7(1): pp. 9-19.
Singh, S., et al. Upregulation of glycans containing 3' fucose in a subset of pancreatic cancers uncovered using fusion-tagged lectins, J Proteome Res, 14 (2015), pp. 2594-2605.
Tachezy, M., et al. "Angiogenesis index CD105 (endoglin)/CD31 (PECAM-1) as a predictive factor for invasion and proliferation in intraductal papillary mucinous neoplasm (IPMN) of the pancreas." Histology and histopathology. Oct. 2010;25(10): pp. 1239-1246.
Takahashi, S., et al. Overexpression of sialyl Lewis x antigen is associated with formation of extratumoral venous invasion and predicts postoperative development of massive hepatic metastasis in cases with pancreatic ductal adenocarcinoma. Pathobiology 2001;69:127-135.
Takasaki, H., et al. Correlative study on expression of CA 19-9 and DU-PAN-2 in tumor tissue and in serum of pancreatic cancer patients. Cancer Res 1988;48:1435-1438.
Tanaka, M., et al. "International consensus guidelines 2012 for the management of IPMN and MCN of the pancreas." Pancreatology. Apr. 8, 2012;12(3): pp. 183-197.
Tang, H., et al. Glycan motif profiling reveals plasma sialyl-Lewis X elevations in pancreatic cancers that are negative for sialyl-Lewis A*, Mol Cell Proteomics, 14 (2015), pp. 1323-1333.
Taussig, M.J., et al., "Progress in antibody arrays." Targets, 2003, 2(4): pp. 169-176.
Thayer, S.P., et al. Hedgehog is an early and late mediator of pancreatic cancer tumorigenesis. Nature 2003;425:851-856.
Torres, M.P., et al. "Mucin-based targeted pancreatic cancer therapy." Curr Pharm Des.(Dec. 27, 2012) 18(17): pp. 2472-2481.
Van der Waaij L., et al. "Cyst fluid analysis in the differential diagnosis of pancreatic cystic lesions: a pooled analysis." Gastrointestinal Endoscopy. Sep. 2005;62(3): pp. 383-389.
Vijayendran, R.A., et al. "A Quantitative Assessment of Heterogeneity for Surface-Immobiled Proteins." Anal. Chem. 2001, 73:471-480.
Visser, BC, et al. "Characterization of cystic pancreatic masses: relative accuracy of CT and MRI." AJR Am J Roentgenol. Sep. 2007;189(3): pp. 648-656.
Wang, Y., et al. "Cosmc is an essential chaperone for correct protein O-glycosylation." Proceedings of the National Academy of Sciences of the United States of America. May 18, 2010;107(20): pp. 9228-9233.
West, M.B., et al. "Analysis of site-specific glycosylation of renal and hepatic gamma-glutamyl transpeptidase from normal human tissue." The Journal of biological chemistry. Sep. 17, 2010;285(38): pp. 29511-29524.
Whitelock, J.M., et al. "Diverse cell signaling events modulated by perlecan." Biochemistry. Oct. 28, 2008;47(43):11174-83.
Wu, Y.M., et al. "Mucin glycosylation is altered by pro-inflammatory signaling in pancreatic-cancer cells." J Proteome Res. Apr. 2009, vol. 8(4):1876-1886.
Wu, J., et al. "Recurrent GNAS Mutations Define an Unexpected Pathway for Pancreatic Cyst Development." Sci Transl Med. Jul. 20, 2011;3(92):92ra66.
Wu, J.T. "Serum alpha-fetoprotein and its lectin reactivity in liver diseases: a review." Ann Clin Lab Sci. Mar.-Apr. 1990;20(2):98-105.
Wu, P., et al. "Comparison of hydroxylated print additives on antibody microarray performance." J Proteome Res. 2006; 5(11): pp. 2956-2965.
Yin, B. et al. "Molecular Cloning of the CA125 Ovarian Cancer Antigen: Identification as a New Mucin, MUC16." Journal of Biological Chemistry, vol. 276 (No. 29), pp. 27371-27375, (Jul. 20, 2001).

(56) References Cited

OTHER PUBLICATIONS

Yonezawa, S., et al., "The expression of several types of mucin is related to the biological behavior of pancreatic neoplasms." J Hepatobiliay Pancreat. Surg., 2002, 9: pp. 328-341.

Yue, T., et al. "Enhanced Discrimination of Malignant from Benign Pancreatic Disease by Measuring the CA 19-9 Antigen on Specific Protein Carriers." PLoS One 6(12): e29180; Dec. 29, 2011.

Yue, T., et al., "The Prevalence and nature of glycan alterations on specific proteins in pancreatic cancer Patients revealed using antibody-lectin sandwich arrays." Molecular & Cellular Proteomics, Jul. 8, 2009: pp. 1697-1707.

Yue, T., et al. "Microarrays in glycoproteomics research." Clin Lab Med. Mar. 2009; 29(1):15-29.

Zhou, H. et al. "Two-color, rolling-circle amplification on antibody microarrays for sensitive, multiplexed serum-protein measurements." Genome Biology, Article R28, Open Access, vol. 5 (No. 4), pp. 1-12, (Mar. 30, 2004).

Zill, O.A., et al. Cell-Free DNA next-generation sequencing in pancreatobiliary carcinomas. Cancer Discov 2015;5:1040-1048.

Maupin, K., et al. Abstract 4555: Protein and glycan biomarkers and malignant potential in pancreatic cyst fluid. Cancer Res Apr. 15, 2012 72:4555.

Shamblott, Michael J., et al. Derivation of pluripotent stem cells from cultured human primordial germ cells. Proc. Natl. Acad. Sci., USA vol. 95, pp. 13726-13731 Nov. 1998.

Tang, Huiyuan, et al. Glycans Related to the CA19-9 Antigen Are Increased in Distrinct Subsets of Pancreatic Cancers and Improve Diagnostic Accuracy Over CA19-9. Cell Mol Gastroenterol Hepatol, Feb. 1, 2016; 2(2):210-221 with supplementary materials thur 221.e15.

Adamczyk, B et al., "Glycans as cancer biomarkers" Biochimica et Biophysica Acta (BBA)-General Subjects, 2012, 1820(9), 1347-1353.

Angel, PM et al., "Extracellular Matrix Imaging of Breast Tissue Pathologies by MALDI-Imaging Mass Spectrometry" In Tissue Proteomics, 2017, (pp. 225-241). Humana Press, New York, NY.

Chen S et al. "Multiplexed analysis of glycan variation on native proteins captured by antibody microarrays" Nature Methods, 2007, 4(5), 437-444.

Drake, RR et al., "MALDI Mass Spectrometry Imaging of N-Linked Glycans in Cancer Tissues" In Advances in Cancer Research, 2017, (vol. 134, pp. 85-116). Academic Press.

Gustafsson, OJ et al., "MALDI imaging mass spectrometry of N-linked glycans on formalin-fixed paraffin-embedded murine kidney" Analytical and bioanalytical chemistry, 2015, 407(8), 2127-2139.

Heijs, B et al., "MALDI-2 for the Enhanced Analysis of N-Linked Glycans by Mass Spectrometry Imaging" Analytical Chemistry, 2016, 88(15), 7745-7753.

Kailemia, MJ, et al., "Glycans and glycoproteins as specific biomarkers for cancer." Anal Bioanal Chem 409, 395-410 (2017). https://doi.org/10/1007/s00216-016-9880-6.

Kunzke, T et al., "Native glycan fragments detected by MALDI-FT-ICR mass specrometry imaging impact gastric cancer biology and patient outcome" Oncotarget, 2017, 8(40)68012, 14 pages.

Kuzmanov, U et al., "The sweet and sour of serological glycoprotein tumor biomarker quanitification." BMC Med 11, 31 (2013). 14 pages. https://doi.org/10.1186/174-7015-11-31.

Lamontagne, A et al., "Altered Functionality of Anti-Bacterial Antibodies in Patients with Chronic Hepatitis C Virus Infection" PloS one, 2013, 8(6), e64992, 11 pages.

Meany, DL et al., "Aberant glycosylation associated with enzymes as cancer biomarkers" Clinical proteomics, 2011, 8 (1), 7, 14 pages.

Mehta, AS et al., "Increased Levels of Galactose-Deficient Anti-Gal Immunoglobulin G in the Sera of Hepatitis C Virus- Infected Individiuals with Fibrosis and Cirrhosis" Journal of virology, 2008, 82(3), 1259-1270.

Mittermayr, S et al., "Multiplexed Analytical Glycomics: Rapid and Confident IgG N-Glycan Structural Elucidation" Journal of proteome research, 2011, 10(8), 3820-3829.

Nagaraj, VJ et al., "Piezoelectric printing and probing of Lectin NanoProbeArrays for glycosylation analysis" Biochemical and biophysical research communications, 2008, 375(4) 526-530.

Ohtsubo, K et al., "Glycosylation in Cellular Mechanisms of Health and Disease" Cell, 2006, 126(5), 855-867.

Patwa, TH et al., "Screening of glycosylation patterns in serum using natural glycoprotein microarrays and multi-lectin fluorescence detection" Analytical chemistry, 2006, 78(18), 6411-6421.

Powers, T et al., "Two-Dimensional N-Glycan Distribution Mapping of Hepatocellular Carcinoma Tissues by MALDI- Imaging Mass Spectrometry" Biomolecules, 2015, 5(4), 2554-2572.

Powers, TW et al., "MALDI Imaging Mass Spectrometry Profiling of N-Glycans in Formalin-Fixed Paraffin Embedded Clinical Tissue Blocks and Tissue Microarrays" Plos One, 2014 9(9), e106255, 11 pages.

Saldova, R et al., "N-Glycosylation of Serum IgG and Total Glycoproteins in MAN1B1 Deficiency" Journal of proteome research, 2015, 14(10), 4402-4412.

Scott, DA et al., "Increases in Tumor N-Glycan Polylactosamines Associated with Advanced HER2-Positive and Triple-Negative Breast Cancer Tissues" PROTEOMICS-Clinical Applications, 2019, 13(1), 1800014, 10 pages.

West, CA et al., "N-Linked Glycan Branching and Fucosylation Are Increased Directly in Hcc Tissue as Determined Through In Situ Glycan Imaging" Journal of proteome research, 2018, 17(1), 3454-3462.

U.S. Appl. No. 11/375,756, filed Mar. 15, 2006, Sang, Hong, Issued.
U.S. Appl. No. 12/951,718, filed Nov. 22, 2010, Sang, Hong, Issued.
U.S. Appl. No. 13/519,766, filed Sep. 10, 2012, Bunker, Amy M., Abandoned.
U.S. Appl. No. 14/203,049, filed Mar. 10, 2014, Xiao, Yan, Abandoned.
U.S. Appl. No. 15/216,768, filed Jul. 22, 2016, Harris Dent, Alana, Issued.
U.S. Appl. No. 17/059,660, filed Nov. 30, 2020, Alex Ramirez, Published.

* cited by examiner

FIG. 1A

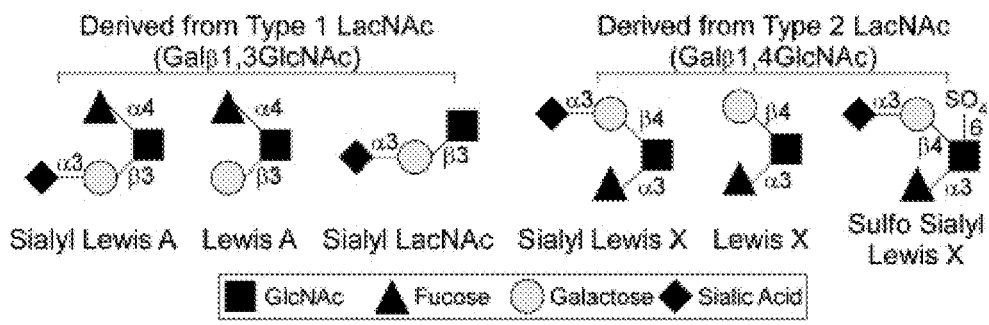

FIG. 1B

| Glycan | Structure | Abbreviation | Mouse E-selectin (SELE) | Anti-sLeA (9L426) | Anti-sLeX (CSLEX1) | Anti-LeA (7LE) | TRA-1-60 | CCL2 |
|---|---|---|---|---|---|---|---|---|
| Sialyl-Lewis A | Siaα2,3Galβ1,3(Fucα1,4)GlcNAcβ | sLeA | ■ | ■ | | | | |
| Lewis A | Galβ1,3(Fucα1,4)GlcNAcβ | LeA | | | | ■ | | |
| Sialyl LacNAc type1 | Siaα2,3Galβ1,3GlcNAcβ | sLacNAc t1 | | | | | | |
| Terminal LacNAc type1 | Galβ1,3GlcNAcβ | LacNAc t1 | | | | ■ | | |
| Sialyl LacNAc type1-type2 repeat | Siaα2,3Galβ1,3GlcNAcβ1,3Galβ1,4GlcNAc | sLacNAc t1t2 | | | | | | |
| Terminal LacNAc type1-type2 repeat | Galβ1,3GlcNAcβ1,3Galβ1,4GlcNAc | LacNAc t1t2 | | | | | ■ | |
| Sialyl-Lewis X | Siaα2,3Galβ1,4(Fucα1,3)GlcNAcβ | sLeX | ■ | | ■ | | | ■ |
| Sulfo/sialyl Lewis X | Siaα2,3Galβ1,4(Fucα1,3)(6SO4)GlcNAcβ | sulfo-sLeX | ■ | | | | | ■ |
| Terminal Lewis X | Galβ1,4(Fucα1,3)GlcNAcβ | LeX | | | | | | ■ |
| Internal Lewis X | (Any)Galβ1,4(Fucα1,3)GlcNAcβ | Int LeX | | | | | | ■ |

FIG. 4C

Combined Cohorts

| | Markers | Sensitivity | Specificity | Accuracy |
|---|---|---|---|---|
| sLeA | sLeA:sLeA | 54% | 86% | 70% |
| Panel 1 | MUC5AC:sLeA/sLacNAc t1, sLeA:sulfo/sLeX/sLeA, MUC5AC:sulfo/sLeX | 85% | 90% | 88% |
| Panel 2 | MUC5AC:sLacNAc t1/2, sLeA:sulfo/sLeX/sLeA, MUC5AC:sulfo/sLeX | 88% | 85% | 86% |

FIG. 6

| v5.0 GlycanID | 9L426 2 ug/ml | 9L426 20 ug/ml | 7LE 20 ug/ml | Glycan Structure |
|---|---|---|---|---|
| 332 | 24737.7 | 33518.0 | | Neu5Aca2-3Galb1-3(Fuca1-4)GlcNAcb1-3Galb1-3(Fuca1-4)GlcNAcb-Sp0 |
| 240 | 11819.5 | 37934.5 | | Neu5Aca2-3Galb1-3(Fuca1-4)GlcNAcb-Sp8 |
| 241 | 32815.1 | 34101.9 | | Neu5Aca2-3Galb1-3(Fuca1-4)GlcNAcb1-3Galb1-4(Fuca1-3)GlcNAcb-Sp0 |
| 281 | | 89.2 | | Neu5Gca2-3Galb1-3(Fuca1-4)GlcNAcb-Sp0 |
| 400 | | 1391.7 | | Neu5Aca2-3Galb1-3GlcNAcb1-3GalNAca-Sp14 |
| 295 | | 1591.4 | | Neu5Aca2-3Galb1-3GlcNAcb1-3Galb1-3GlcNAcb-Sp0 |
| 248 | | 631.0 | | Neu5Aca2-3Galb1-3GlcNAcb1-3Galb1-4GlcNAcb-Sp0 |
| 494 | | 71.5 | | Galb1-4(Fuca1-3)GlcNAcb1-6(Neu5Aca2-6(Neu5Aca2-3Galb1-3)GlcNAcb1-3)Galb1-4Glc-Sp21 |
| 126 | | | 28245.4 | Galb1-3(Fuca1-4)GlcNAcb1-3Galb1-4(Fuca1-3)GlcNAcb-Sp0 |
| 127 | | | 16500.4 | Galb1-3GlcNAcb1-3Galb1-4(Fuca1-3)GlcNAcb-Sp0 |
| 277 | | | 9179.0 | Galb1-3(Fuca1-4)GlcNAcb1-3Galb1-3(Fuca1-4)GlcNAcb-Sp0 |
| 382 | | | 4738.1 | Galb1-3GlcNAcb1-3Galb1-4GlcNAcb1-6(Galb1-3GlcNAcb1-3)Galb1-4Glcb-Sp0 |
| 571 | | | 4450.2 | Galb1-3GlcNAcb1-3Galb1-4GlcNAcb1-3Galb1-4GlcNAcb1-6(Galb1-3GlcNAcb1-3Galb1-4GlcNAcb1-2)Mana1-6(Galb1-3GlcNAcb1-3Galb1-4GlcNAcb1-3Galb1-4GlcNAcb1-2Mana1-3)Manb1-4GlcNAcb1-4(Fuca1-6)GlcNAcb-Sp24 |
| 386 | | | 4308.6 | Galb1-3GlcNAcb1-3Galb1-4(Fuca1-3)GlcNAcb1-6(Galb1-3GlcNAcb1-3)Galb1-4Glc-Sp21 |
| 572 | | | 3834.9 | Galb1-3GlcNAcb1-3Galb1-4GlcNAcb1-6(Galb1-3GlcNAcb1-3Galb1-4GlcNAcb1-2)Mana1-6(Galb1-3GlcNAcb1-3Galb1-4GlcNAcb1-2Mana1-3)Manb1-4GlcNAcb1-4(Fuca1-6)GlcNAcb-Sp24 |
| 383 | | | 3808.9 | Galb1-4(Fuca1-3)GlcNAcb1-6(Galb1-3GlcNAcb1-3)Galb1-4Glc-Sp21 |
| 391 | | | 2997.1 | Galb1-3GlcNAcb1-3GalNAca-Sp14 |
| 148 | | | 2612.6 | Galb1-3GlcNAcb1-3Galb1-4Glcb-Sp10 |
| 289 | | | 2090.0 | Galb1-3GlcNAcb1-3Galb1-3GlcNAcb-Sp0 |
| 551 | | | 1338.1 | Galb1-3GlcNAcb1-3Galb1-4GlcNAcb1-2Mana1-6(Galb1-3GlcNAcb1-3Galb1-4GlcNAcb1-2Mana1-3)Manb1-4GlcNAcb1-4GlcNAc-Sp25 |
| 147 | | | 993.0 | Galb1-3GlcNAcb1-3Galb1-4GlcNAcb-Sp0 |
| 477 | | | 929.7 | Neu5Aca2-6Galb1-4GlcNAcb1-6(Galb1-3GlcNAcb1-3)Galb1-4Glcb-Sp21 |
| | | | 744.3 | Neu5Aca2-6(Galb1-3)GlcNAcb1-4Galb1-4Glcb-Sp10 |
| | | | 741.5 | Galb1-4GlcNAcb1-6(Fuca1-4(Fuca1-2Galb1-3)GlcNAcb1-3)Galb1-4Glc-Sp21 |
| | | | 635.2 | Galb1-3GlcNAcb1-6Galb1-4GlcNAcb-Sp0 |
| | | | 496.2 | Galb1-3(Fuca1-4)GlcNAc-Sp8 |
| | | | 483.5 | Galb1-4GlcNAcb1-3Galb1-4GlcNAcb1-2Mana1-6(Galb1-4GlcNAcb1-3Galb1-4GlcNAcb1-2Mana1-3)Manb1-4GlcNAcb1-4GlcNAcb-Sp12 |
| | | | 442.8 | Galb1-3(Fuca1-4)GlcNAc-Sp0 |
| | | | 273.2 | Galb1-3(Fuca1-4)GlcNAcb-Sp8 |
| 254 | | | | Neu5Aca2-3Galb1-4(Fuca1-3)GlcNAcb1-3Galb1-4(Fuca1-3)GlcNAcb1-3Galb1-4(Fuca1-3)GlcNAcb-Sp0 |
| 256 | | | | Neu5Aca2-3Galb1-4(Fuca1-3)GlcNAcb-Sp8 |
| 253 | | | | Neu5Aca2-3Galb1-4(Fuca1-3)(6S)GlcNAcb-Sp8 |
| 257 | | | | Neu5Aca2-3Galb1-4(Fuca1-3)GlcNAcb1-3Galb-Sp8 |
| 231 | | | | Neu5Aca2-3(6S)Galb1-4(Fuca1-3)GlcNAcb-Sp8 |

FIG. 7

| ID | hE-sel 2 ug/ml | hE-sel 10 ug/ml | mE-sel 0.5 ug/ml | mE-sel 5 ug/ml | Glycan Name |
|---|---|---|---|---|---|
| v3.0 | 1001654 | 1001653 | 1001665 | 1001664 | Dataset ID |
| 257 | 35871.0 | 51830.2 | 10939.9 | 37095.5 | Neu5Gca2-3Galb1-3(Fuca1-4)GlcNAcb-Sp0 |
| 217 | 24986.1 | 49732.2 | 9080.4 | 40518.0 | Neu5Aca2-3Galb1-3(Fuca1-4)GlcNAcb-Sp8 |
| 218 | 4965.7 | 18110.2 | 2754.2 | 42049.1 | Neu5Aca2-3Galb1-3(Fuca1-4)GlcNAcb1-3Galb1-4(Fuca1-3)GlcNAcb-Sp0 |
| 232 | 3133.2 | 12591.3 | 2063.4 | 41704.9 | Neu5Aca2-3Galb1-4(Fuca1-3)GlcNAcb1-3Galb-Sp8 |
| 31 | 2615.9 | 5867.7 | 9071.3 | 39851.2 | [3OSO3]Galb1-3(Fuca1-4)GlcNAcb-Sp8 |
| 265 | 2162.4 | 4248.2 | 10507.5 | 38438.3 | [3OSO3]Galb1-4(Fuca1-3)[6OSO3]Glc-Sp0 |
| 267 | 2449.6 | 6542.8 | 3649.6 | 23237.4 | [3OSO3]Galb1-4(Fuca1-3)[6OSO3]GlcNAc-Sp8 |
| 26 | 2762.0 | 7394.6 | | | [3OSO3][6OSO3]Galb1-4[6OSO3]GlcNAcb-Sp0 |
| 288 | | 5756.2 | | | [6OSO3]Galb1-4[6OSO3]GlcNAcb-Sp0 |
| 271 | | 5562.3 | | | Fuca1-2[6OSO3]Galb1-4[6OSO3]Glc-Sp0 |
| 35 | | 4789.0 | | | [3OSO3]Galb1-4[6OSO3]GlcNAcb-Sp8 |
| 45 | | 4373.5 | | | [6OSO3]Galb1-4[6OSO3]Glcb-Sp8 |
| 39 | | 3391.2 | | | [4OSO3][6OSO3]Galb1-4GlcNAcb-Sp0 |
| 27 | | 4610.8 | | | [3OSO3][6OSO3]Galb1-4GlcNAcb-Sp0 |
| 29 | | 4955.4 | | | [3OSO3]Galb1-4[6OSO3]Glcb-Sp0 |
| 287 | 2636.7 | 4558.5 | | | [3OSO3][4OSO3]Galb1-4GlcNAcb-Sp0 |
| 30 | | 3362.5 | | | [3OSO3]Galb1-4[6OSO3]Glcb-Sp8 |
| 227 | 3055.0 | 3884.5 | | | Neu5Aca2-3Galb1-4[6OSO3]GlcNAcb-Sp8 |
| 244 | | | | | Neu5Aca2-6Galb1-4[6OSO3]GlcNAcb-Sp8 |
| 228 | | 3775.1 | 2153.1 | 47873.8 | Neu5Aca2-3Galb1-4(Fuca1-3)[6OSO3]GlcNAcb-Sp8 |
| 231 | | 3411.8 | 2986.2 | 45569.2 | Neu5Aca2-3Galb1-4(Fuca1-3)GlcNAcb-Sp8 |
| 233 | | | 2126.5 | 44456.1 | Neu5Aca2-3Galb1-4(Fuca1-3)GlcNAcb1-3Galb1-4GlcNAcb-Sp8 |
| 259 | | | 2058.8 | 35006.2 | Neu5Gca2-3Galb1-4(Fuca1-3)GlcNAcb-Sp0 |
| 229 | | | 3128.6 | 37277.0 | Neu5Aca2-3Galb1-4(Fuca1-3)GlcNAcb1-3Galb1-4(Fuca1-3)GlcNAcb-3Galb1-4(Fuca1-3)GlcNAcb-Sp0 |
| 230 | | | | 38951.8 | Neu5Aca2-3Galb1-4(Fuca1-3)GlcNAcb-Sp0 |
| 293 | | | | 29502.2 | Galb1-3(Neu5Aca2-3Galb1-4(Fuca1-3)GlcNAcb1-6)GalNAc-Sp14 |
| 247 | | | | | Neu5Aca2-6Galb1-4GlcNAcb1-3Galb1-4(Fuca1-3)GlcNAcb1-3Galb1-4(Fuca1-3)GlcNAcb-Sp0 |
| 47 | | 3237.0 | | | [6OSO3]GlcNAcb-Sp8 |
| 40 | 2294.5 | 3778.3 | | | [4OSO3]Galb1-4GlcNAcb-Sp8 |
| 139 | | | | | Galb1-4[6OSO3]Glcb-Sp0 |
| 37 | | 3504.4 | | | [3OSO3]Galb1-4GlcNAcb-Sp8 |
| 38 | 2117.2 | 4509.9 | | | [3OSO3]Galb-Sp8 |
| 36 | | 3764.0 | | | [3OSO3]Galb1-4GlcNAcb-Sp0 |
| 272 | | | | | Fuca1-2[6OSO3]Galb1-4Glc-Sp0 |
| 117 | | | | 12977.7 | Galb1-3(Fuca1-4)GlcNAc-Sp0 |
| 115 | | | | 11950.2 | Galb1-3(Fuca1-4)GlcNAcb1-3Galb1-4(Fuca1-3)GlcNAcb-Sp0 |
| 274 | | | | 11543.5 | Galb1-3(Fuca1-4)GlcNAcb1-3Galb1-3(Fuca1-4)GlcNAcb-Sp0 |
| 119 | | | | 11261.2 | Galb1-3(Fuca1-4)GlcNAcb-Sp8 |
| 118 | | | | 9249.1 | Galb1-3(Fuca1-4)GlcNAc-Sp8 |
| 57 | | | | 6565.6 | Fuca1-2Galb1-3(Fuca1-4)GlcNAcb-Sp8 |
| 116 | | | | | Galb1-3(Fuca1-4)GlcNAcb1-3Galb1-4GlcNAcb-Sp0 |
| 266 | | | 2234.2 | 50836.0 | [3OSO3]Galb1-4(Fuca1-3)Glc-Sp0 |
| 34 | | | | 32021.5 | [3OSO3]Galb1-4(Fuca1-3)GlcNAcb-Sp8 |
| 268 | | | | 14917.2 | [3OSO3]Galb1-4(Fuca1-3)GlcNAc-Sp0 |
| 281 | | | | 17427.5 | Galb1-4(Fuca1-3)[6OSO3]Glc-Sp0 |
| 280 | | | | 3260.5 | Galb1-4(Fuca1-3)[6OSO3]GlcNAc-Sp0 |

FIG. 8A
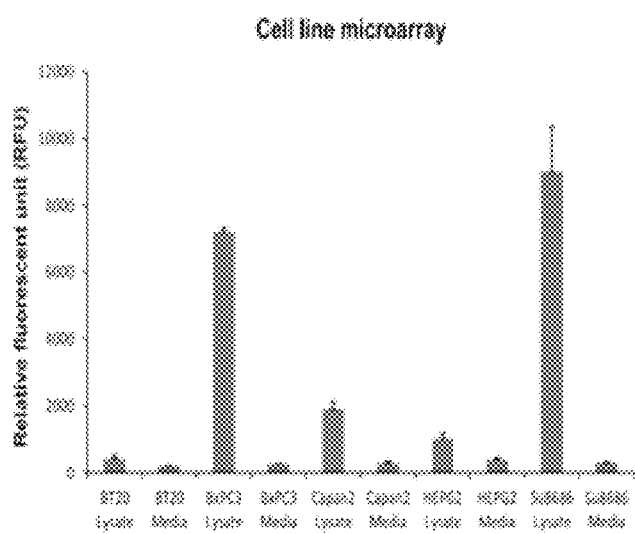
FIG. 8B
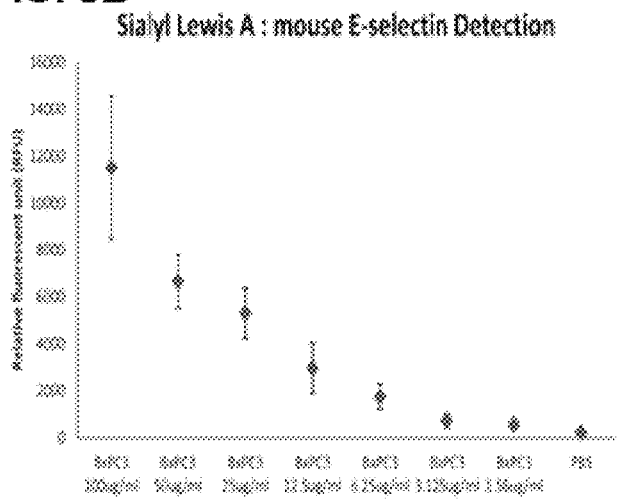
FIG. 8C
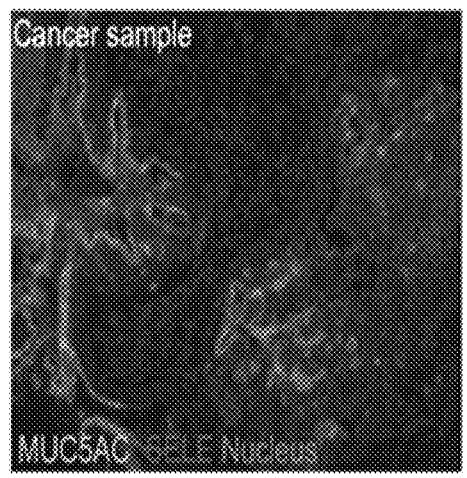
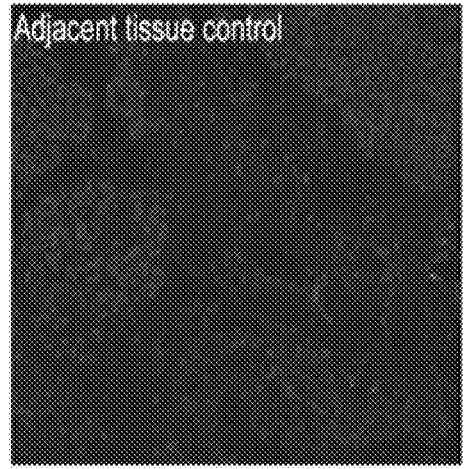

METHODS FOR DETECTING AND FOR TREATING PANCREATIC CANCER

STATEMENT REGARDING FEDERALLY SPONSORED RESEARCH OR DEVELOPMENT

This invention was made with government support under U01 CA152653, U01 CA168896, and R41 GM112750 awarded by the National Institutes of Health. The government has certain rights in the invention.

CROSS-REFERENCE TO RELATED APPLICATIONS

This application is a divisional application of U.S. patent application Ser. No. 15/216,768, filed Jul. 22, 2016, the entire contents of which are incorporated by reference.

FIELD OF THE INVENTION

The present invention is in the field of biochemistry and medicine and relates to glycan detection methods and methods for detecting and for treating pancreatic cancer.

BACKGROUND OF THE INVENTION

Many pancreatic cancers secrete glycoproteins and glycolipids that bear a glycan called sialyl-Lewis A (sLeA). The sLeA glycan forms the basis for the Food and Drug Administration-approved cancer antigen 19-9 (CA19-9) blood test, named after the monoclonal antibody first developed against the sLeA glycan. The test is used as an approximate indicator of extent of disease recurrence, but a problem with the CA19-9 antigen is that it is not increased in a substantial proportion of patients. By using a typical cut-off value of 37 U/mL, approximately 25%-35% of patients do not show increases, rendering the test inconclusive for the diagnosis or monitoring of cancer in many patients. However, the test is very specific for cancer at high cut-off values. Therefore, CA19-9 represents an important marker for pancreatic cancer and a good basis on which to build molecular indicators for cancer, but it needs to be improved. After many years of research since the discovery of CA19-9, a biomarker validated to perform better than CA19-9 for pancreatic cancer detection is not yet available. Improving the CA19-9 blood test or identifying another marker to detect cancer among patients with low CA19-9 levels potentially could lead to an improved diagnostic test.

The sLeA glycan is part of a family of glycans called the "Lewis antigens", named after the discoverer of a series of antigens found on red blood cells comprising a system of blood types. The Lewis glycans generally appear on the termini of oligosaccharides attached to both proteins and lipids. The common feature among the family members is a core N-acetyl-lactosamine (LacNAc), which is a disaccharide of galactose linked to N-acetylglucosamine. The monosaccharides fucose and sialic acid can be attached to the LacNAc in various linkages. A sulfate group also can be attached to the galactose or N-Acetylglucosamine. In the normal pancreas, sLeA appears on the epithelial surfaces of the ducts, and in the cancerous pancreas it can be heavily secreted into the lumen of the proliferating ducts. The increase of sLeA in the blood likely results from accumulation in the stroma followed by leakage into the capillaries or lymph. One reason for the lack of increase in CA19-9 levels is genetics. A glycosyltransferase enzyme that is critical for the biosynthesis of sLeA, fucosyltransferase 3, is inactive in approximately 5% of the North American population as a result of homozygous mutations in the active part of the gene. But the cause of low CA19-9 levels is not clear for patients with wild-type fucosyltransferase 3.

Other members of the Lewis antigens besides sLeA also appear both in the normal and cancerous pancreas. An isomer of sLeA called sialyl Lewis X (sLeX) is up-regulated in the tissue of some pancreatic cancers, and the inventors and others found it increased in the circulation of many pancreatic cancer patients. Some patients have an increase in a glycan detected by the DUPAN-2 monoclonal antibody, identified primarily as type 1 sialyl-LacNAc. And the inventors' previous research also found indirect evidence for additional glycans by comparing patient increases between anti-sLeA antibodies with either broad or narrow specificity.

These observations suggest that diversity exists between pancreatic cancers in the type of glycans they make and secrete into the blood; and that a variety of glycans is secreted, with differences between individual cancers. Thus, to encompass the full range of pancreatic cancers, assays are needed to detect the various antigens that pancreatic cancers are expressing in addition to sLeA, and that are not normally increased under healthy or benign conditions. Improved assays to detect sLeA, or assays to detect the additional cancer-associated glycans could be used to identify a higher percentage of pancreatic cancer patients.

SUMMARY OF THE INVENTION

The inventors have shown that glycans besides sialyl-Lewis A (sLeA) are increased in distinct groups of patients and contribute to the improved accuracy of a biomarker panel. The inventors found significant increases in two glycans: (1) sialyl-Lewis X (sLeX), an isomer of sLeA, present both in sulfated and nonsulfated variants, and (2) sialylated type 1 N-acetyl-lactosamine (sLacNAc t1), the sialylated form of a marker for pluripotent stem cells. The glycans performed as well as sLeA as individual markers and were increased in distinct groups of patients, resulting in a 3-marker panel that significantly improved upon any individual biomarker. The panel showed 85% sensitivity and 90% specificity in the combined discovery and validation cohorts, relative to 54% sensitivity and 86% specificity for sLeA; and it showed 80% sensitivity and 84% specificity in the independent test cohort, as opposed to 66% sensitivity and 72% specificity for sLeA. The three types of glycans—sLeA, sLeX variants, and sialylated type 1 LacNAc—possess structures and functions associated with particular differentiation states. These new glycan biomarkers have the potential to improve the accuracy of diagnosing pancreatic cancer and to shed light on the molecular differences between tumors.

The inventors also have developed a method for detecting a level of a glycan in a biological sample from a subject which includes using a capture reagent to immobilize the glycan on a substrate; exposing the immobilized glycan to a detection reagent; visualizing the bound detection reagent to detect the level of the immobilized glycan; and performing one or both of following steps: (a) before exposing the biological sample to the capture reagent, combining one or more pre-capture enzymes with the biological sample and (b) before exposing the immobilized glycan to the detection reagent, exposing the immobilized glycan to one or more pre-detection enzymes. The inventors have found that the use of the pre-capture and/or predetection enzymes will increase the level of glycans that can be detected.

One aspect of the invention is a method of diagnosing pancreatic cancer in a human patient which includes: obtaining a biological sample from the human patient, wherein the biological sample includes one or more glycoforms of a Lewis antigen and one or more glycoforms of a mucin 5AC (MUC5AC); detecting a level of the one or more glycoforms of the Lewis antigen and a level of the one or more glycoforms of MUC5AC in the biological sample; and diagnosing the patient with pancreatic cancer when the one or more glycoforms of the Lewis antigen and the one or more glycoforms of MUC5AC are at a different level than a statistically validated threshold for the one or more glycoforms of the Lewis antigen and the one or more glycoforms of MUC5AC.

In another aspect of the inventive method, the one or more glycoforms of the Lewis antigen are sialyl-Lewis A:sialyl-Lewis A (sLeA:sLeA), sialyl-Lewis A:sulfated Lewis A (sLeA:sulfo-LeA), sialyl-Lewis A:sulfated sialyl-Lewis A (sLeA:sulfo-sLeA), sialyl-Lewis A:sialyl-Lewis X (sLeA:sLeX), sialyl-Lewis A:sulfated Lewis X (sLeA:sulfo-LeX), or sialyl-Lewis A:sulfated sialyl-Lewis X (sLeA:sulfo-sLeX). And in a further aspect of the invention the one or more glycoforms of MUC5AC are MUC5AC:type 1 sialyl-N-acetyl-lactosamine (MUC5AC:sLacNAc t1), MUC5AC:typeltype 2 sialyl-N-acetyl-lactosamine (MUC5AC:sLacNAc t1t2), MUC5AC:sialyl-Lewis A (MUC5AC:sLeA), MUC5AC:sialyl-Lewis X (MUC5AC:sLeX), MUC5AC:sulfated-Lewis A (MUC5AC:sulfo-LeA), MUC5AC:sulfated-Lewis X (MUC5AC:sulfo-LeX), MUC5AC:sulfated sialyl-Lewis A (MUC5AC:sulfo-sLeA), or MUC5AC:sulfated sialyl-Lewis X (MUC5AC:sulfo-sLeX). The one or more glycoforms of the Lewis antigen may be sLeA:sulfo-sLeA and sLeA:sulfo-sLeX; the one or more glycoforms of MUC5AC may be MUC5AC:sLeA, MUC5AC:sLacNAc t1 and MUC5AC:sulfo-sLeX; and the one or more glycoforms of MUC5AC may be MUC5AC:sLacNAc t1t2 and MUC5AC:sulfo-sLeX.

In some embodiments of the inventive method, the one or more glycoforms of the Lewis antigen and the one or more glycoforms of MUC5AC may be detected with one or more glycan-binding proteins; for example, the one or more glycoforms of the Lewis antigen may be detected with an E-selectin lectin, and the one or more glycoforms of MUC5AC may be detected with a 7LE anti-Lewis antigen antibody, a TRA-1-60 anti-Lewis antigen antibody, or a *Coprinopsis cinerea* lectin 2 (CCL2).

In other embodiments, the level of the one or more glycoforms of the Lewis antigen and the level of the one or more glycoforms of MUC5AC in the biological sample may elevated as compared to the statistically validated thresholds for the one or more glycoforms of the Lewis antigen and the one or more glycoforms of MUC5AC; the sample may be blood serum; and/or the diagnosis may differentiate pancreatic cancer from benign pancreatic disease.

In a further aspect, the inventive method is diagnosing pancreatic cancer in a human patient. This method includes obtaining a biological sample from the human patient, wherein the biological sample includes one or more glycoforms of a Lewis antigen and one or more glycoforms of MUC5AC; detecting a level of the one or more glycoforms of the Lewis antigen and the one or more glycoforms of the MUC5AC in the biological sample; obtaining an image of the pancreas of the patient; and diagnosing the patient with pancreatic cancer when (a) the one or more glycoforms of the Lewis antigen and the one or more glycoforms of the MUC5AC are at a different level than a statistically validated threshold for the one or more glycoforms of the Lewis antigen and the one or more glycoforms of the MUC5AC and (b) the image of the pancreas indicates pancreatic cancer in the patient. In some aspects of the inventive method, the image may be obtained by performing an ultrasound (US), computerized tomography (CT) scanning, or magnetic resonance imaging (MRI) of the pancreas of the patient.

In another aspect of the inventive method for detecting glycoform levels and imaging the pancreas, the one or more glycoforms of the Lewis antigen are sialyl-Lewis A:sialyl-Lewis A (sLeA:sLeA), sialyl-Lewis A:sulfated Lewis A (sLeA:sulfo-LeA), sialyl-Lewis A:sulfated sialyl-Lewis A (sLeA:sulfo-sLeA), sialyl-Lewis A:sialyl-Lewis X (sLeA:sLeX), sialyl-Lewis A:sulfated Lewis X (sLeA:sulfo-LeX), or sialyl-Lewis A:sulfated sialyl-Lewis X (sLeA:sulfo-sLeX). And in a further aspect of the invention the one or more glycoforms of MUC5AC are MUC5AC:type 1 sialyl-N-acetyl-lactosamine (MUC5AC:sLacNAc t1), MUC5AC:typeltype 2 sialyl-N-acetyl-lactosamine (MUC5AC:sLacNAc t1t2), MUC5AC:sialyl-Lewis A (MUC5AC:sLeA), MUC5AC:sialyl-Lewis X (MUC5AC:sLeX), MUC5AC:sulfated-Lewis A (MUC5AC:sulfo-LeA), MUC5AC:sulfated-Lewis X (MUC5AC:sulfo-LeX), MUC5AC:sulfated sialyl-Lewis A (MUC5AC:sulfo-sLeA), or MUC5AC:sulfated sialyl-Lewis X (MUC5AC:sulfo-sLeX). The one or more glycoforms of the Lewis antigen may be sLeA:sulfo-sLeA and sLeA:sulfo-sLeX; the one or more glycoforms of MUC5AC may be MUC5AC:sLeA, MUC5AC:sLacNAc t1 and MUC5AC:sulfo-sLeX; and the one or more glycoforms of MUC5AC may be MUC5AC:sLacNAc t1t2 and MUC5AC:sulfo-sLeX. Also, the diagnosis may differentiate pancreatic cancer from benign pancreatic disease.

An additional embodiment of the inventive method is combining diagnosing and treating pancreatic cancer in a subject, and this method includes: obtaining a biological sample from the human subject, wherein the biological sample includes one or more glycoforms of a Lewis antigen and one or more glycoforms of MUC5AC; detecting a level of the one or more glycoforms of the Lewis antigen and a level of the one or more glycoforms of the MUC5AC in the biological sample; diagnosing the subject with pancreatic cancer when the one or more glycoforms of the Lewis antigen and the one or more glycoforms of the MUC5AC in the biological sample are at a different level than a statistically validated threshold for the one or more glycoforms of the Lewis antigen and the one or more glycoforms of the MUC5AC; and administering a therapeutically effective amount of a treatment for pancreatic cancer to the diagnosed subject. In some embodiments, the sample may be blood serum; the diagnosis may differentiate pancreatic cancer from benign pancreatic disease; and/or the treatment may be surgically resecting a pancreatic cystic lesion in the subject, applying radiation to the pancreatic cystic lesion, or administering a chemotherapeutic agent to the subject.

A further embodiment is a method of providing medical services for a human patient suspected of having or having pancreatic cancer, including requesting a biological sample from and diagnostic information about the patient, wherein the diagnostic information is a level of one or more glycoforms of a Lewis antigen and a level of one or more glycoforms of MUC5AC; and administering a therapeutically effective amount of a treatment for pancreatic cancer when the diagnostic information indicates that the level of the one or more glycoforms of the Lewis antigen and the one or more glycoforms of MUC5AC in the biological sample are at a different level than a statistically validated threshold for the one or more glycoforms of the Lewis antigen and the one or more glycoforms of MUC5AC. In other aspects, the sample may be blood serum; the diagnosis may differentiate pancreatic cancer from benign pancreatic disease; and/or the treatment may be surgically resecting a pancreatic cystic lesion in the subject, applying radiation to the pancreatic cystic lesion, or administering a chemotherapeutic agent to the subject.

In one embodiment, the present inventive method is monitoring treatment for pancreatic cancer in a human patient, including requesting a first biological sample from and first diagnostic information about the patient, wherein the first diagnostic information is a level of one or more glycoforms of a Lewis antigen and a level of the one or more glycoforms of MUC5AC in the first biological sample; administering a therapeutically effective amount of a treatment for pancreatic cancer to the patient; after administering the therapeutically effective amount of the treatment for pancreatic cancer to the patient, requesting a second biological sample from and second diagnostic information about the patient, wherein the second diagnostic information is a level of the one or more glycoforms of the Lewis antigen and a level of the one or more glycoforms of MUC5AC in the second biological sample; and comparing the first diagnostic information and the second diagnostic information to determine whether the one or more glycoforms of the Lewis antigen and the one or more glycoforms of MUC5AC in the first biological sample are at a different level than the one or more glycoforms of the Lewis antigen and the one or more glycoforms of MUC5AC in the second biological sample. In a further embodiment, the sample may be blood serum.

Another aspect of the inventive method is detecting a level of a glycan in a subject, including obtaining from the subject a biological sample having the glycan; providing a substrate having a capture reagent; exposing the biological sample to the capture reagent to immobilize the glycan in the biological sample on the substrate; providing a detection reagent; exposing the immobilized glycan to the detection reagent to bind the detection reagent to the immobilized glycan; visualizing the bound detection reagent to detect the level of the immobilized glycan; and performing one or both of following steps (a) and (b), wherein step (a) is, before exposing the biological sample to the capture reagent, combining one or more pre-capture enzymes with the biological sample, and wherein step (b) is, before exposing the immobilized glycan to the detection reagent, exposing the immobilized glycan to one or more pre-detection enzymes.

In other aspects of the inventive method for detecting a level of a glycan, the glycan may be sialyl Lewis A; step (a) is performed and the one or more pre-capture enzymes may be PNGaseF, or step (b) is performed and the one or more pre-detection enzymes may be PNGaseF, or steps (a) and (b) both are performed and the one or more pre-capture enzymes may be PNGaseF and the one or more pre-detection enzymes may be PNGaseF; the glycan in the biological sample may be indirectly immobilized on the substrate; the glycan may be part of a glycoprotein or a glycolipid; and/or the glycan may be selected from the group consisting of sialyl Lewis A and sialyl N-acetyl-lactosamine type1.

In further aspects of the inventive method, step (a) is performed and the capture reagent is an anti-Lewis A antibody and the one or more pre-capture enzymes may be sialidase, or wherein step (b) is and the detection reagent is the anti-Lewis A antibody and the one or more pre-detection enzymes may be sialidase, or wherein steps (a) and (b) both are performed and the capture reagent and the detection reagent both may be the anti-Lewis A antibody and the one or more pre-capture enzymes and the one or more pre-detection enzymes both may be sialidase. In other aspects, the anti-Lewis A antibody may be a 7LE antibody; the glycan may be part of a glycoprotein MUC5AC, the capture reagent may be an anti-MUC5AC antibody, step (b) is performed and the detection reagent may be the 7LE antibody, and/or the one or more pre-detection enzymes may be sialydase; and/or the glycan may be sialyl N-acetyl-lactosamine type1.

With additional embodiments of the invention, step (a) is performed and the capture reagent may be an anti-sialyl N-acetyl-lactosamine type1 antibody and the one or more pre-capture enzymes may be sialidase, or step (b) is performed and the detection reagent may be the anti-sialyl N-acetyl-lactosamine type1 antibody and the one or more pre-detection enzymes may be sialidase, or steps (a) and (b) both are performed and the capture reagent and the detection reagent both may be the anti-sialyl N-acetyl-lactosamine type1 antibody and the one or more pre-capture enzymes and the one or more pre-detection enzymes both may be sialidase.

In further aspects of the invention, the anti-sialyl N-acetyl-lactosamine type1 antibody may be a TRA-1-60 antibody or a TRA-1-81 antibody; the glycan may be part of a glycoprotein MUC5AC, the capture reagent may be an anti-MUC5AC antibody, step (b) is performed and the detection reagent may be the TRA-1-60 antibody, and the one or more pre-detection enzymes may be sialydase; the pre-capture enzyme may be sialydase, PNGaseF, or a sulfatase; the pre-detection enzyme may be sialydase, PNGaseF, or a sulfatase; the biological sample may be blood or serum; the substrate may be a microarray slide; and/or the capture reagent may be a glycan binding protein, and/or the detection reagent may be a glycan binding protein.

In another aspect, the inventive method for detecting a level of a glycan also includes, after the biological sample is exposed to the capture reagent, the substrate may be washed to remove any extraneous material that is not immobilized on the substrate. In further aspects of the method for detecting a level of a glycan, the exposing the biological sample to the capture reagent step may include incubating the biological sample on the substrate; and/or the exposing the immobilized glycan to the detection reagent step may include incubating the detection reagent on the substrate. In other aspects, when step (b) is performed, the step of exposing the immobilized glycan to the one or more pre-detection enzymes may include incubating the one or more pre-detection enzymes on the substrate.

Finally, with alternative embodiments of the method for detecting a level of a glycan, the level of the immobilized glycan that is detected may be different than a level of the immobilized glycan that is detected both in the absence of the combining the one or more pre-capture enzymes with the biological sample and in the absence of exposing the immobilized glycan to the one or more pre-detection enzymes; or the level of the immobilized glycan that is detected may be increased as compared to a level of the immobilized glycan that is detected both in the absence of the combining the one or more pre-capture enzymes with the biological sample and in the absence of exposing the immobilized glycan to the one or more pre-detection enzymes.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings, certain embodiment(s) which are presently preferred. It should be understood, however, that the invention is not limited to the precise arrangements and instrumentalities shown.

FIGS. 1A-1C relate to testing of candidate glycans related to sLeA. FIG. 1A shows Lewis antigens with structures similar to sLeA. FIG. 1B shows the reagents used to detect these structures. A filled square indicates specificity for a glycan, and the boxes with thicker borders indicate structures for which the inventors had no detection reagent. FIG. 1C is a cartoon showing antibody-lectin sandwich arrays for parallel testing of candidate biomarkers.

FIG. 2A depicts the structure with sialidase treatment to expose terminal, type 1 N-acetyl-lactosamine. FIG. 2B shows that sialidase treatment of captured MUC16 eliminated the sLeA epitope (left); exposed terminal galactose, as detected by the Bauhinea purpurea lectin (BPL, middle); and did not affect the amount of retained MUC16 (right). FIG. 2C shows that sialidase treatment resulted in increased staining of selected regions of cancer tissue by the TRA-1-60 antibody. FIG. 2D shows that sialidase treatment of captured MUC5AC in a series of plasma samples exposed the TRA-1-60 epitope and resulted in improved discrimination between cancer and control samples.

FIG. 3A shows the discovery cohort. FIG. 3B shows the validation cohort. The inventors observed similar increases in the next set of samples. The receiver-operator characteristic curves showed improvement over sLeA in the discovery cohort (FIG. 3C) and comparable performance in the validation cohort (FIG. 3D).

FIGS. 4A-4C show complementary increases in early-stage and late-stage cancers. FIG. 4A shows the discovery cohort. The rows present data from the indicated capture and detection targets, and the columns represent individual plasma samples. For each biomarker, the inventors set a threshold to provide 1 increase in the control samples. A filled box indicates a measurement greater than the threshold, and an empty box is a measurement below the threshold. Several markers were increased at this high-specificity threshold in both stages I-II and stages III-IV patient samples, including samples without sLeA increases. As shown in FIG. 4B, the validation samples showed similar patterns of increases. FIG. 4C shows two candidate biomarker panels that provided improved performance compared with sLeA in the combined sample sets.

As shown in FIG. 5B, the ROC curves were consistent with previous performance. The MUC5AC glycoform showing type 1 sLacNAc had significantly better performance than sLeA. FIG. 5C shows that at high-specificity thresholds, the patterns of increase were similar to those in the previous cohorts. Several assays were increased in patient samples that were not increased in sLeA. The inventors classified a sample as a case if it showed an increase in at least 1 of the 3 markers (FIG. 5D). The bottom row indicates the classification, where black is a case, and white is a control. The average accuracy of the panel (calculated as correct classifications divided by the number of samples) in 10-fold cross-validation performed 3 times exceeded that of sLeA and any individual marker.

FIG. 6 shows binding specificities of anti-Lewis A (clone 7LE) and anti-sialyl-Lewis A (clone 9L426). The numbers are the relative fluorescence of the indicated lectins binding to the listed glycans, with the glycans grouped by motif. The sLeA motif is given by the text Neu5Aca2-3Galb1-3(Fuca1-4)GlcNAc within the glycan name, or the same text with Neu5Gc substituted for Neu5Ac. 7LE does not bind where sialic acid is present, but it does bind LacNAc type 1 without fucose. Anti-sLeA clone 9L426, on the other hand, mainly binds sLeA, but has weak binding when the fucose is missing. Neither antibody binds sialyl-Lewis X, shown at bottom.

FIG. 7 shows binding specificities of mouse and human E-selectins. Both mouse and human E-selectins bind sLeA and sulfated Lewis A. Only the mouse E-selectin has high binding to sLeX, sulfo-sLeX, and sulfo-LeX (shown at bottom). Human E-selectin can bind disulfated LacNAc type 2 at a high lectin concentration.

FIGS. 8A-8C show validation of mouse E-selectin (mSELE) as a detection reagent. FIG. 8A shows a cell line microarray. The inventors spotted lysates and conditioned media of cell lines known to express sLeA (BxPC3, Capan2, and Su8686) or to not express sLeA (BT20 and HEPG2), and probed the lysates with biotinylated mSELE followed by Cy5-labeled streptavidin. The fluorescence values show binding mainly on the cell lines expressing sLeA. FIG. 8B shows antibody-lectin sandwich arrays. The inventors spotted anti-sLeA, incubated dilutions of a lysate from BxPC3, and probed with mSELE. The fluorescence shows a good response curve with low nonspecific binding at the spot incubated with PBS. FIG. 8C shows validation in immunofluorescence. Cy3-labeled anti-MUC5AC, Cy5-labeled mESEL, and 40,6-diamidino-2-phenylindole were incubated on sections of pancreatic cancer (top) and adjacent control tissue (bottom). E-selectin binding appears on various proteins near the cancer cells, as expected.

FIG. 13A shows PBS controls for all detections (note, ConA detection shows that ConA is not binding to the capture antibody in the PNGase-treated arrays). FIG. 13B shows data from a control study for sialidase activity, cancer high serum sample, CA19-9 detection. FIG. 13C shows data from a control study for sialidase activity, cancer high serum sample, TRA-1-60 detection (note, low signal but the trend holds). FIG. 13D shows a PNGase control study to confirm enzyme activity for a cancer low serum sample, with ConA detection. FIG. 13E shows a PNGase control study to confirm enzyme activity for a control serum sample, with ConA detection. FIG. 13F shows a PNGase control study to confirm enzyme activity for a cancer high serum sample, with ConA detection.

DETAILED DESCRIPTION OF THE INVENTION

Figure 1C:
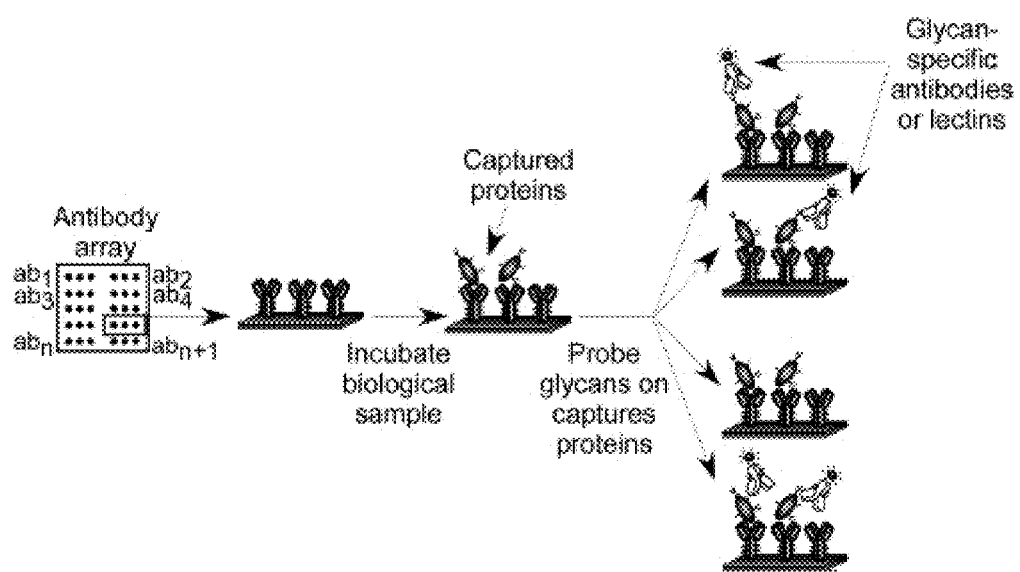

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

All references, patents, patent publications, articles, and databases, referred to in this application are incorporated herein by reference in their entirety, as if each were specifically and individually incorporated herein by reference. Such patents, patent publications, articles, and databases are incorporated for the purpose of describing and disclosing the subject components of the invention that are described in those patents, patent publications, articles, and databases, which components might be used in connection with the presently described invention. The information provided below is not admitted to be prior art to the present invention, but is provided solely to assist the understanding of the reader.

The details of one or more embodiments of the invention are set forth in the accompanying drawings and the description below. Other features, embodiments, and advantages of the invention will be apparent from the description and drawings, and from the claims. The preferred embodiments of the present invention may be understood more readily by reference to the following detailed description of the specific embodiments and the Examples included hereafter.

For clarity of disclosure, and not by way of limitation, the detailed description of the invention is divided into the subsections that follow.

Unless defined otherwise, all technical and scientific terms used herein have the meaning commonly understood by one of ordinary skill in the art to which this invention belongs. Generally, the nomenclature used herein and the laboratory procedures in cell culture, molecular genetics, organic chemistry and nucleic acid chemistry described below are those well-known and commonly employed in the art. Although any methods, devices and materials similar or equivalent to those described herein can be used in the practice or testing of the invention, the inventive methods, devices and materials are now described.

In this specification and the appended claims, the singular forms "a," "an" and "the" include plural reference unless the context clearly dictates otherwise.

As used herein, the term "about" means plus or minus 10% of the numerical value of the number with which it is being used. Therefore, about 50% means in the range of 45%-55%.

As used herein, "administering" or "administered," when used in conjunction with a treatment or a therapeutic, means to administer a treatment or a therapeutic directly to, into or onto a target tissue or to administer a treatment or a therapeutic to a subject whereby the treatment or therapeutic positively impacts the tissue to which it is targeted. "Administering" a composition may be accomplished by oral administration, injection, infusion, absorption or by any method in combination with other known techniques. "Administering" may include the act of self-administration or administration by another person such as a healthcare provider or a device. As used herein, the term "administration" refers to the act of giving or administering a therapeutic treatment (e.g., therapeutic agents for the treatment of pancreatic cancer) to a subject (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intramuscularly, intratumorally, intraperitoneally, etc.) and the like.

As used herein, a "biological sample" means any fluid or other material derived from the body of a normal or diseased subject, such as blood, serum, plasma, lymph, urine, saliva, tears, cerebrospinal fluid, milk, amniotic fluid, bile, ascites fluid, pus, and the like. Also included within the meaning of the term "biological sample" is an organ or tissue extract and culture fluid in which any cells or tissue preparation from a subject has been incubated.

As used herein, the terms "detect" and "detecting" refer to identifying the presence, absence or amount of the object to be detected.

As used herein, the term "detectable moiety" means a label molecule (isotopic or non-isotopic) which is incorporated indirectly or directly into another molecule, wherein the label molecule facilitates the detection of the molecule in which it is incorporated. Thus, "detectable moiety" is used synonymously with "label molecule". Synthesis of labeled molecules can be accomplished by any one of several methods known to those skilled in the art. Label molecules, known to those skilled in the art as being useful for detection, include chemiluminescent, fluorescent or luminescent molecules. Various fluorescent molecules are known in the art which are suitable for incorporation as labels for the methods of the present invention. The protocol for such incorporation may vary depending upon the fluorescent molecule.

As used herein, the terms "diagnosis" or "diagnosing" mean a determination (by one or more individuals) that the cause or nature of a problem, situation, or condition in a subject is pancreatic cancer, or a confirmation of the diagnosis of the disease that includes alternative pancreatic cancer diagnostics, other signs and/or symptoms (e.g., based in whole or in part on the level(s) of the one or more glycans or glycoforms described herein). A "diagnosis" of pancreatic cancer may include a test or an assessment of the degree of disease severity (e.g., "mild," "moderate," or "severe"), current state of disease progression (e.g., stages I-IV of pancreatic cancer), or include a comparative assessment to an earlier diagnosis (e.g., the pancreatic cancer's symptoms are advancing, stable, or in remission). A diagnosis may include a "prognosis," that is, a future prediction of the progression of pancreatic cancer, based on the observed disease state (e.g., based in whole or in part on the different level(s) of the one or more glycoforms or glycans described herein). A diagnosis or prognosis may be based on one or more biological samples obtained from a subject, and may involve a prediction of disease response to a particular treatment or combination of treatments for pancreatic cancer. A diagnosis also can be determination that a subject does not have a benign pancreatic disease (e.g., pancreatitis or benign biliary obstruction) but, instead has pancreatic cancer or is at risk of developing pancreatic cancer.

As used herein, the phrase "differentially present" refers to a difference in the level (quantity and/or the frequency) of a glycan present in samples taken from subjects with pancreatic cancer as compared to samples taken from control subjects, e.g., subjects with a benign pancreatic disease. For example, a glycoform or glycan may be differentially present in that it is present at an elevated level in samples taken from subjects with pancreatic cancer as compared to samples taken from control subjects. A glycoform or glycan can be differentially present in terms of quantity, frequency or both. For the purpose of this invention, a glycoform or glycan is differentially present when there is at least an about a two-fold, preferably at least about a four-fold, more preferably at least about a six-fold, most preferably at least about a ten-fold difference between the level of a given glycoform or glycan in samples taken from subjects with pancreatic cancer as compared to samples taken from control subjects.

As used herein, the term "effective amount" refers to the amount of a composition or a therapy that is sufficient to effect beneficial or desired results. An effective amount can be administered in one or more administrations, applications or dosages and is not intended to be limited to a particular formulation or administration route. An effective amount may include a therapeutically effective amount, or a non-therapeutically effective amount.

As used herein, a "glycan" generally refers to a carbohydrate polymer, for example, N and/or O-glycosidic linkages of monosaccharides that form polysaccharides or oligosaccharides.

As used herein, a "glycan-binding protein" (GBP) is a molecule that recognizes one or more specific glycans. Examples are lectins or are antibodies raised against particular glycan groups. A GBP can be labeled with a tagged with or attached to detectable moiety that can be detected through various types of detection (e.g., radioactive, fluorescent, fluorogenic, chromogenic, or other chemically-labeled tags).

As used herein, a "glycoform" means a glycan, glycoprotein or a glycolipid having a particular glycan composition and/or configuration. For example, a glycoform of the present invention is the glycoprotein MUC5AC, wherein the glycan of MUC5AC is recognized by specific binding to a particular lectin, for example, CCL2, or by specific binding to an antibody to the blood group Lewis A.

As used herein, a "lectin" is a carbohydrate-binding protein.

As used herein, "pancreatic cancer" means a cancer of the pancreas including, but not limited to, malignant pancreatic cancer, mucinous cystic neoplasms and intraductal papillary mucinous neoplasms.

As used herein, the terms "subject" or "patient" generally refer to any living organism and may include, but are not limited to, any human, primate, or non-human mammal in need of diagnosis and/or treatment for a condition, disorder or disease (e.g., pancreatic cancer). A "subject" may or may not be exhibiting the signs, symptoms, or pathology of pancreatic cancer at any stage of any embodiment.

As used herein, the term "therapeutic" means an agent utilized to treat, combat, ameliorate, or prevent, or any combination thereof, an unwanted condition or disease of a subject.

As used herein, the term "therapeutically effective amount" as used herein refers to the amount of treatment (e.g., of an active agent, pharmaceutical compound or composition, or a therapy) that elicits a biological and/or medicinal response in a patient, subject, tissue, or system that is being sought by a researcher, veterinarian, medical doctor or other clinician, or any combination thereof. A biological or medicinal response may include, for example, one or more of the following: (1) preventing a disorder, disease, or condition in an individual that may be predisposed to the disorder, disease, or condition but does not yet experience or display pathology or symptoms of the disorder, disease, or condition, (2) inhibiting a disorder, disease, or condition in an individual that is experiencing or displaying the pathology or symptoms of the disorder, disease, or condition or arresting further development of the pathology and/or symptoms of the disorder, disease, or condition, and/or (3) ameliorating a disorder, disease, or condition in an individual that is experiencing or exhibiting the pathology or symptoms of the disorder, disease, or condition or reversing the pathology and/or symptoms disorder, disease, or condition experienced or exhibited by the individual.

As used herein, the term "treatment" or "treating" as used herein refers to the administration of a therapeutic agent or the performance of a medical or surgical procedure with respect to a subject in need thereof, for either prophylaxis (prevention) or to cure or reduce the extent of or likelihood of occurrence or recurrence of the infirmity or malady or condition or event in the instance where the subject is afflicted. The term "treating" may also be taken to mean prophylaxis of a specific disorder, disease, or condition, alleviation of the symptoms associated with a specific disorder, disease, or condition and/or prevention of the symptoms associated with a specific disorder, disease or condition. In some embodiments, the term refers to slowing the progression of the disorder, disease, or condition or alleviating the symptoms associated with the specific disorder, disease, or condition. In some embodiments, the term refers to alleviating the symptoms associated with the specific disorder, disease, or condition. In some embodiments, the term refers to restoring function which was impaired or lost due to a specific disorder, disease, or condition. As related to the present invention, the term may also mean the administration of medicine or the performance of a medical procedure as a therapy for, as prevention of, or as prophylaxis of pancreatic cancer, e.g., the surgical removal of a pre-malignant precursor lesion or administration of radiation therapy.

As described in greater detail in the Examples, the inventors have identified glycan biomarkers in addition to the CA19-9 Lewis antigen, sLeA, that characterize subgroups of pancreatic cancer patients. Because these glycans do not have identical increases across patients, they can be used in combination, or in a panel of biomarkers, to provide better biomarker performance than any individual marker (including sLeA). The glycans can be divided into 3 structural categories, consisting of sialyl-Lewis X variants, sulfated and/or sialylated sLeA/sLeX variants, and nonfucosylated sialyl-LacNAc type 1. Each category has its own biosynthetic pathways, cell types on which the glycans are shown, and protein receptors, suggesting that the glycans reflect biological subtypes of cancer. Thus, their combined use can have value not only for improved diagnostic accuracy, but also for enhanced information about the disease. Such a capability could meet the need for improved diagnostic accuracy among symptomatic people. Also, the methods of the present invention could be used to address other needs in clinical practice, including surveillance among people with an increased risk for cancer, improving the determining likelihood of rapid progression after surgery, and monitoring the course of the disease after treatment.

In various embodiments, the present invention provides the discovery of diagnostic biomarkers and methods of their use to determine whether a subject has or is at risk of having pancreatic cancer, or whether a pancreatic cyst in a subject may develop or has developed into a malignant mucinous cystic neoplasm or an intraductal papillary mucinous neoplasm, collectively referred to as malignant pancreatic cysts. In one embodiment, the present methods and assays may be used to diagnose, prognose, and treat a cancerous pancreatic lesion in a subject known or suspected of having pancreatic cystic lesion. The inventor has identified several specific glycoforms, including two derived from the mucin glycoprotein MUC5AC. These glycoforms can be specifically identified with appropriate lectins and/or antibodies. In one embodiment, these glycoforms are characterized by specific binding to a particular lectin, for example, CCL2, or to an antibody to the blood group Lewis A.

In one embodiment, the present inventive method for diagnosing pancreatic cancer in a human patient includes: (a) obtaining a biological sample from the human patient, wherein the biological sample includes one or more glycoforms of a Lewis antigen and one or more glycoforms of a mucin 5AC (MUC5AC); (b) detecting a level of the one or more glycoforms of the Lewis antigen and a level of the one or more glycoforms of MUC5AC in the biological sample; and (c) diagnosing the patient with pancreatic cancer when the one or more glycoforms of the Lewis antigen and the one or more glycoforms of MUC5AC are at a different level than a statistically validated threshold for the one or more glycoforms of the Lewis antigen and the one or more glycoforms of MUC5AC.

Methods of obtaining biological samples from a subject suspected of having pancreatic cancer or having pancreatic cancer are well known in the art. In one embodiment, the biological sample is blood drawn from the subject. Given the ease and convenience with which blood samples can be collected and analyzed, diagnosis of pancreatic cancer, and ongoing surveillance for progression or remission of the disease is feasible. In another embodiment, a biological sample is pancreatic cyst fluid obtained from the subject, e.g., by using endoscopic ultrasound (EUS)-guided fine needle aspiration (FNA), or by any common biopsy method commonly used in the field.

In a further embodiment, the biological sample includes one or more glycoforms of a Lewis antigen and one or more glycoforms of a mucin 5AC (MUC5AC). In one embodiment, a glycoform is detected by using a capture reagent to immobilize the glycoform on a substrate and detecting the immobilized glycoform with a detection reagent. The capture reagent may target or bind a first epitope of the glycoform and the detection reagent may target or bind a second epitope of the glycoform (a sandwich assay). As used herein, a glycoform is described by these two epitopes separated by a colon. For example, a glycoform of a mucin MUC5AC glycoprotein that includes a type 1 sialyl-LacNAc glycan is described as "MUC5AC: type 1 sialyl-LacNAc" and is abbreviated as "MUC5AC:sLacNAc t1". In another example, a glycoform of a Lewis A antigen that includes two sialyl-Lewis A epitopes is described as "sialyl-Lewis A:sialyl-Lewis A" and is abbreviated as "sLeA:sLeA". The epitope shown as the first epitope (for the capture reagent) and the epitope shown as the second epitope (for the detection reagent) may be reversed such that the capture reagent is used as the detection reagent, and the detection reagent is used as the capture reagent.

The one or more glycoforms of the Lewis antigen may be sialyl-Lewis A:sialyl-Lewis A (sLeA:sLeA), sialyl-Lewis A:sulfated Lewis A (sLeA:sulfo-LeA), sialyl-Lewis A:sulfated sialyl-Lewis A (sLeA:sulfo-sLeA), sialyl-Lewis A:sialyl-Lewis X (sLeA:sLeX), sialyl-Lewis A:sulfated Lewis X (sLeA:sulfo-LeX), or sialyl-Lewis A:sulfated sialyl-Lewis X (sLeA:sulfo-sLeX).

The one or more glycoforms of the mucin 5AC (MUC5AC) may be MUC5AC:type 1 sialyl-N-acetyl-lactosamine (MUC5AC:sLacNAc t1), MUC5AC:type1type 2 sialyl-N-acetyl-lactosamine (MUC5AC:sLacNAc t1t2), MUC5AC:sialyl-Lewis A (MUC5AC:sLeA), MUC5AC: sialyl-Lewis X (MUC5AC:sLeX), MUC5AC:sulfated-Lewis A (MUC5AC:sulfo-LeA), MUC5AC:sulfated-Lewis X (MUC5AC:sulfo-LeX), MUC5AC:sulfated sialyl-Lewis A (MUC5AC:sulfo-sLeA), or MUC5AC:sulfated sialyl-Lewis X (MUC5AC:sulfo-sLeX).

In another embodiment, the one or more glycoforms of the Lewis antigen are sLeA:sulfo-sLeA and sLeA:sulfo-sLeX. In a further embodiment, the one or more glycoforms of the Lewis antigen are sLeA:sulfo-sLeA and sLeA:sulfo-sLeX and the one or more glycoforms of MUC5AC are MUC5AC:sLeA, MUC5AC:sLacNAc t1 and MUC5AC:sulfo-sLeX. In yet another embodiment, the one or more glycoforms of the Lewis antigen are sLeA:sulfo-sLeA and sLeA:sulfo-sLeX and the one or more glycoforms of MUC5AC are MUC5AC:sLacNAc t1t2 and MUC5AC:sulfo-sLeX.

Mucins, such as MUC5AC, are high molecular weight glycoproteins that are predominantly produced by secretory epithelial cells. The membrane or secretory proteins are major constituents of the mucus layer that protects the gastric epithelium from mechanical and chemical assault. At least 14 genes have been identified as being involved in coding for the several MUC proteins. Mucins have a tandem-repeat domain rich in serine and threonine residues. These residues have numerous potential O-glycosylation sites for the attachment of O-glycan chains that make up to about 80% of the final molecular weight of the glycoprotein.

A representative human amino acid sequence or wild-type human amino acid sequence of Mucin-5AC (MUC5AC) can be found in the National Center for Biotechnology Information (NCBI) databases as XM_003403450.3, XP_003403498.3, GI:410170618.

Previous studies have shown possible origins and functions in cancer of the glycans found in this work. One example is sialyl-LacNAc type 1 (sLacNAc t1), as detected by the TRA-1-60 and 7LE antibodies after desialylation. The target of the TRA-1-60 antibody, the nonsialylated version of the glycan, is an excellent marker for pluripotent stem cells. Previous research found sialyl-LacNAc type 1 on glycolipids in malignant glioma and embryonal carcinoma. Pancreatic cancer cells frequently activate developmental pathways, potentially leading to the expression of the sialyl-LacNAc type 1 epitope. Cancer cells showing sLacNAc t1 may have active sonic hedgehog, notch, or β-catenin pathways.

Sulfated and sialylated Lewis X is found on activated and migrating lymphocytes and are associated with an invasive phenotype in pancreatic cancer. Studies in mice support a role for sLeX in invasion and modulation of immune responses. Both sLeX and sLeA might promote metastasis through interactions with E-selectin receptors, therefore the relative levels of sLeX and sLeA could affect cancer cell behavior, disease progression, and metastasis. Notably, sulfated versions of sLeX have increased affinity for E-selectin receptors.

Any method of detecting a level of (i.e., measuring or quantitating) the glycoforms(s) in the biological sample can be used; whether the glycoforms(s) are assayed individually, in combination, or by high-throughput methods. Preferred methods are reliable, sensitive and specific for a particular glycoform used as a biomarker in aspects of the present invention. The skilled artisan will recognize which detection methods are appropriate based on the sensitivity of the detection method and the abundance of the target glycoform. Depending on the sensitivity of the detection method and the abundance of the target glycoform, amplification may or may not be required prior to detection. One skilled in the art will recognize the detection methods where glycoform amplification is preferred.

In one embodiment, levels of the one or more Lewis antigen glycoforms and the one or more MUC5AC glycoforms are detected with an antibody-lectin sandwich assay or an antibody-antibody sandwich assay. Capture reagents and detection reagents are proteins that will bind to a glycan or to another protein; examples include glycan binding proteins (e.g., antibodies and lectins) as shown in Table 2 below. The capture reagent can be used in the present inventive methods to bind with and immobilize one or more glycans or proteins (in the biological sample) on a support, such as a microarray slide. As known in the art, antibodies can be raised against proteins (e.g., MUC5AC) or carbohydrate structures (e.g., Lewis antigens). In one embodiment, glycan binding proteins (e.g., antibodies and lectins) also are used as detection reagents to detect specific glycans on glycoforms or MUC5AC or Lewis antigens, as shown in Table 2 below.

Lectins have been found in many organisms, including, plants, viruses, microorganisms and animals. Most known lectins are multimeric, with non-covalently associated subunits, and this multimeric structure gives lectins their ability to agglutinate cells or form precipitates with glycoconjugates similar to antigen-antibody interactions. A common characteristic of lectins is that they bind to specifically defined carbohydrate structures. Because of the specificity that each lectin has for a particular carbohydrate structure, even oligosaccharides with identical sugar compositions can be distinguished. Some lectins bind only structures with mannose or glucose residues, while others recognize only galactose residues. Some lectins bind only if a particular sugar is in a terminal non-reducing position in the oligosaccharide, while others bind sugars within the oligosaccharide chain. Further, some lectins do not discriminate when binding to a and b anomers, while other lectins require the correct anomeric structure and a specific sequence of sugars. Thus, the binding affinity between a lectin and its receptor may vary greatly in view of seemingly small changes in the carbohydrate structure of the receptor.

In yet another embodiment of the invention, one or more glycoforms of the Lewis antigen is detected with an E-selectin lectin and one or more glycoforms of MUC5AC is detected with a 7LE anti-Lewis antigen antibody, a TRA-1-60 anti-Lewis antigen antibody, or a *Coprinopsis cinerea* lectin 2 (CCL2).

In a further embodiment, biotinylated detection reagents (e.g., antibodies or lectins), and then Cy5-conjugated streptavidin, are incubated with immobilized glycoforms, followed by scanning for fluorescence and quantification of the resulting images. Additionally, affinity chromatography methods can be used to measure levels of glycoforms. Useful affinity reagents are lectins and antibodies against carbohydrate epitopes. Affinity chromatography methods could be coupled to immunoprecipitation methods to measure various glycoforms. Further descriptions of detection methods are described above and also below in the Examples.

In certain aspects of the present invention, and as otherwise described herein, the detection of a level of a glycoforms includes detecting the level of (e.g., the amount, fluorescence of, or concentration of) one or more of the glycoforms in the biological sample. The one or more glycoforms in the biological sample may be differentially present or at a different level than a statistically validated threshold for the one or more glycoforms. The statistically validated threshold for the level of the specific glycoform(s) is based upon the level of each specific glycoform(s) in comparable control biological samples from a control population, e.g., from subjects that do not have pancreatic cancer, or subjects that have a benign pancreatic disease. Various control populations are described herein. The statistically validated thresholds are related to the values used to characterize the level of the specific glycoform(s) in the biological sample obtained from the subject. Thus, if the level of the glycoform(s) is an absolute value, then the control value is also based upon an absolute value.

The statistically validated thresholds can take a variety of forms. For example, a statistically validated threshold can be a single cut-off value, such as a median or mean. Or, a statistically validated threshold can be divided equally (or unequally) into groups, such as low, medium, and high groups, the low group being individuals least likely to have pancreatic cancer and the high group being individuals most likely to have pancreatic cancer.

Statistically validated thresholds, e.g., mean levels, median levels, or "cut-off" levels, may be established by assaying a large sample of individuals in the select population and using a statistical model such as the predictive value method for selecting a positivity criterion or receiver operator characteristic curve that defines optimum specificity (highest true negative rate) and sensitivity (highest true positive rate). A "cutoff value" may be separately determined for the level of each specific glycoform assayed. Statistically validated thresholds also may be determined according to the methods described in the Examples hereinbelow.

The levels of the assayed glycoform(s) in the patient biological sample may be compared to single control values or to ranges of control values. In one embodiment, specific glycoforms in a biological sample from a patient (e.g., a patient having or suspected of having pancreatic cancer) are differentially present or are at an elevated or reduced level (i.e., at a different level) than the specific glycoforms in comparable control biological samples from subjects that do not have pancreatic cancer when the level of the specific glycoforms in the patient biological sample exceeds a threshold of one and one-half standard deviations above the mean of the concentration as compared to the comparable control biological samples. More preferably, specific glycoforms in a biological sample from a patient (e.g., a patient having or suspected of having pancreatic cancer) are differentially present or are at an elevated or reduced level (i.e., at a different level) than the specific glycoforms in comparable control biological samples from subjects that do not have pancreatic cancer when the level of the specific glycoforms in the patient biological sample exceeds a threshold of two standard deviations above the mean of the concentration as compared to the comparable control biological samples. In another embodiment, specific glycoforms in a biological sample from a patient (e.g., a patient having or suspected of having pancreatic cancer are differentially present or are at an elevated or reduced level (i.e., at a different level) than the specific glycoforms in comparable control biological samples from subjects that do not have pancreatic cancer when the level of the specific glycoforms in the patient biological sample exceeds a threshold of three standard deviations above the mean of the concentration as compared to the comparable control biological samples.

If the level of a specific glycoform(s) in the patient biological sample is present at different levels than their respective statistically validated thresholds, then the patient is more likely to have pancreatic cancer than are individuals with levels comparable to the statistically validated threshold. The extent of the difference between the subject's levels and statistically validated thresholds is also useful for characterizing the extent of the risk and thereby, determining which individuals would most greatly benefit from certain therapies, e.g., surgical resection of a pancreatic cystic lesion in the subject, radiation to a pancreatic cystic lesion, or chemotherapy. In those cases, where the statistically validated threshold ranges are divided into a plurality of groups, such as statistically validated threshold ranges for individuals at high risk of pancreatic cancer, average risk of pancreatic cancer, and low risk of pancreatic cancer, the comparison involves determining into which group the subject's level of the relevant risk predictor falls.

A "reduced level" or an "elevated level" of a glycoforms(s) refer to the amount of expression or concentration of a glycoform in a biological sample from a patient compared to statistically validated thresholds, e.g., the amount of the glycoform in biological sample(s) from individual(s) that do not have pancreatic cancer, have pancreatic cancer (or a particular stage of pancreatic cancer), or have other reference diseases (e.g., a benign pancreatic disease). For example, a glycoform has a "reduced level" in the serum from a subject when the glycoform is present at a lower concentration in the subject's serum sample than in serum from a subject who does not have pancreatic cancer; and a glycoform has an "elevated level" in the serum from a subject when the glycoform is present at a higher concentration in the subject's serum sample than in serum from a subject who does not have pancreatic cancer. For certain glycoforms, elevated levels in a biological sample indicate the presence of or a risk for pancreatic cancer; at the same time, other glycoforms may be present in reduced levels in patients or subjects with pancreatic cancer. In either of these example situations, glycoforms are at a "different level" in pancreatic cancer subjects versus controls.

In one embodiment of the invention, the level of one or more glycoforms of the Lewis antigen and the level of one or more glycoforms of MUC5AC in the biological sample are elevated as compared to the statistically validated thresholds for these glycoforms and the patient is diagnosed with pancreatic cancer. For example, the levels of sLeA:sulfo-sLeA and sLeA:sulfo-sLeX are elevated in the biological sample as compared to the statistically validated thresholds for these glycoforms and the patient is diagnosed with pancreatic cancer. In a further embodiment, the levels of sLeA:sulfo-sLeA, sLeA:sulfo-sLeX, MUC5AC:sLeA, MUC5AC:sLacNAc t1 and MUC5AC:sulfo-sLeX are elevated in the biological sample as compared to the statistically validated thresholds for these glycoforms and the patient is diagnosed with pancreatic cancer. In yet another embodiment, the levels of sLeA:sulfo-sLeA, sLeA:sulfo-sLeX, MUC5AC:sLacNAc t1t2 and MUC5AC:sulfo-sLeX are elevated in the biological sample as compared to the statistically validated thresholds for these glycoforms and the patient is diagnosed with pancreatic cancer.

The differential expression of a particular glycoform indicating a diagnosis or prognosis for pancreatic cancer may be more than, e.g., 1,000,000×, 100,000×, 10,000×, 1000×, 10×, 5×, 2×, 1× a particular statistically validated threshold, or less than, e.g., 0.5×, 0.1×, 0.01×, 0.001×, 0.0001×, 0.000001× a particular statistically validated threshold.

The glycoform biomarker methods of the present invention also can be combined with other diagnostics to improve pancreatic cancer diagnosis and for continued monitoring of the effect of treatment and/or the disease process. In one embodiment, a diagnosis of pancreatic cancer using any of the above-described glycoform biomarker methods can be confirmed with or validated by structural information about the patient's pancreas. For example, the present methods can be performed either before or after imaging of the pancreas by one or more imaging modality, e.g., ultrasound (US), computerized tomography (CT) scanning, or magnetic resonance imaging (MRI). Such imaging may used to detect pancreatic cystic lesions. More or less aggressive treatment can be administered to the patient depending on whether diagnosis using the present biomarker methods is confirmed by one or more of the alternative methods of diagnosis.

The glycan biomarkers of the present invention might be used in combination with other biomarker methods for the detection of resectable and early stage pancreatic cancer. A recent study showed that exosomes coated with the proteoglycan glypican-1 were increased in patients with resectable pancreatic cancer and proteoglycan glypican-1 may represent a viable biomarker for early diagnosis or detection. Considering that the glycan side chains of glypican-1 are important in epithelial function and signaling, the glycans found in the present work also may be on cancer exosomes and could improve the information content of exosome detection. Other promising biomarkers that could be combined with the biomarkers of the present invention include micro-RNAs, DNA, and tumor cells in the circulation; proteins in the urine; and various types of biomarkers in the pancreatic juice or stool, all of which could help define biological subtypes of pancreatic cancer.

In addition to the markers mentioned above, the biomarkers of the present invention could be combined with results from imaging modalities such as endoscopic ultrasound, magnetic resonance imaging, positron emission tomography, or computerized axial tomography. The biomarkers also could be combined with the evaluation of cells or tissue obtained by biopsy or collection from the blood circulation, analyzed by morphological analyses or staining for molecular markers. In addition, the biomarkers of the present invention could be used in conjunction with clinical information, such as age, race, smoking status, body-mass index, diabetic status, lymph node status, family history, disease history, or the presence of metastases. The genetic background of an individual, particularly in regard to genotypes associated with risk for disease, also could be used in combination with the biomarkers of the present invention.

Beyond disease prediction, the present glycoform biomarker methods also can include treating pancreatic cancer in a subject. In addition to any of the detection and diagnostic methods described above, the inventive methods can include administering a therapeutically effective amount of a treatment for pancreatic cancer to the diagnosed subject. That is, the present glycoform biomarker methods can be combined with the treatment of pancreatic cancer, i.e., to indicate the initiation of one or more pancreatic cancer therapies, discontinuation of one or more therapies, or an adjustment to one or more therapies (e.g., an increase or decrease to drug therapy, radiation therapy, and the like). The present glycoform biomarker methods also will allow for early prediction of pancreatic cancer and for targeted therapy to reduce the severity or prevent altogether the development of pancreatic cancer. In response to the diagnosis of pancreatic cancer, in some aspects of the method, a subject may be treated with one or more of pancreatic cancer treatments (e.g., radiation, a drug, a surgery, chemotherapy), or treated with a modification of an existing treatment, modified in response to the diagnosis of pancreatic cancer in that subject.

Another aspect of the invention is a method of providing medical services for a patient suspected of having or having pancreatic cancer, including a physician (or other healthcare professional) requesting a biological sample from and diagnostic information about the patient, wherein the diagnostic information is a level of the one or more glycoforms of a Lewis antigen described above and a level of the one or more glycoforms of MUC5AC described above (in the biological sample); and the physician, or other healthcare professional, administering a therapeutically effective amount of a treatment for pancreatic cancer when the diagnostic information indicates that the level of the one or more glycoforms of a Lewis antigen and the level of one or more glycoforms of MUC5AC in the biological sample are at a different level than a statistically validated threshold for the one or more glycoforms of the Lewis antigen and the one or more glycoforms of MUC5AC.

In some embodiments, the glycoform methods of the present invention can be combined with, and/or used for the selection of, various treatments for pancreatic cancer. Different treatments for pancreatic cancer can be ordered by a physician, or other healthcare provider, for a patient depending on the severity or stage the pancreatic cancer as indicated by the glycoform biomarker methods of the present invention.

In some embodiments, the treatment is administered in a therapeutically effective amount. The therapeutically effective amount will vary depending upon a variety of factors including, but not limited to: the severity of the pancreatic cancer (mild, moderate or severe) or the stage of the pancreatic cancer as indicated by the glycoform biomarker methods; the age, body weight, general health, sex, and diet of the subject; the rate of excretion of any drug; any drug combination; and the mode and time of administration of the treatment.

The glycoform biomarker methods of the present invention also can be combined with, and/or used for the selection and administration of, various medications for the treatment of pancreatic cancer. By using the present glycoform biomarker methods, a physician or other healthcare provide can determine whether medication is needed and, if so, the amount and type of the medication to be administered. Examples of pancreatic cancer medications include, but are not limited to, gemcitabine, abraxane (nanoparticle-bound paclitaxel), fluorouracil (5-FU), or combinations of drugs. The present biomarker methods can provide information on the development of pancreatic cancer and, thus, can be used to guide choice of therapy and/or monitor therapeutic responses in individual cases. Further, if the levels of the present biomarkers indicate that the pancreatic cancer is mild, treatment for the patient then might exclude more toxic therapies.

Accurate prognostication is an important objective in pancreatic cancer patient management to help assure appropriate counseling and to assess the likelihood of significant adverse outcomes, including death. In some aspects, the glycoform levels are used to determine the efficacy of treatment received by a patient for pancreatic cancer, that is, the Lewis antigen and MUC5AC glycoform levels of the patient may be assessed before treatment, and on one or more occasions after the administration of a treatment, to determine whether the treatment is effective. In particular, the present methods for diagnosing and treating also include performing the present methods on multiple occasions, i.e., to monitor the condition of the pancreas or the patient over time. In particular, at one or more moments in time after initially performing the present biomarker methods, the present methods can again be performed and the results compared to results from an earlier-performed use of the present biomarker methods. A treatment for pancreatic cancer can be administered before or after initially performing the present biomarker methods; and the course of treatment can be altered as indicated by the comparison(s). For example, if a pancreatic cancer medication has been administered and, with the passage of time, there is a greater difference between the amount of a biomarker and its control, then a larger dose of the medicament (or surgery) might be indicated.

One embodiment of the present inventive method is the monitoring of treatment for pancreatic cancer in a human patient, comprising: requesting a first biological sample from and first diagnostic information about the patient, wherein the first diagnostic information is a level of one or more glycoforms of Lewis antigen and a level of the one of more glycoforms of MUC5AC in the first biological sample; administering a therapeutically effective amount of a treatment for pancreatic cancer to the patient; after administering the therapeutically effective amount of the treatment for pancreatic cancer to the patient, requesting a second biological sample from and second diagnostic information about the patient, wherein the second diagnostic information is a level of one or more glycoforms of Lewis antigen and a level of the one of more glycoforms of MUC5AC in the second biological sample; and comparing the first diagnostic information and the second diagnostic information to determine whether the level of one or more glycoforms of Lewis antigen and the level of the one of more glycoforms of MUC5AC in the first biological sample is at a different level than the level of the one or more glycoforms of Lewis antigen and the level of the one of more glycoforms of MUC5AC in the second biological sample.

Another embodiment of the present invention is a kit for diagnosing pancreatic cancer. Kits that allow for the targeted measure of one or more glycoforms would reduce both overall cost and turn-around time for a diagnosis of pancreatic cancer.

In one embodiment, a biomarker kit or panel is used to diagnose pancreatic cancer. The kit is configured to detect the level of the one or more glycoforms of Lewis antigen described above and the level of the one of more glycoforms of MUC5AC described above (in a biological sample). The kit for diagnosing pancreatic cancer may include (a) an array of capture reagents for detecting the level of one or more glycoforms of Lewis antigen and the level of the one of more glycoforms of MUC5AC in a biological sample; (b) a container including a detection reagent; and (c) instructions for the method of detection. The kits also may include a container for one or both of a pre-capture enzyme and a pre-detection enzyme.

In another embodiment, the present diagnostic methods and kits are useful for determining if and when medical treatments and therapeutic agents that are targeted at treating pancreatic cancer should or should not be prescribed for an individual patient. Such medical treatments and therapeutic agents are discussed above and/or are known in the art, and will be ordered by or prescribed by a physician (or other healthcare provider) based on results of the inventive method and standard medical practices.

Some embodiments of the present inventive method include detecting a glycan level in a biological sample, whether that glycan is structurally separate, or is combined as a part of a glycoprotein or glycolipid. In one embodiment, the method includes obtaining a biological sample having a glycan; providing a substrate having a capture reagent; exposing the biological sample to the capture reagent to directly or indirectly immobilize the glycan in the biological sample on the substrate; providing a detection reagent; exposing the immobilized glycan to the detection reagent to bind the detection reagent to the immobilized glycan; visualizing the bound detection reagent to detect the level of the immobilized glycan; (a) before exposing the biological sample to the capture reagent, combining one or more pre-capture enzymes with the biological sample, and/or (b) before exposing the immobilized glycan to the detection reagent, exposing the immobilized glycan to one or more pre-detection enzymes.

In one method, antibodies (capture reagents) are spotted on a microarray slide (substrate) followed by the blocking steps. The antibodies also could be spotted in flat-bottom microtiter plates or could be individually coated to the entire well of a microtiter plate. The antibodies also could be attached to beads and used in a suspension format such as that offered in the Luminex platform. Alternatively, however, the antibodies to be spotted could be blocked while in solution, i.e., before the antibodies are spotted on the microarray. This alternate blocking procedure may be useful to pretreat the glycan-detection reagents in case it is desirable to detect more than one glycan in a single assay, using multiple lectins. Since lectins are glycoproteins, they may react with each other when they are used together. Blocking the glycan groups on the lectins would prevent those interactions.

A detection reagent is a molecule that recognizes specific glycans. Examples are lectins or antibodies raised against particular glycan groups. A detection reagent used in the present invention can probe variations in the different glycan structures of glycosylated proteins captured on microarrays. Lectins are valuable glycan affinity reagents used in experimental formats such as affinity chromatography and electrophoresis, detection of blots of separated glycoproteins, and in the capture or detection of proteins in microtiter plates to quantify glycans on specific. Antibodies also have been developed to target and study particular carbohydrates, such as the cancer-associate Thomsen-Friedenreich antigens or, as described herein, the Lewis blood group structures. Other detectable moieties (e.g., tags) and methods of tag detection are known in the art and can be applied to the present invention.

The biological sample can be exposed to the capture reagent on the substrate by, for example, incubating the biological sample on the substrate. As result of exposing the biological sample to the capture reagent, the glycans in the sample can be directly or indirectly immobilized on or attached to the substrate. For example, glycans in the sample can be directly attached to the substrate if the glycan binds to the capture reagent. Further, glycans in the sample can be indirectly attached to the substrate if the glycan is a part of a glycoprotein or a glycolipid, and the protein portion of the glycoprotein or the lipid portion of the glycolipid binds to the capture reagent.

Similar to capture reagents, detection reagents are proteins that will bind to a glycan or to another protein. Examples include antibodies and lectins, as shown in Table 2 below ("detection antibodies and lectins"). One or more detection reagents can be used in the present inventive methods to bind with the glycans in the sample that are directly or indirectly immobilized on or attached to the substrate.

The detection reagents are detectable (visualizable) because they are tagged with a detectable moeity that can be detected through various types of detection. Some of these tags and detection methods include radioactive, fluorescent, fluorogenic, chromogenic, or other chemical labels. Useful radio labels, which are detected by gamma counter, scintillation counter, or auto radiography include 3H, 125I, 131I, 35S, and 14C.

Common fluorescent labels include fluorescein, rhodamine, dansyl, phycoerythrin, phycocyanin, allophycocyanin, o phthaldehyde, and fluoroescamine. The fluorophoor, such as the dansyl group, must be excited by light of a particular wavelength to fluoresce. The protein can also be labeled for detection using fluorescence-emitting metals such as 152Eu, or others of the lanthanide series.

The immobilized glycans can be exposed to one or more detection reagents such that the one or more detection reagents bind to the immobilized glycans. The bound detection reagents are visualized to detect the level of the immobilized glycan. Exemplary methods of visualizing the bound glycans include, for example, two-color rolling circle amplification or resonance-light scattering. In one embodiment, the bound detection reagents are scanned for fluorescence using 633-nm excitation (LS Reloaded).

In one embodiment of the present invention, before exposing the biological sample to the capture reagent, one or more pre-capture enzymes can be combined with the biological sample. For example, the buffer solution that is used to prepare the biological sample can include the one or more pre-capture enzymes. More specifically, the sialyl group on some glycans might interfere with the capture reagent binding to the glycan. A pre-capture enzyme, such as sialidase, can be included when preparing the sample to enzymatically remove the sialyl group and reduce the level of this interference, i.e., increase the amount of glycan that binds to the capture reagent. Similarly, a sulfate group on some glycans might interfere with the capture reagent binding to the glycan. A pre-capture enzyme, such as sulfatase, can be included when preparing the sample to enzymatically remove the sulfate group and reduce the level of this interference. Example sulfatase enzymes would include SULF-1, SULF-2, ARSG (arylsulfatase G), and ARSK (arylsulfatase K), all of which remove sulfates from glycans.

Further, in other embodiments, N-linked glycans in the biological sample interfere with the capture reagent binding to O-linked glycans in the biological sample. In this instance, a pre-capture enzyme, such as a PNGaseF, can be included when preparing the sample to enzymatically remove the N-linked glycans and reduce the level of this interference.

In some embodiments, PNGaseF is added to the buffer (that is used to prepare the biological sample) in a dilution to give a final concentration from about 1000 to about 50000 U/mL. In another embodiment, PNGaseF is added to the buffer in a dilution to give a final concentration from about 2500 to about 40000 U/mL. In further embodiments, PNGaseF is added to the buffer in a dilution to give final concentration of about 2500 U/mL, 5000 U/mL, 10000 U/mL, 20000 U/mL or 40000 U/mL. In yet a further embodiment, after addition of the buffer to the biological sample, the biological sample is incubated at 37° C. for 2 hours. The biological sample also could be incubated for times from 1 hour to 18 hours, at temperatures ranging from room temperature to 37° C.

Similar to the use of pre-capture enzymes to reduce interference, pre-detection enzymes can be used to reduce interference in the binding of the immobilized glycan to the detection reagent. As such, in one embodiment of the present invention, before exposing the immobilized glycan to the detection reagent, the immobilized glycan can be exposed to one or more pre-detection enzymes, e.g., by incubating the immobilized glycan with one or more pre-detection enzymes. Some examples of pre-detection enzymes include sialidase to enzymatically remove the sialyl group from the immobilized glycan, PNGaseF to enzymatically remove N-linked glycans, and a sulfatase to enzymatically remove a sulfate group from the immobilized glycan. In some embodiments, the immobilized glycans are incubated with PNGaseF for two hours at 37° C. at a concentration of 500 U/mL and/or the immobilized glycans are incubated with sialidase at 250 U/mL overnight at 37° C. PNGaseF may be incubated for 2-18 hours at 37 C and concentrations of 500-2500 U/mL, and sialidase may be incubated overnight or at least 18 hours at 37 C and concentrations of 150-500 U/mL.

In some embodiments, pre-capture enzymes are used to reduce interference in the capture reagent binding to the glycan and also pre-detection enzymes are used to reduce interference in the binding of the immobilized glycan to the detection reagent.

EXAMPLES

Without further elaboration, it is believed that one skilled in the art can, using the preceding description, practice the present invention to its fullest extent. The following detailed examples describe how to perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1: Materials and Methods for Examples 2-4

The inventors profiled the levels of multiple glycans and mucin glycoforms in plasma from 200 subjects with either pancreatic cancer or benign pancreatic disease, and the inventors validated selected findings in additional cohorts of 116 and 100 subjects, the latter run with the investigators blinded to diagnoses and including cancers that exclusively were early stage.

Human Plasma and Tissue Samples

All collections took place at the University of Pittsburgh Medical Center after obtaining informed consent from the participants and before any surgical or medical procedures. The donors consisted of patients with pancreatic cancer, pancreatitis, or benign biliary obstruction, and from healthy subjects (Table 1). Resectable cancer included stages I and II, and nonresectable cancer included stages III and IV. The pancreatitis patients were a mixture of chronic and acute, and the healthy subjects had no evidence of pancreatic, biliary, or liver disease. All blood samples (EDTA plasma) were collected according to the standard operating procedure from the Early Detection Research Network and were frozen at −70° C. or colder within 4 hours of time of collection. Aliquots were shipped on dry ice and thawed no more than 3 times before analysis.

TABLE 1

Sample characteristics.

| | n | Age (SD) | % Male |
|---|---|---|---|
| Discovery | | | |
| All Cancer | 108 | 68.1 (9.8) | 48.1 |
| Stage I | 2 | | |

TABLE 1-continued

Sample characteristics.

| | n | Age (SD) | % Male |
|---|---|---|---|
| Stage II | 36 | | |
| Stage III | 32 | | |
| Stage IV | 32 | | |
| Unknown Stage | 6 | | |
| Neuroendocrine Tumor | 0 | | |
| All Control | 91 | 57.5 (15.3) | 49.5 |
| Pancreatitis | 61 | | |
| Benign Stricture | 30 | | |
| Abnormal Imaging | 0 | | |
| p-value* | | <0.05 | NS |
| Test | | | |
| All Cancer | 50 | 66.1 (12.0) | 46.0 |
| Stage I | 3 | | |
| Stage II | 47 | | |
| Stage III | 0 | | |
| Stage IV | 0 | | |
| Unknown Stage | 0 | | |
| Neuroendocrine Tumor | 0 | | |
| All Control | 50 | 59.8 (14.8) | 36.0 |
| Pancreatitis | 30 | | |
| Benign Stricture | 10 | | |
| Abnormal Imaging | 10 | | |
| p-value* | | <0.05 | NS |
| Validation | | | |
| All Cancer | 48 | 65.9 (9.3) | 58.3 |
| Stage I | 0 | | |
| Stage II | 21 | | |
| Stage III | 6 | | |
| Stage IV | 20 | | |
| Unknown Stage | 0 | | |
| Neuroendocrine Tumor | 1 | | |
| All Control | 69 | 54.0 (15.4) | 40.6 |
| Pancreatitis | 12 | | |
| Benign Stricture | 9 | | |
| Abnormal Imaging | 48 | | |
| p-value* | | <0.05 | NS |

*p-value computed based on two-sample t-test for continuous variable (age) and Fisher's exact test for binary variable (gender).

In addition, the Van Andel Research Institute Biospecimen Facility provided formalin-fixed, paraffin-embedded tissue from patients who underwent pancreatic resections at a regional hospital affiliate in Grand Rapids, Mich.

Biological Reagents

The buffers and biological solutions used in the microarray assays included the following: 1× phosphate-buffered saline (PBS)+0.5% or 0.1% Tween-20 (PBST 0.5 or 0.1); 10× sample buffer (1×PBS+1% Tween-20+1% Brij-35; Thermo Scientific, Rockford, IL); 4×IgG blocking cocktail (400 μg/mL each of mouse, sheep, and goat IgG, 800 μg/mL rabbit IgG in 1×PBS, antibodies from Jackson Immunoresearch, West Grove, PA); 10× protease inhibitor (Complete Tablet; Roche Applied Science, Indianapolis, IN); and 2× sample dilution buffer (2× sample buffer+2× protease inhibitor+2×IgG cocktail in 1×PBS).

The antibodies and lectins were acquired from various sources (Table 2). The capture antibodies to be printed onto microarray slides were purified by dialysis (Slide-A-Lyzer; Pierce Biotechnology, Rockford, IL) to 1×PBS and ultracentrifuged. Biotinylation was performed using the EZ-Link-sulfo-NHS-LC-Biotin kit (Pierce Biotechnology) according to the manufacturer's instructions.

TABLE 2

Capture Antibodies and Detection Reagents

| Name | ID | Primary target | Source | Catalog No. |
|---|---|---|---|---|
| Capture antibodies | | | | |
| Anti-MUC1 | CM1 | MUC1 | GeneTex (Irvine, CA) | GTX10114 |
| Anti-MUC16 | X325 | MUC16 | Abcam (Cambridge, MA) | AB10033 |
| Anti-MUC16 (Ab2) | X306 | MUC16 | Novus Biologicals (Littleton, CO) | NB120-10032 |
| Anti-MUC5AC | 45M1 | MUC5AC | ThermoScientific (Waltham, MA) | MS-145-P1ABX |
| Anti-MUC5AC (Ab2) | 2-11M1 | MUC5AC | Affinity BioReagents (Golden, CO) | MA1-35704 |
| Anti-sialyl Lewis A (CA19-9, Ab1) | 9L426 | Sialyl Lewis A | USBio (Salem, MA) | C0075-03A |
| Anti-sialyl Lewis A (CA19-9, Ab2) | 121SLE | Sialyl Lewis A | Abcam | AB3982 |
| Anti-sialyl Lewis X | CSLEX1 | Sialyl Lewis X | BD Pharmingen (San Jose, CA) | 551344 |
| Anti-Lewis X | P12 | Lewis X | Abcam | 3358 |
| Mouse IgG, biotin labeled | N/A | N/A | Jackson ImmunoResearch (West Grove, PA) | 015-000-003 |
| Detection antibodies and lectins | | | | |
| Anti-sialyl Lewis A (CA19-9, Ab1) | 9L426 | Sialyl Lewis A | USBio | C0075-03A |
| TRA-1-60 | TRA-1-60 | Terminal N-acetyl-lactosamine, type 1 | Novus Biologicals | NB100-730 |

TABLE 2-continued

Capture Antibodies and Detection Reagents

| Name | ID | Primary target | Source | Catalog No. |
|---|---|---|---|---|
| Anti-sialyl Lewis X | CSLEX1 | Sialyl Lewis X | BD Pharmingen | 551344 |
| DUPAN2 | DUPAN2 | Sialyl Lewis A and sialyl Lewis C | Dr Hollingsworth (Nebraska) | N/A |
| Recombinant mouse E-selectin/CD62E Fc chimera, CF | ESEL | Sulfated Lewis structure | R&D Systems (Minneapolis, MN) | 575-ES-100 |
| Anti-blood group Lewis A | 7LE | Lewis A and terminal N-acetyl-lactosamine, type 1 | Abcam | ab3967 |
| *Erythrina cristagalli* lectin | ECL | Terminal Galβ | Vector Labs (Burlingame, CA) | BK-3000 |
| *Helix aspersa* agglutinin | HAA | Terminal GlcNAcα, GalNAcα, GalNAcβ | Sigma-Aldrich (St. Louis, MO) | L8764 |
| *Ricinus communis* agglutinin I | RCA-1 | Terminal galactose | Vector Labs | BK-1000 |
| *Ralstonia solanacearum* lectin | RSL | αFucose, all linkages | Recombinant production | N/A |
| *Coprinopsis cinerea* (Inky cap fungus) lectin 2 | CCL2 | Lewis X variants: sialylated, sulfated, internal | Recombinant production | N/A |
| *Sclerotia rolfsii* lectin | SRL | Terminal GlcNAc | Wako (Richmond, VA) | 199-17271 |
| *Bauhinea purpurea* lectin | BPL | Terminal Galβ | Vector Labs | BK-1285 |

Antibody Array Fabrication and Use

The antibody array methods followed those presented earlier, with slight modifications. The inventors printed 48 identical arrays containing various antibodies (Table 2) onto glass microscope slides coated with ultra-thin nitrocellulose (PATH Slides; Grace BioLabs, Bend, OR) using a contact printer (Aushon 2470; Aushon BioSystems, Billerica, MA). The inventors printed 6 replicates of each antibody in randomized positions within each array. After printing, hydrophobic borders were imprinted onto the slides (Slide-Imprinter; The Gel Company, San Francisco, CA) to segregate the arrays and allow for individual sample incubations on each array. The arrays were blocked using 1% bovine serum albumin (BSA) in phosphate-buffered saline (PBS) plus 0.5% Tween-20 for 1 hour at room temperature. The slides were rinsed in 1×PBS plus 0.5% Tween-20, washed in the same buffer for 15 minutes, and dried by brief centrifugation at 160×g, with printed arrays facing outside.

TABLE 3

P Values of the Individual Assays in the Discovery and Validation Cohorts

| Assay | Discovery | Validation |
|---|---|---|
| *sLeA: sulfo/sLeX/sLeA(ESEL)* | 6.06E−14 | 1.81E−04 |
| MUC5AC: sulfo/sLeX/sLeA (ESEL) | 1.30E−11 | 1.44E−05 |
| sLeA: sLeA/sLacNAc t1 (7LE) | 8.62E−11 | 1.04E−06 |
| *MUC5AC: sulfo/sLeX (CCL2)* | 3.66E−10 | 2.80E−05 |
| *MUC5AC: sLeA/sLacNAc t1 (7LE)* | 5.02E−10 | 6.46E−05 |
| sLeX: sulfo/sLeX/sLeA (ESEL) | 9.01E−09 | NS |
| sLeA: sLeA | 1.02E−07 | 2.00E−03 |
| MUC16: sulfo/sLeX/sLeA (ESEL) | 3.54E−07 | 7.58E−04 |
| MUC16: sLeA/sLacNAc t1 (7LE) | 1.17E−06 | 5.09E−04 |
| sLeA(Ab2): sLeA/sLacNAc t1 (7LE) | 5.45E−06 | 6.88E−05 |
| MUC16(Ab2): sulfo/sLeX/sLeA (ESEL) | 9.56E−06 | — |
| LeA: sulfo/sLeX/sLeA (ESEL) | 1.73E−05 | — |
| MUC16: sLeA | 3.29E−05 | 3.83E−02 |
| sLeA(Ab2): sLeA | 3.88E−05 | 6.45E−03 |
| sLeA(Ab2): sLacNAc t1t2 (TRA-1-60) | 5.76E−05 | NS |
| sLeX: sulfo/sLeX (CCL2) | 5.90E−05 | 7.11E−05 |
| LeA: sLacNAc t1t2 (TRA-1-60) | 7.20E−05 | — |
| sLeX: sLeA/sLacNAc t1 (7LE) | 9.54E−05 | 1.22E−03 |
| sLeA: sLacNAc t1t2 (TRA-1-60) | 1.05E−04 | 8.32E−03 |
| MUC5AC(Ab2): sulfo/sLeX/sLeA (ESEL) | 1.46E−04 | — |
| MUC1: sLacNAc t1t2 (TRA-1-60) | 2.44E−04 | — |
| sLeA: sLeX | 3.43E−04 | 5.09E−03 |
| sLeX: sLeX | 3.78E−04 | NS |
| MUC16: sLacNAc t1t2 (TRA-1-60) | 7.66E−04 | 1.46E−02 |
| MUC16: sulfo/sLeX (CCL2) | 8.75E−04 | 5.78E−03 |
| sLeA: sulfo/sLeX (CCL2) | 1.19E−03 | 1.86E−04 |
| *MUC5AC: sLacNAc t1t2 (TRA-1-60)* | *1.21E−03* | *4.93E−02* |
| LeA: sLeX | 4.59E−03 | — |
| MUC5AC(Ab2): sLacNAc t1t2 (TRA-1-60) | 1.23E−02 | — |
| sLeX: sLacNAc t1t2 (TRA-1-60) | 1.81E−02 | NS |
| sLeA(Ab2): sLeX | 3.42E−02 | NS |
| LeX: sLacNAc t1t2 (TRA-1-60) | 3.79E−02 | — |
| LeX: sulfo/sLeX/sLeA (ESEL) | 4.90E−02 | — |

The assays that were in the biomarker panels are shown in italics, and the CA19-9 assay (capture and detection sLeA) is shown in bold.

The plasma samples were diluted 2-fold into phosphate-buffered saline (PBS) containing 0.1% Tween-20, 0.1% Brij-35, an IgG blocking cocktail (200 µg/mL mouse and rabbit IgG and 100 µg/mL goat and sheep IgG; Jackson ImmunoResearch), and protease inhibitor (Complete Mini EDTA-free Tablet, Roche Applied Science). The inventors applied 6 µL of each plasma sample to each array and let the sample incubate overnight at 4° C. Each unique sample was applied to 3 separate arrays. The arrays were washed in 3 changes of PBS/0.1% Tween-20 for 3 minutes each and dried by centrifugation (Eppendorf 5810R, Hauppauge, NY rotor A-4-62, 1500×g for 3 minutes), and a biotinylated lectin or antibody was incubated on the arrays for 1 hour at room temperature. The lectins and antibodies were prepared at 3 µg/mL in PBS with 0.1% BSA and 0.1% Tween-20, except for the anti-LeA (clone 7LE) antibody, which was at 15 µg/mL. For *Coprinopsis cinerea* lectin 2 (CCL2) detection, the inventors pre-incubated the CCL2 with Cy5-conjugated streptavidin at a 4:1 molar ratio as described.

After washing and drying the arrays as described earlier, Cy5-conjugated streptavidin (Roche Applied Science) prepared at 2 µg/mL in PBS with 0.1% BSA and 0.1% Tween-20 was incubated for 1 hour at room temperature, followed by a final wash and dry. The arrays detected with precomplexed CCL2/streptavidin required only a final wash and dry. The inventors scanned the slides for fluorescence using 633-nm excitation (LS Reloaded; Tecan, San Jose, CA).

The resulting images were quantified using in-house software written in Matlab (version R2014a; Mathworks, Natick, MA). A custom script was used to remove any outliers from the 6 replicate spots according to the Grubbs test. The script calculates the Grubbs statistic for the spot farthest from the mean of the replicates and rejects the spot if the Grubbs statistic exceeds a preset threshold, using P<0.1 here. The script repeatedly removes spots until no outliers remain or to a minimum of 4 spots. It then calculates the geometric mean of the remaining replicate spots as the final output for each array.

The program also averages values between replicate arrays and reports the associated coefficient of variation. The inventors repeated assays for measurements that had a CV greater than 0.4 for signals in the quantifiable response range of the assay (determined by dilution series of pooled samples).

Statistics and Analysis Methods

To characterize classification performance of individual biomarkers, nonparametric estimates of the receiver operating characteristic (ROC) curves were generated. Performance of each biomarker was compared with cancer antigen 19-9 (CA19-9) based on the area under the ROC curve (AUC). In particular, a nonparametric bootstrap procedure stratified on case and control status was performed with 500 bootstrap samples. Two-sided P values for testing the equivalence in AUC between a pair of biomarkers were computed based on a Wald test and bootstrap estimated standard error. Also reported were 95% confidence intervals of the difference in AUC based on bootstrap samples. All statistical calculations were performed using R program R-3.2.2 (https://cran.r-project.org/).

Marker panels were selected using the Marker State Space method with 10-fold cross-validation to select individual markers. The program limits the initial size of panels to 3 markers, with the option of adding markers iteratively.

Immunohistochemistry with Sialidase Treatment

The inventors used automated staining (Ventana Discovery Ultra) to perform immunohistochemistry (IHC) on sections cut from formalin-fixed, paraffin-embedded blocks. The inventors performed antigen retrieval using the Ventana CC1 buffer for 36 minutes at 95° C. For the slides treated with sialidase, the inventors incubated a 1:200 dilution of sialidase (α2-3,6,8 Neuraminidase, NEB P0720L, 50,000 U/mL) in 1× GlycoBuffer (5 mmol/L $CaCl_2$, 50 mmol/L pH 5.5 sodium acetate) overnight at 37° C. The control slides received only the 1× GlycoBuffer under the same conditions. The slides then were incubated with the TRA-1-60 antibody (NB100-730, Novus Biologicals, 500 ig/mL diluted at 1:100) for 1 hour at RT, followed by the secondary antibody (Ventana Umap HRP-conjugated anti-mouse) for 12 minutes at 37° C. The development step used the diaminobenzadine chromagen according to preset parameters in the Ventana platform.

Glycan Array Analysis

The glycan synthesis and array core facility of the Consortium for Functional Glycomics (CFG) performed the glycan array experiments and the primary analysis according to the methods presented previously. The inventors downloaded data from the functionalglycomics.org website that previously had been obtained using lectins and glycan-binding antibodies supplied by various investigators. In addition, the inventors sent the recombinant version of CCL2 with biotinylation at the C-terminus to the CFG core facility for processing on their glycan array version 5.2. For detailed analyses of the datasets, the inventors used the GlycoSearch analysis program, and for mining glycan array data to find particular lectins, the inventors used the GlycanBinder database, which derives information from the CFG website.

Cross-Validation

The inventors performed 10-folded cross validation 3 times on each individual marker and on the panel, using the MSS program described herein. The program divides samples randomly into 10 groups; uses the samples from 9 groups to define optimal thresholds for discriminating cases from controls; and applies the thresholds to the remaining group to determine the accuracy of discrimination (calculated as the number of correct classifications divided by the total number of samples). The program repeats the process for each possible group of 9 (10 times in all), calculating an accuracy for each split and for each marker. For each marker, the accuracy was averaged over the 10 splits and over 3 repeats of the 10-fold cross validation.

Example 2: Candidate Glycan Biomarkers for sLeA-Low Cancers

Several glycans are structurally similar to sLeA (FIG. 1A), including variants of sialyl-Lewis X, which the inventors previously showed was increased in a subset of pancreatic cancer patients. To test for increases of glycans, the inventors acquired lectins and antibodies targeting the glycans (FIG. 1B and Table 2). Glycan array data were helpful for determining the specificities of the reagents. Some bind only 1 motif with high specificity, but others bind more, such as the 7LE antibody, which binds both Lewis A and nonfucosylated LacNAc type 1 (FIG. 6). The mouse E-selectin protein binds sLeA, sLeX, and sulfo-sLeX (FIG. 7), and the inventors validated its use as a detection reagent using cell line and tissue specimens (FIG. 8). The inventors previously showed that CCL2 is specific for glycans with 3' fucose, mainly Lewis X variants including sulfated Lewis X.

Each plasma sample was incubated on a microarray of antibodies targeting various mucins and glycans and then the glycans were probed on the captured material with a glycan-binding antibody or lectin. Each sample was incubated on multiple arrays, with each array receiving a different detection reagent (FIG. 1C).

Figure 2A:
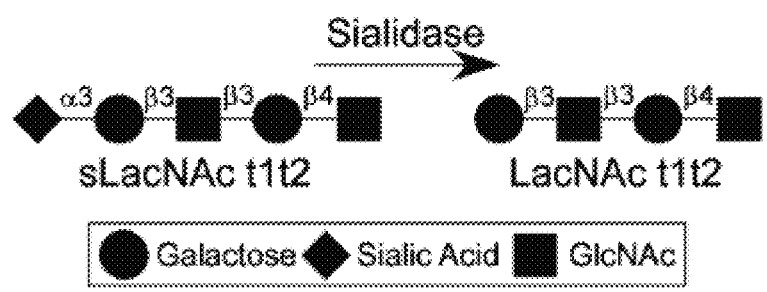
FIGS. 2A-2D relate to using sialidase to expose underlying glycans.
Figure 2B:
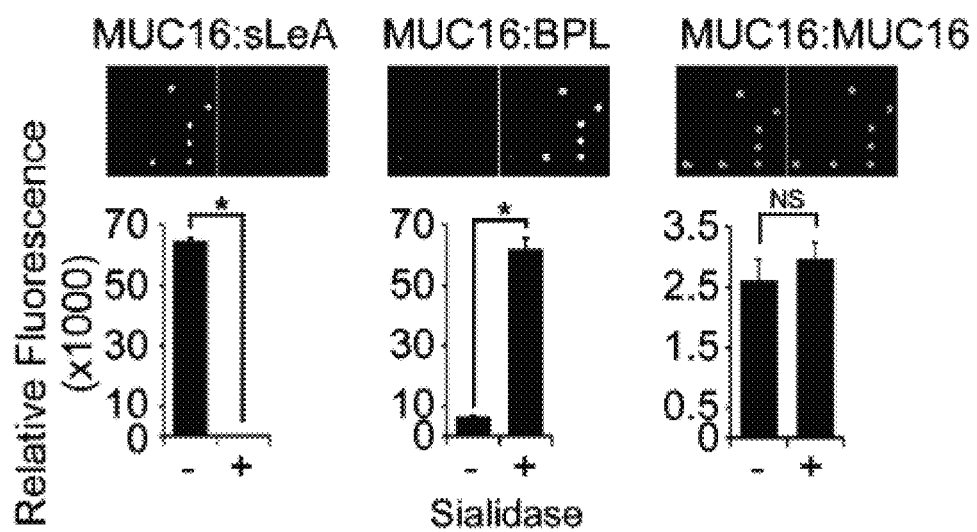
Figure 2C:
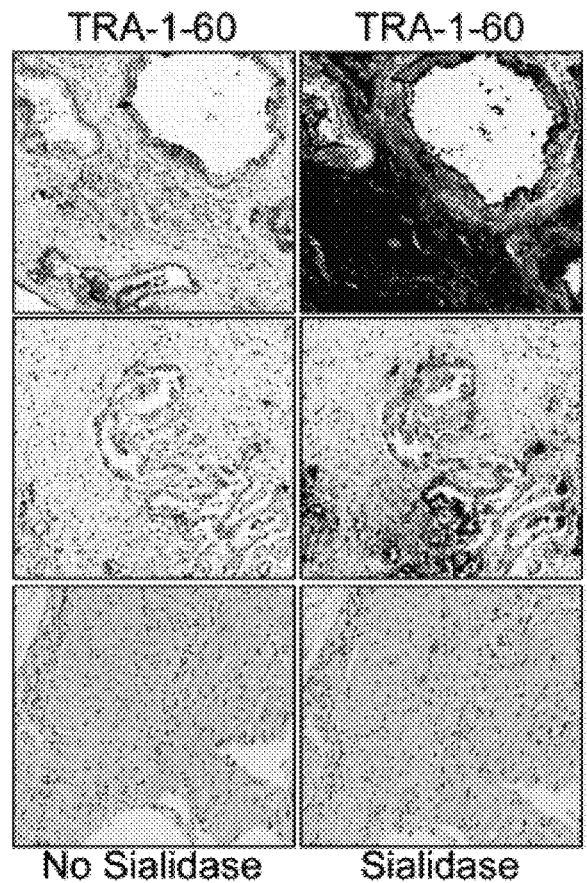
Figure 2D:
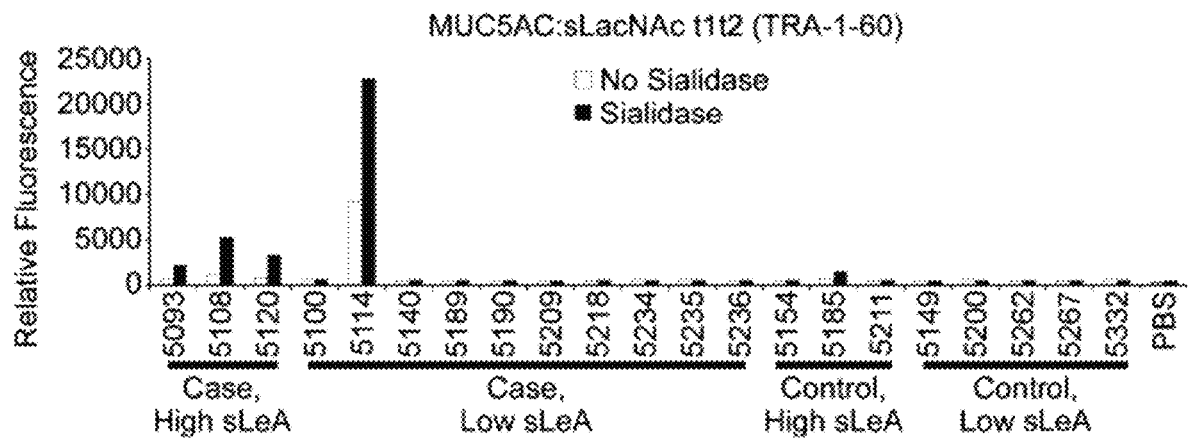

The inventors did not have a reagent to optimally detect sialylated, nonfucosylated, type 1 N-acetyl-lactosamine structures (Siaα2,3Galβ1,3GlcNAcβ1-). There are, however, two antibodies, named "TRA-1-60" and "7LE" (FIG. 1B), with good affinity to the nonsialylated variant. The inventors therefore tested the use of sialidase to remove sialic acid before detecting with the antibodies (FIG. 2A). The inventors confirmed the ability to remove sialic acid on a captured glycoprotein and detect the underlying structure using a protein mixture with a high level of Mucin16 showing the sLeA glycan (FIG. 2B). The staining of tumor tissue in the regions of cancerous epithelia increased upon sialidase treatment (FIG. 2D), and the differentiation of cases from controls in a set of plasma samples was enhanced after enzyme treatment (FIG. 2C). Therefore, in subsequent experiments the inventors used sialidase treatment before detection using the TRA-1-60 and 7LE antibodies.

The inventors acquired measurements of candidate biomarkers in 3 sample cohorts, comprising discovery, validation, and test sets (Table 1). Each measurement consisted of a capture reagent (e.g., antibody) and a detection reagent; so with 9 capture antibodies and 12 detection reagents (Table 2), the inventors acquired 108 unique measurements of capture/detection pairs.

Figure 3A:
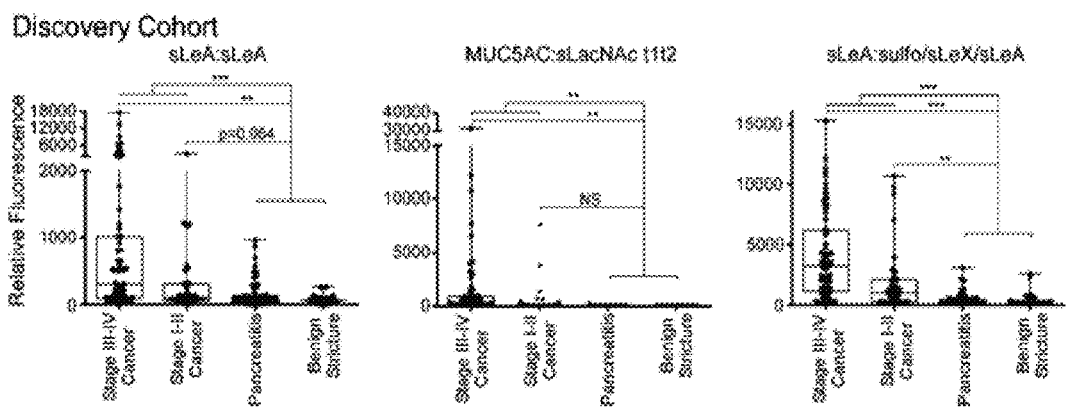
FIGS. 3A-3D show novel glycan biomarkers of pancreatic cancer. The heading of each graph indicates the capture and detection targets, separated by a colon. A glycoform of MUC5AC showing type 1 sialyl-LacNAc (detected by TRA-1-60 after desialylation) and a sandwich assay of sLeA capture and sulfated and/or sialylated sLeA/sLeX detection (detected by mouse E-selectin) showed significant increases in cancer.
Figure 3B:
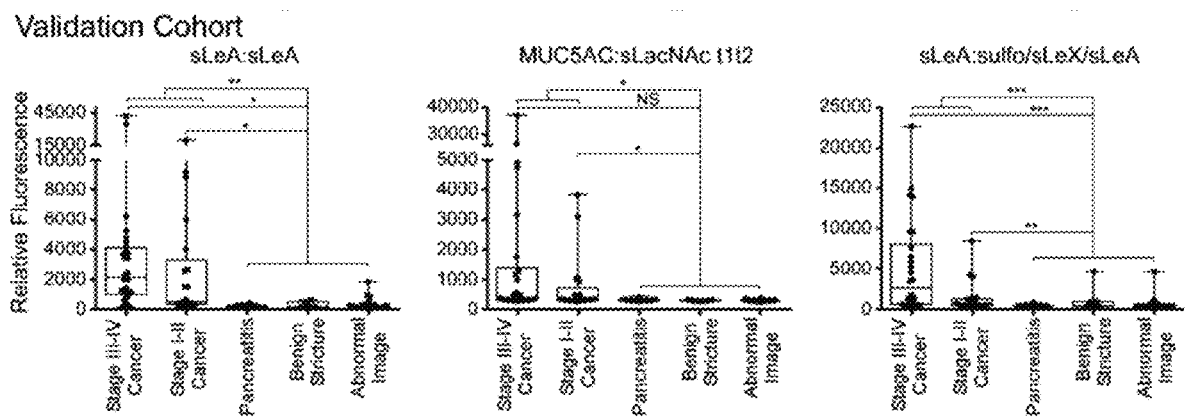
Figure 3C:
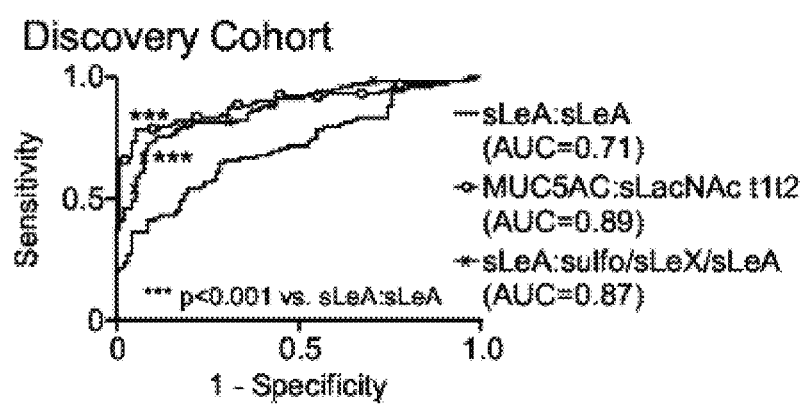
Figure 3D:
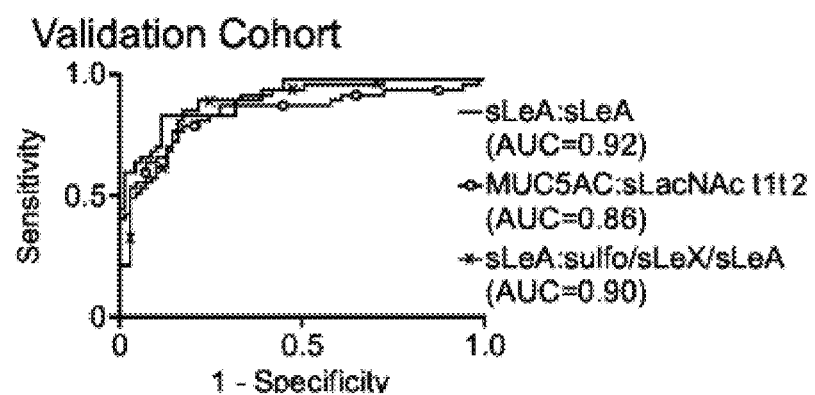

In the discovery cohort, 34 individual biomarkers had significant increases (Table 3). Representative markers included 2 distinct glycoforms of MUC5AC, one showing type 1 sialyl-LacNAc, and the other showing sulfated and/or sialylated sLeA/sLeX (FIG. 3A). The inventors tested a reduced set of 5 capture antibodies and 5 detection reagents (25 unique assays) in the validation cohort and observed significant increases in 19 (Table 3), including the glycoforms of MUC5AC (FIG. 3B). The markers mentioned earlier showed significant improvement in AUC over sLeA in the discovery set (FIG. 3C). The classification performance of sLeA in the validation set (FIG. 3D) was higher than in previous studies. A recent definitive characterization of CA19-9 showed an AUC of 0.77 for discriminating pancreatic cancer from chronic pancreatitis, with lower performance when including benign biliary obstruction, so the inventors viewed the performance in the validation set as an aberration.

Because the cancer patients tended to be older than the control subjects (Table 1), the inventors tested associations with age for each marker within the cancer patients and within the control subjects. None showed an association with age except for the sLeA sandwich (the standard CA19-9 assay), with moderate significance (Table 4). Thus, the markers examined here were not increased as a consequence of age.

TABLE 4

Associations between marker levels and age within patient groups.

| Cohort | Young cancer patients vs old | Young control patients vs old |
| --- | --- | --- |
| Discovery | | |
| MUC5AC: sLacNAc t1t2 (TRA-1-60) | NS | NS |
| sLeA: sulfo/sLeX/sLeA (ESEL) | NS | NS |
| MUC5AC: sulfo/sLeX (CCL2) | NS | NS |
| MUC5AC: sLeA/sLacNAc t1 (7LE) | NS | NS |
| sLeA: sLeA | NS | NS |
| Validation | | |
| MUC5AC: sLacNAc t1t2 (TRA-1-60) | NS | NS |
| sLeA: sulfo/sLeX/sLeA (ESEL) | NS | NS |
| MUC5AC: sulfo/sLeX (CCL2) | NS | NS |

TABLE 4-continued

Associations between marker levels and age within patient groups.

| Cohort | Young cancer patients vs old | Young control patients vs old |
| --- | --- | --- |
| MUC5AC: sLeA/sLacNAc t1 (7LE) | NS | NS |
| sLeA: sLeA Test | NS | NS |
| MUC5AC: sLacNAc t1t2 (TRA-1-60) | NS | NS |
| sLeA: sulfo/sLeX/sLeA (ESEL) | NS | NS |
| MUC5AC: sulfo/sLeX (CCL2) | NS | NS |
| MUC5AC: sLeA/sLacNAc t1 (7LE) | NS | NS |
| sLeA: sLeA | NS | P < .05 (higher in older patients) |

Within either just the cancers or just the controls, the inventors divided the subjects by age, with the oldest third in one group and the youngest third in another group. The inventors then compared the levels of each marker between the groups. Only the one comparison showed a statistical difference.

Example 3: Complementary Increases in the Markers

Figure 4A:
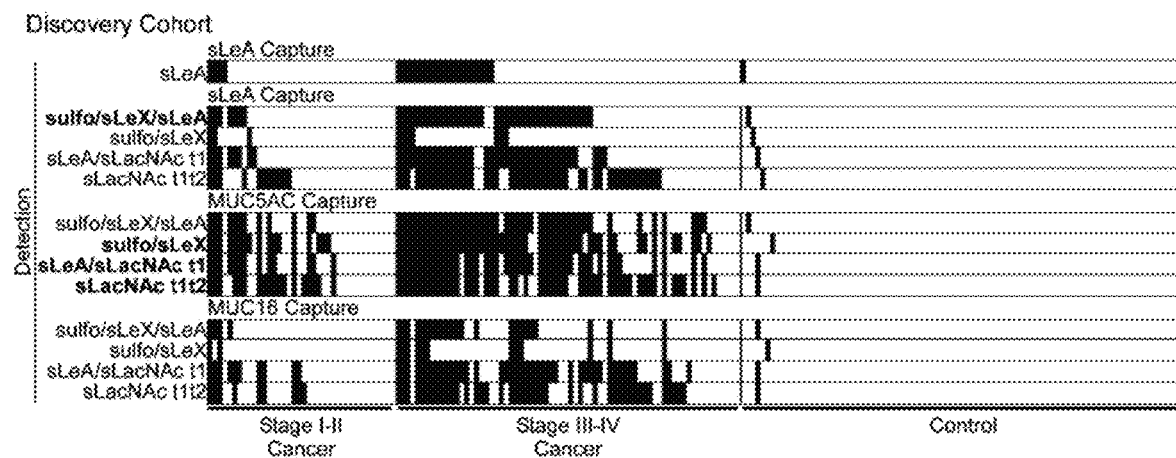
Figure 4B:
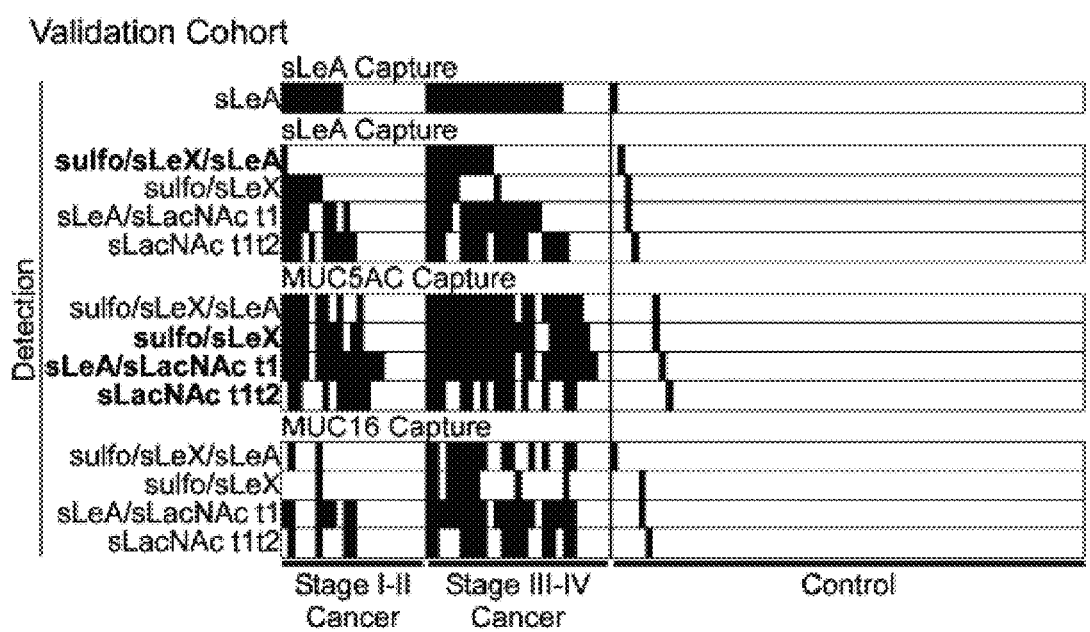

The inventors next tested whether the individual markers provided complementary information to sialyl-Lewis A (sLeA) and to one another—that is, whether they showed increases in distinct subsets of patients and few increases in the controls. For each marker, the inventors set a threshold to provide one false-positive increase, thus providing a view of increases that were specific to cancer. At such a threshold, CA19-9 was increased in only 22% of the cases in the discovery cohort. In contrast, several other markers showed a greater percentage of increases in the stages I-II and stages III-IV cancers, with differences between the markers in the patients with increases (FIG. 4A). The trends were similar in the validation cohort (FIG. 4B). These results suggested that the markers have increases in distinct groups of patients, independent of stage.

The results also suggested that a biomarker panel would perform better than any individual marker. By using all 316 samples from the combined discovery and validation cohorts, the inventors found that a panel of 3 markers provided better sensitivity and specificity than sLeA (FIG. 4C). The panel (panel 1) consisted of a glycoform of MUC5AC showing sulfated- and sialyl-Lewis X (detected by CCL2); another glycoform of MUC5AC showing sialyl-LacNAc type 1 and sLeA (detected by the 7LE antibody after desialylation); and a sandwich assay consisting of the capture of sLeA and the detection of sulfated and/or sialylated sLeA/sLeX (detected by mouse E-selectin). An alternate panel (panel 2) differed by 1 marker. The marker selection program did not choose sLeA for inclusion in the panel, indicating that sLeA at best provided only marginal additional diagnostic information beyond what already was detected by the 3 markers. A notable feature of the panel is that it contains 3 classes of glycans: Lewis X variants, Lewis A/X variants, and sialylated type 1 N-acetyl-lactosamine.

Example 4: Testing the Marker Panel in Blinded Samples

The inventors applied the marker panels to a new, blinded set of 100 samples (i.e., the test set), consisting of stages I-II cancer cases and patients with benign pancreatic diseases.

Figure 5A:
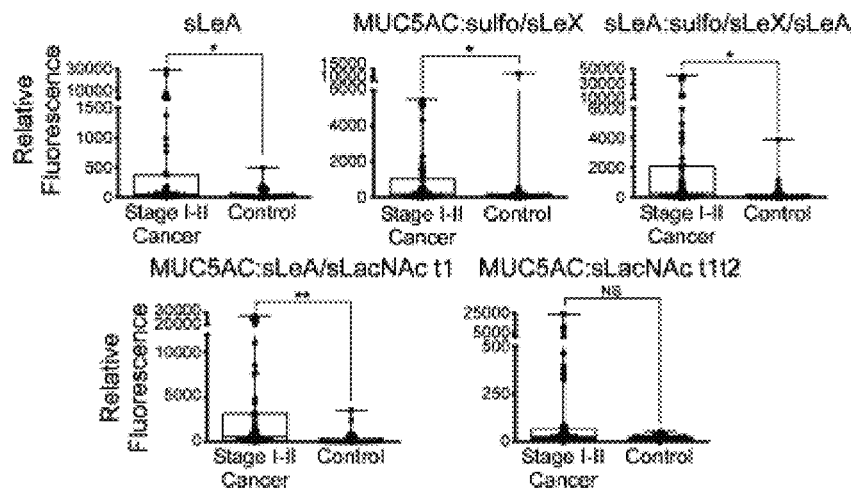
FIGS. 5A-5D show blinded testing of the individual and combined biomarkers. The individual assays showed increases similar to those observed in the previous cohorts (FIG. 5A).
Figure 5B:
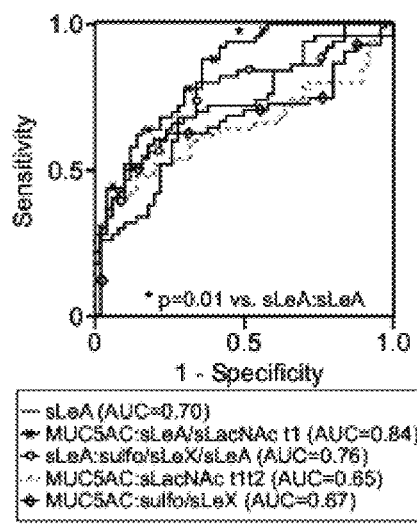
Figure 5C:
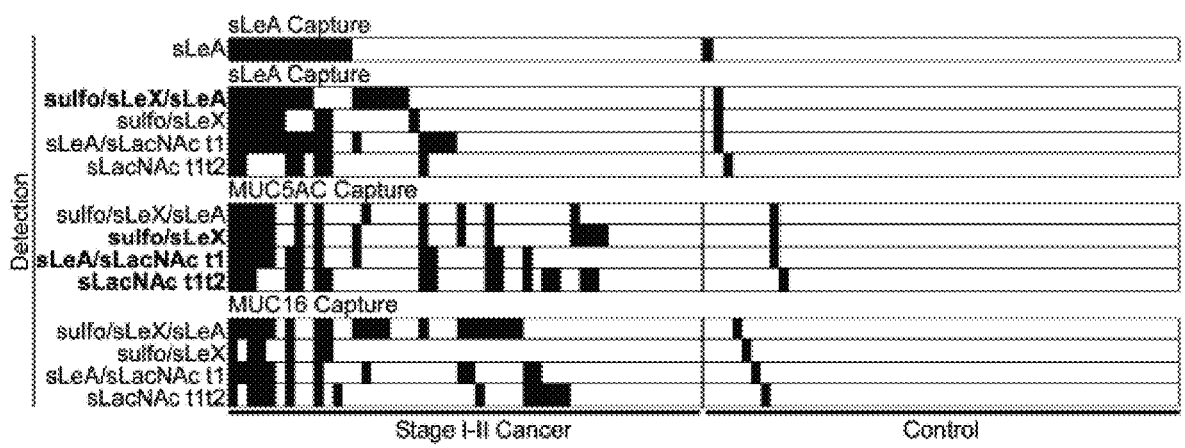

The individual markers had robust and specific increases in cancer (FIG. 5A), and the ROC curve for a MUC5AC glycoform was improved significantly compared with sLeA (with an improvement in AUC of 0.14; 95% confidence interval, 0.04-0.26) (FIG. 5B). Furthermore, the relationships between the markers were similar to the previous sets; increases in the new markers occurred in patients who did not have sLeA increases (FIG. 5C). These observations confirmed the cancer-associated increases of the new biomarkers and their independent contributions to the patterns of increase.

Figure 5D:
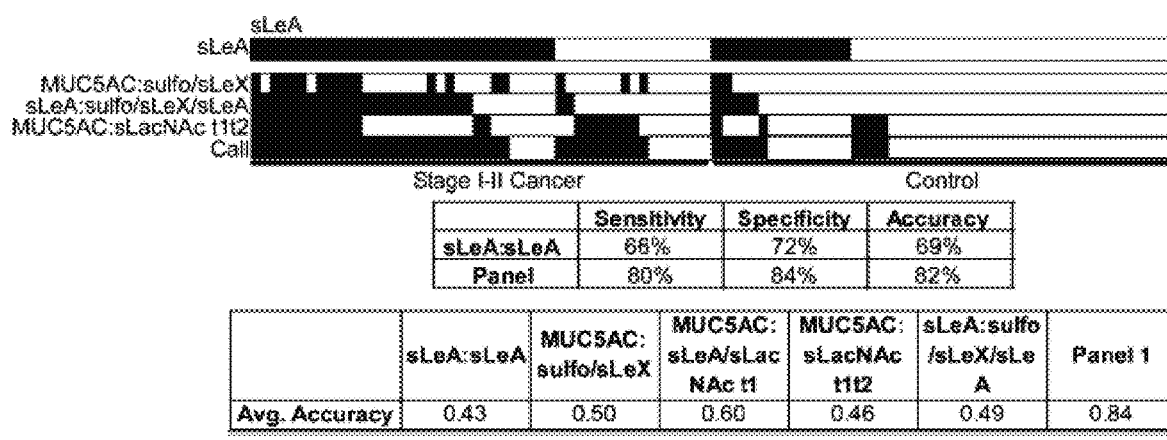

In the blinded application of the panels to classify the samples, both panels 1 and 2 had higher sensitivity than sLeA, but without statistically significant improvement in overall performance (Table 5). The inventors reasoned that the thresholds defining increases for each individual marker were not set optimally, owing to the limited number of samples used for training. When the inventors adjusted the thresholds, while keeping the classification rule the same, the accuracy was 82% for panel 1 compared with 69% for sLeA at its best threshold. All 3 markers of the panel showed increases in cancer patient samples that were not increased in sLeA even at the lower sLeA threshold (FIG. 5D). Furthermore, in 10-fold cross-validation averaged over 3 trials, the average accuracy of the panel was 84%, whereas the average accuracy of the individual markers ranged from 43% to 60% (FIG. 5D). The inventors concluded from these analyses that each of the new biomarkers was increased independently of sLeA at least in some patients, and that together they formed a biomarker panel with improved accuracy compared with sLeA.

inhibitor, and 2×IgG cocktail (referred to as 2× sample dilution buffer). The plasma or serum samples are diluted 2-fold into the sample buffer and incubated overnight at 4° C. with gentle agitation to allow for blocking of non-specific binding to the added IgG in the sample buffer. The next day, the slides are blocked with 1% bovine plasma albumin (BSA, Fisher Scientific, Fair Lawn, NJ) in PBST0.5 for 1 hour, washed in three changes of PBST0.5 for 3 min each, and dried by brief centrifugation at 160×g. We incubate 6 µL of each diluted sample on an array for 2 hours at room temperature, or overnight at 4° C. for larger experiments, and we applied each sample to 3 replicate arrays. After sample incubation, the slides are washed three times in PBST0.1 and spin-dried. We prepare biotinylated lectins or antibodies (the detection reagents) at 3 µg/mL in 0.1% BSA/PBST0.1. The inventors incubate each detection reagent solution on an array for 1 hour, wash and dry each array as described above, incubate each array with Cy5-conjugated streptavidin (43-4316, Invitrogen, Carlsbad, CA) at 2 µg/ml in 0.1% BSA/PBST0.1 for 1 hour, and perform a final wash and dry of the slides. Lastly, the slides are scanned for fluorescence at 633 nm using a microarray scanner (LS Reloaded, TECAN, Morrisville, NC). In the new protocol, the inventors captured the CA19-9 epitope according to their standard protocol; but before probing the captured material with the detection antibody, they treated the captured material with an enzyme PNGaseF. The captured material was treated with PNGaseF to remove N-linked glycans from proteins. The CA19-9 epitope appears primarily on O-linked glycans. PNGase F (P0704L, New England Biolabs) prepared at 500 U/mL in the buffer

TABLE 5

Performance of the Panels and sLeA in Blinded Samples

| Panel | Sensitivity | P value | Specificity | P value | (Sen + Spe)/2 | P value |
|---|---|---|---|---|---|---|
| sLeA:sLeA | 0.54 (0.40-0.67) | | 0.84 (0.71-0.92) | | 0.69 (0.60-0.77) | |
| Panel 1 | 0.66 (0.52-0.78)NS | | 0.80 (0.67-0.89)NS | | 0.73 (0.64-0.81)NS | |
| Panel 2 | 0.72 (0.58-0.83).02 | | 0.70 (0.56-0.81) | .06 | 0.71 (0.61-0.79)NS | |
| sLeA:sLeA | .66 | | .72 | .69 | | |
| Panel 1 | .80 | | .84 | .82 | | |
| Panel 2 | .76 | | .80 | .78 | | |

Top: performance based on the blinded classification;
middle: P value of comparisons between the panels and the CA19-9 assay (capture and detection of sLeA);
bottom: performance after adjusting the thresholds of the individual markers.

Example 5: Materials and Methods for Example 6

The inventors performed the CA19-9 assay on a set of serum specimens using both the standard protocol and a new protocol. The standard protocol involves capturing a CA19-9 epitope out of a biological solution using an immobilized CA19-9 capture antibody, and then probing the captured material with another CA19-9 (detection) antibody. The standard protocol uses the following steps. The buffers and biological solutions used in the microarray assays are: 1× phosphate-buffered saline with 0.5% or 0.1% Tween-20 (referred to as PBST0.5 or PBST0.1); 1×PBS with 1% Tween-20 and 1% Brij-35 (Thermo Scientific, Rockford, IL) (referred to as 10× sample buffer); 1×PBS with 400 µg/mL each of mouse, sheep, and goat IgG, and 800 µg/mL rabbit IgG (antibodies from Jackson Immunoresearch) (referred to as 4×IgG blocking cocktail); 1×PBS with 1 tablet protease inhibitor (Complete Tablet, Roche Applied Science, Indianapolis, IN) per 1 mL PBS (referred to as 10× protease inhibitor); and 1×PBS with 2× sample buffer, 2× protease provided by the manufacturer was incubated at 37° C. for 2 hours on the slides. The slides were washed five times in PBST0.1 for 3 min per wash and then dried by centrifugation. The rest of the protocol followed the standard protocol.

Example 6: Removing N-Glycans Leads to Increased CA19 Signal

Figure 9:
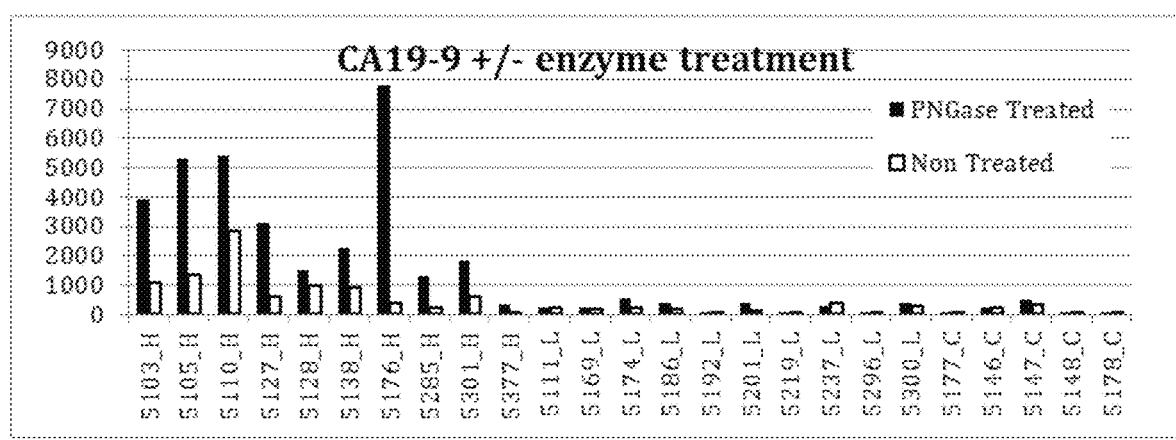
FIG. 9 shows enhancement of CA19-9 detection with PNGase enzyme treatment that occurs after glycoprotein capture and before glycan detection. The numbers on the x-axis are the IDs of individual samples, followed by a letter indicating the sample type: H indicates cancer samples with high CA19-9 (based on previous measurements), L indicates cancer samples with low CA19-9, and C indicates non-cancer control samples.

By removing the N-linked glycans, the CA19-9 detection antibody was better able to access the CA19-9 epitope, leading to an increased CA19-9 signal (see, FIG. 9). Specifically, the CA19-9 signals were much higher for many of the cancer samples. For example, there was a greater than 10-fold enhancement for sample 5176. Importantly, by removing the N-linked glycans, some of the low-CA19-9 cancer samples were in a more detectable range. As such, an increased percentage of cancer samples can be detected with this method. Similar to the improved detection of the TRA-1-60 epitope after treatment with sialidase, treatment with the enzyme PNGaseF better exposes the CA19-9, making it more detectable by the CA19-9 detection antibody.

Example 7: Materials and Methods for Example 8

Antibody arrays were produced with the capture antibodies anti-MUC5AC, anti-MUC16, and CA19-9. The antibodies anti-MUC5AC and anti-MUC16 target MUC5AC and MUC16, respectively; and the antibody CA19-9 targets the glycan sialyl-Lewis A (sLeA). The sLeA glycan is attached to several distinct glycoproteins, so the captured material is heterogeneous. The inventors assayed twelve serum samples: six samples from pancreatic cancer patients that had high levels of CA19-9 (as determined in a previous experiment), three samples from pancreatic cancer patients with low levels of CA19-9, and three samples from control subjects having a benign pancreatic disease and low levels of CA19-9.

Each serum sample was incubated on multiple replicate arrays using the inventors' standard sample preparation protocol (diluting each serum sample 2-fold into a 2× sample buffer consisting of PBS, detergent, and blocking antibodies and standard serum incubation protocol (for 2 hours at room temperature). After washing the slides, each array was incubated with PNGaseF (to remove N-linked glycans) for two hours at 37° C. at a concentration of 500 U/mL. The arrays that were to be detected with TRA-160 also were incubated with sialidase (to expose the epitope of the TRA-1-60 antibody) at 250 U/mL overnight at 30° C. After washing the slides, each array was incubated with a biotinylated detection antibody, either TRA-1-60 or CA19-9.

Example 8: Removing N-glycans Leads to Increased Detection by CA19-9 and TRA-1-60

Figure 10A:
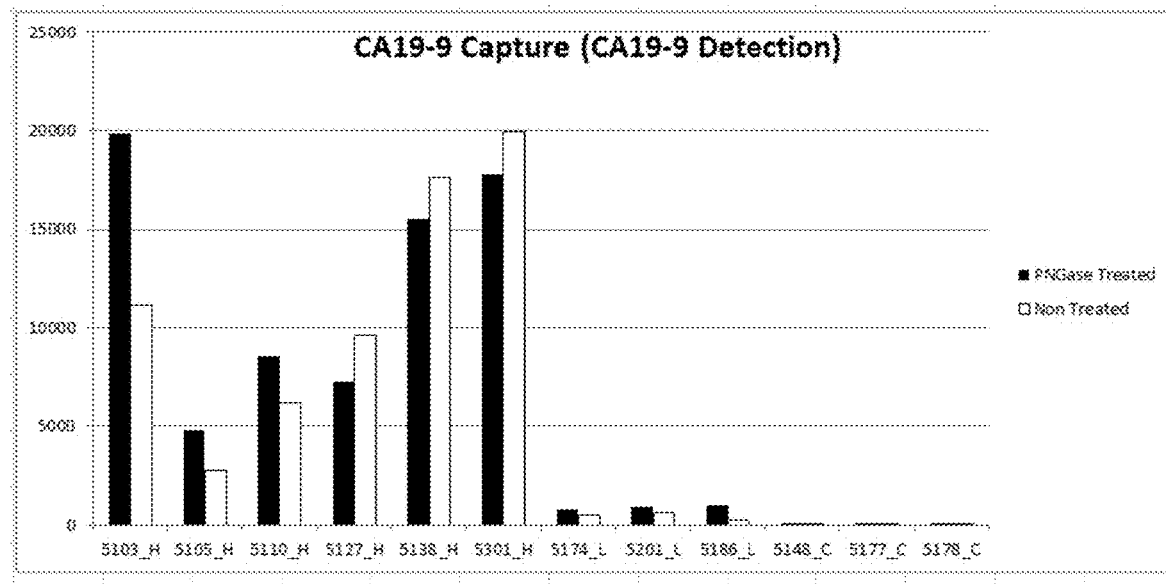
FIGS. 10A-C show detection by anti-sialyl Lewis A (CA19-9) of sialyl Lewis A in captured CA19-9 (FIG. 10A), MUC5AC glycoprotein (FIG. 10B), and MUC16 glycoprotein (FIG. 10C), with or without PNGaseF treatment that occurs after glycoprotein capture and before glycan detection. In the labels along the x-axis of the graphs, the number refers to a de-identified code for a sample, and the letter after the number refers to the types of sample: H for a cancer sample with high CA19-9, L for a cancer sample with low CA19-9, and C for a control sample with a benign pancreatic disease and low CA19-9.
Figure 10B:
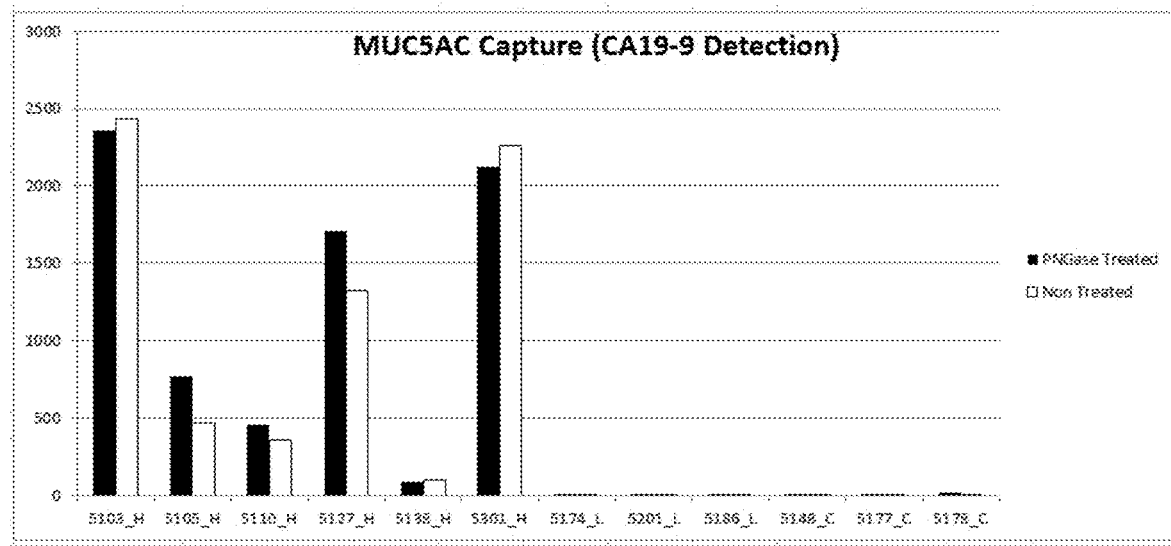
Figure 10C:
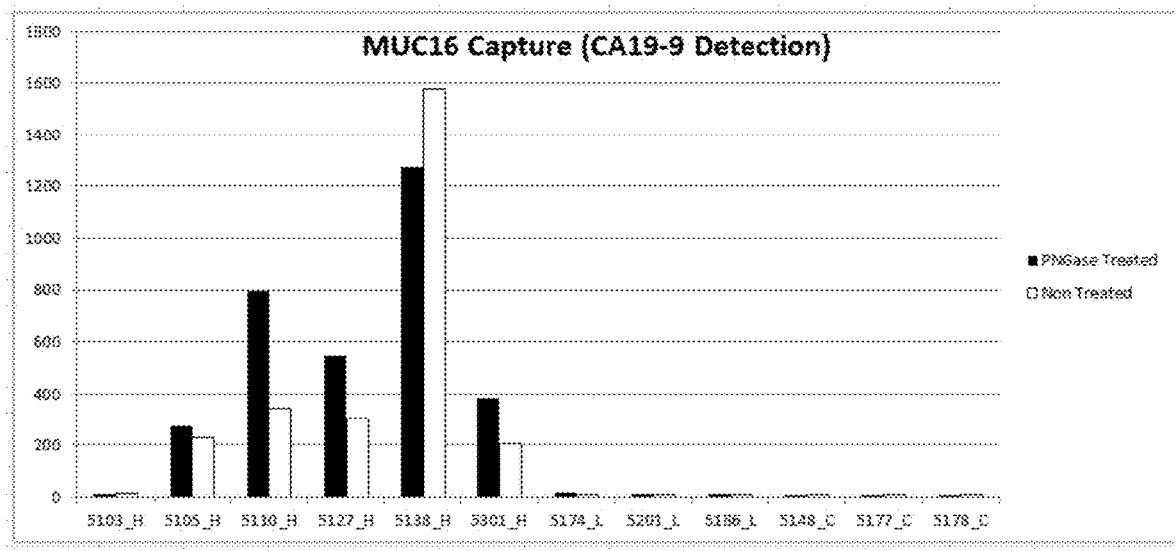

For arrays detected with CA19-9 (FIGS. 10A-C), the most benefit is seen with glycoproteins captured with CA19-9 (FIG. 10A). Sample 5103, from a cancer patient that had high levels of CA19-9, shows a major increase with PNGaseF treatment and, importantly, the samples with low CA19-9 also show good increases of about two-fold each. The control samples show no detectable increase. Thus, the samples with low CA9-9 are more easily detectable using PNGaseF treatment.

Figure 11A:
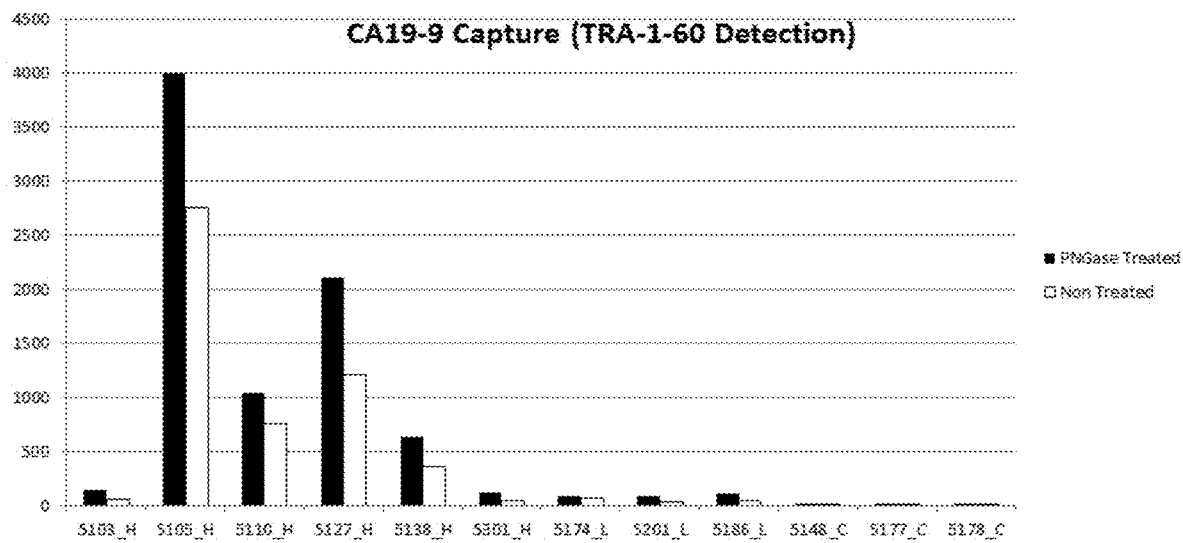
FIGS. 11A-C show detection by TRA-1-60 of terminal N-acetyl-lactosamine, type 1, in captured CA19-9 (FIG. 11A), MUC5AC glycoprotein (FIG. 11B), and MUC16 glycoprotein (FIG. 11C), with a sialidase treatment that occurs after glycoprotein capture and before glycan detection, and with or without a PNGaseF treatment that occurs after glycoprotein capture and before glycan detection. In the labels along the x-axis of the graphs, the number refers to a de-identified code for a sample, and the letter after the number refers to the types of sample: H for a cancer sample with high CA19-9, L for a cancer sample with low CA19-9, and C for a control sample with a benign pancreatic disease and low CA19-9.
Figure 11B:
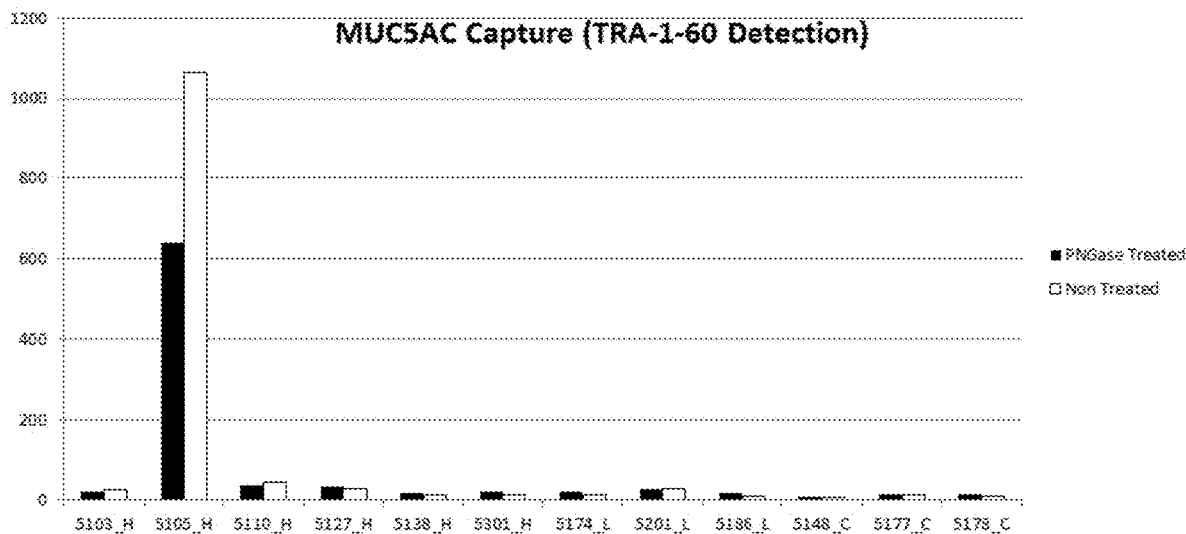
Figure 11C:
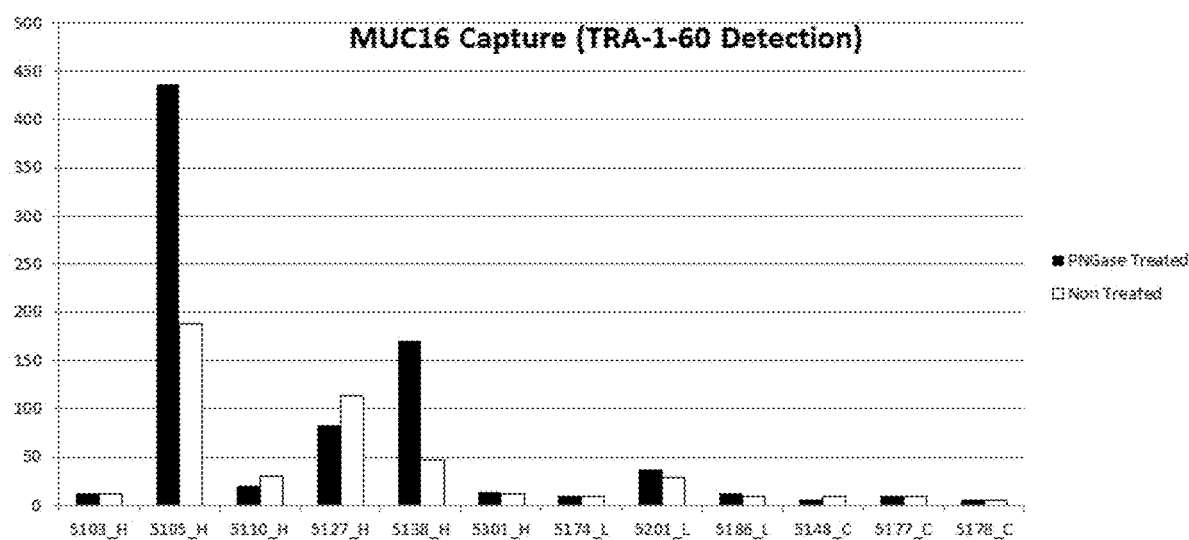

For the arrays detected with TRA-1-60 (FIGS. 11A-C), consistent increases were observed in combination with CA19-9 capture (FIG. 11A). Every cancer sample showed substantial increases, including those with low CA19-9.

For both detection reagents (CA19-9 and TRA-1-60), selected samples showed increases with the MUC16 capture antibody, but no benefit from PNGaseF treatment was observed with the MUC5AC capture antibody.

Example 9: Materials and Methods for Example 10

Based on the results described in Examples 6 and 8 above, the inventors believed that a benefit could be achieved by treating the serum samples with PNGaseF before the glycoproteins were captured (sample pre-treatment). That is, because removal of N-glycans after capturing with CA19-9 improved detection by the CA19-9 detection antibody, capture by CA19-9 should be improved by removing N-glycans prior to the capture of the glycoproteins.

Serum samples were diluted two-fold into a 2× sample buffer (standard) consisting of PBS, detergent, and blocking antibodies. PNGaseF was added to the sample buffer in a series of dilutions to give final concentrations of 2500, 5000, 10000, 20000, and 40000 U/mL. After addition of the sample buffer to the samples, the samples were incubated at 37° C. for 2 hours. Control samples received standard buffer and were otherwise treated identically to the test samples. The samples were incubated on arrays and detected with the CA9-9 antibody according to the inventors' standard protocol.

Additionally, the inventors assayed serum samples using the sample pre-treatment (describe in the preceding paragraph) combined with the PNGaseF treatment that occurred after glycoprotein capture and before glycan detection (post-treatment). The method for post-treatment was the same as described in Examples 5 and 7 above. The inventors tested three samples: one pancreatic cancer sample with high CA19-9, one pancreatic cancer sample with low CA19-9, and a control sample with a benign pancreatic disease and low CA9-9.

Figure 12A:
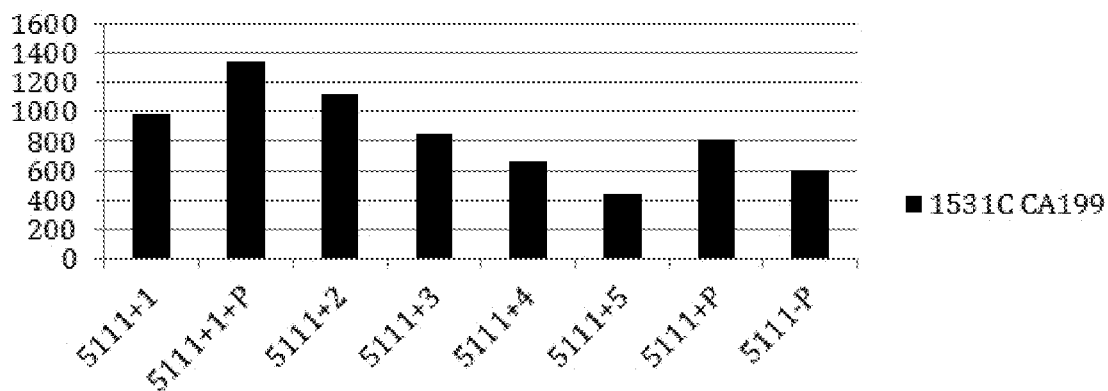
FIGS. 12A-C show a comparison of PNGaseF pre-treatment, post-treatment, and a combination of PNGaseF pre-treatment and post-treatment for a cancer sample with low CA19-9 FIG. 12A), for a control sample with a benign pancreatic disease and low CA19-9 (FIG. 12B), and for a cancer sample with high CA19-9 (FIG. 12C). The x-axis gives the sample ID followed by the condition. The conditions are: "+1" is pre-treatment, 40000 U/mL; "+2" is pre-treatment, 20000 U/mL; "+3" is pre-treatment, 10000 U/mL; "+4" is pre-treatment, 5000 U/mL; "+5" is pre-treatment, 2500 U/mL; "+1+P" is pre-treatment at 40000 U/mL plus post-treatment; "+P" is post-treatment only; and "−P" is no PNGaseF (standard).

Example 10: Increased Detection by Combining Pre-Treatment and Post-Treatment The signals for the low CA19-9 cancer sample (sample 5111) were consistently higher with serum pre-treatment than the standard condition or with post-treatment alone (FIG. 12A). The combination of pre-treatment and post-treatment gave the highest signal. These results demonstrate a benefit for pre-treatment of the sample with PNGaseF for capture and detection using the CA19-9 antibody, as well as a further benefit from subsequent post-treatment of the array.

Figure 12B:
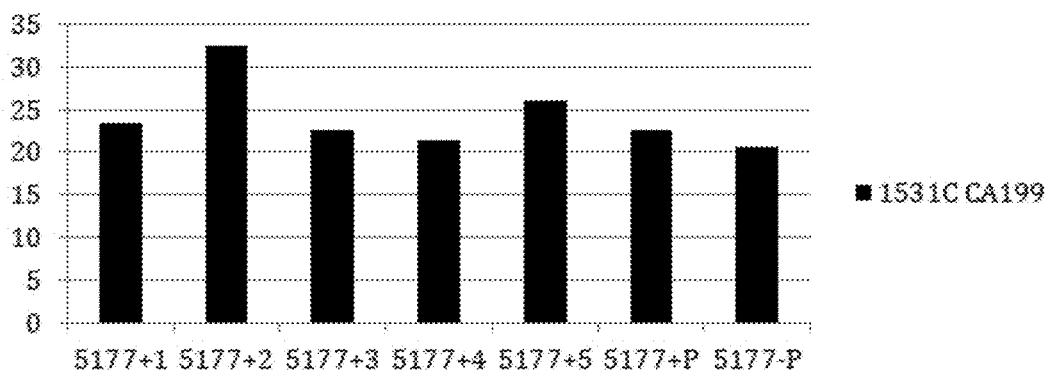
Figure 12C:
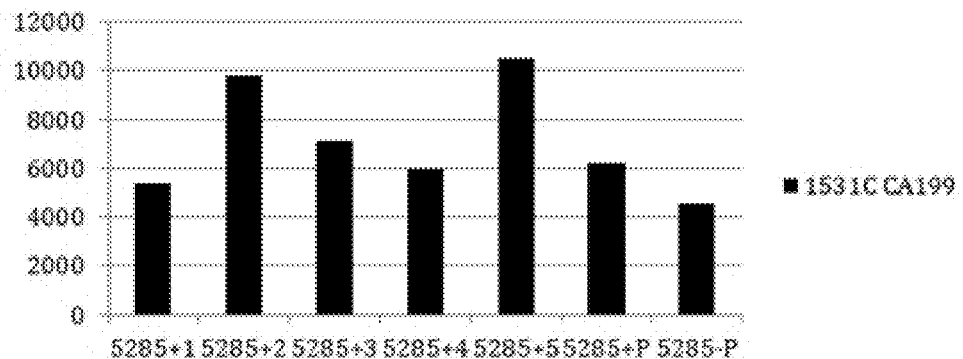

The control sample (5177) showed no consistent increase (FIG. 12B). The high CA19-9 cancer sample showed higher signals than the standard condition but inconsistent increases of pre-treatment relative to post-treatment (FIG. 12C). The lack of consistent increase could reflect incomplete enzyme reactions due to the high starting concentrations, but overall the result shows that pre-treatment of the sample is increasing the exposure and capturing of the CA19-9 antigen.

Example 11: Experimental Controls

Figure 13A:
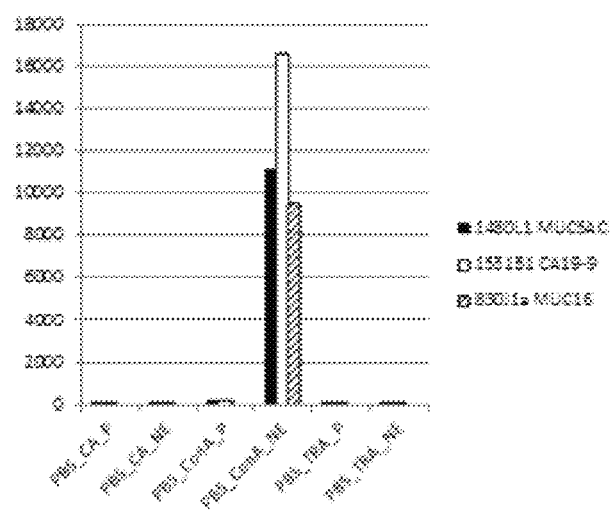
FIGS. 13A-13F show data that confirms no binding of the detection reagents directly to the capture antibodies and that confirms the activity of the enzymes. The y-axis is the fluorescence signal at a capture antibody, and each bar represents a particular type of capture antibody as indicated by the legend. Each set of bars is data from a distinct condition: P=PNGase Treatment; NE=No Enzyme Treatment; S=Sialidase Treatment; and SP=Sialidase & PNGase Treatment. The label under each set of bars indicates the sample incubated, the detection reagent, and the treatment condition. For example, "PBS_CA_P" was incubated with PBS buffer, detected with CA19-9 antibody, with PNGaseF treatment of the captured material.

As shown in FIGS. 13A-13-F, the inventors conducted further experiments to confirm that there was no binding of the detection reagents directly to the capture antibodies; and to confirm activities of the enzymes.

As shown in FIG. 13A, there was negligible binding of the detection reagents CA19-9, ConA, and TRA-1-60 to the capture antibodies. ConA, which is essentially a control for the PNGase, binds the antibodies in the absence of PNGaseF treatment, owing to the presence of N-linked glycans on antibodies, but PNGaseF treatment eliminates the binding. The other detection reagents do not bind even in the absence of PNGaseF treatment. An important part of this control is ConA; the two detection conditions show that PNGase pretreatment effectively prevents ConA binding to the capture antibodies.

Figure 13B:
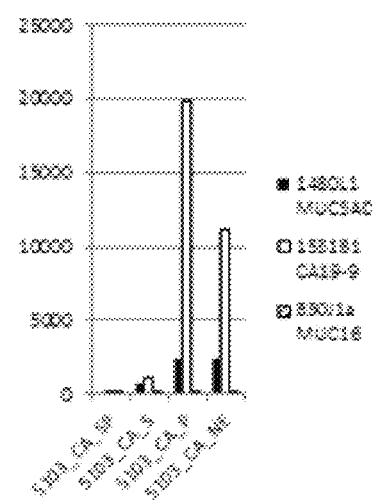
Figure 13C:
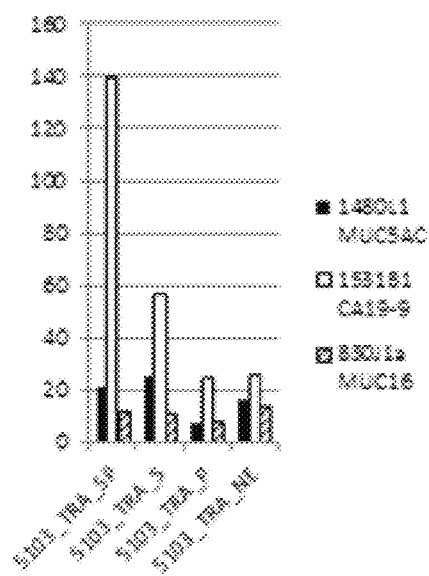

The experimental data shown in FIG. 13B, validates the activity of sialidase by showing that the CA19-9 signal was reduced with sialidase treatment, and that the TRA-1-60 signal was increased with sialidase (for the same cancer Hhgh serum sample). A serum sample with high CA19-9 was incubated on the array, the captured material was treated with one of the four conditions shown, and the array was probed with CA19-9. CA19-9 binding requires sialic acid. Its level was high in the absence of sialidase but low with sialidase treatment. The experimental data shown in FIG. 13C also validates the activity of sialidase, even though the signal is lower. TRA-1-60 binding requires no sialidase. The inventors saw that TRA-1-60 binding was very low without sialidase but increased with it.

Figure 13D:
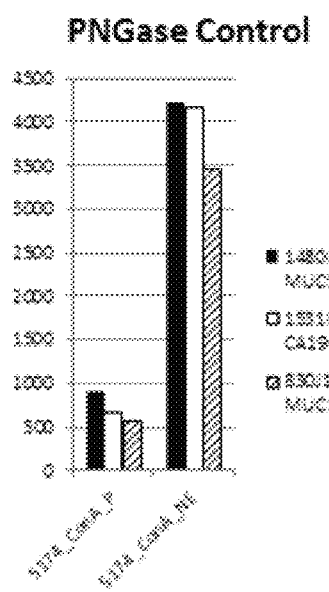
Figure 13E:
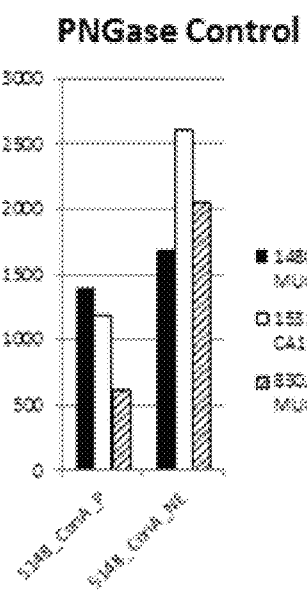
Figure 13F:
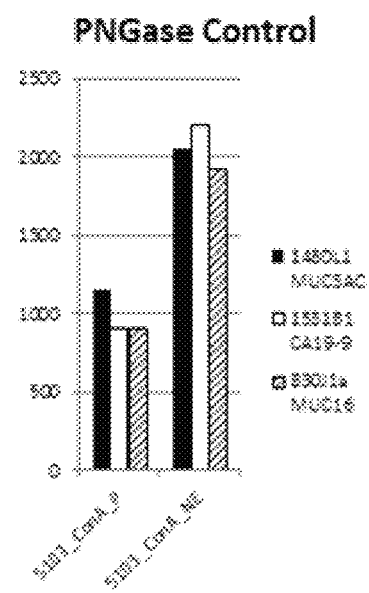

The experimental data shown in FIGS. 13D-13F validate that PNGaseF is active and removes N-linked glycans from all types of serum samples tested: serum from a healthy subject, a cancer patient with low CA19-9, and a cancer patient with high CA19-9. The arrays were pretreated with PNGaseF to remove ConA binding to the capture antibodies; incubated with serum; treated with either PNGaseF or buffer; and detected with ConA. The inventors saw that ConA binding was dramatically reduced with PNGaseF treatment. The PNGase Control graphs validate PNGase activity by showing that N-glycan binding via ConA was reduced with PNGase treatment of captured material (in cancer high, cancer low, and control serum samples).

What is claimed is:

1. A method of diagnosing and treating pancreatic cancer in a subject, said method comprising:
   obtaining or having obtained a biological sample from the human subject, wherein said biological sample includes two or more glycoforms of a Lewis A antigen and wherein the two or more glycoforms of the Lewis A antigen are selected from the group consisting of sialyl-Lewis A:sialyl-Lewis A (sLeA:sLeA), sialyl-Lewis A:type1type2 sialyl-N-acetyl-lactosamine (sLeA:sLacNAc t1t2), sialyl-Lewis A:sulfated Lewis A (sLeA:sulfo-LeA), sialyl-Lewis A:sulfated sialyl-Lewis A (sLeA:sulfo-sLeA), sialyl-Lewis A:sulfated Lewis X (sLeA:sulfo-LeX), and sialyl-Lewis A:sulfated sialyl-Lewis X (sLeA:sulfo-sLeX);
   detecting or having detected a level of the two or more glycoforms of the Lewis A antigen in the biological sample;
   diagnosing the subject with pancreatic cancer when the two or more glycoforms of the Lewis A antigen in the biological sample are elevated as compared to a statistically validated threshold for the two or more glycoforms of the Lewis A antigen; and
   administering a therapeutically effective amount of a treatment for pancreatic cancer to the diagnosed subject,
   wherein the treatment is surgically resecting a pancreatic cystic lesion in the subject, applying radiation to the pancreatic cystic lesion, or administering a chemotherapeutic agent to the subject.

2. The method of claim 1, wherein the diagnosis differentiates pancreatic cancer from a benign pancreatic disease.

3. The method of claim 1, wherein the biological sample further includes one or more glycoforms of MUC5AC;
   wherein the detecting step further comprises detecting or having detected a level of the one or more glycoforms of the MUC5AC in the biological sample;
   wherein the diagnosing step further comprises diagnosing the subject with pancreatic cancer when two or more glycoforms of the Lewis A antigen and the one or more glycoforms of the MUC5AC in the biological sample are at a different level than a statistically validated threshold for the two or more glycoforms of the Lewis A antigen and the one or more glycoforms of the MUC5AC.

4. The method of claim 1, wherein the two or more glycoforms of the Lewis A antigen are sLeA:sLeA and sLeA:sLacNAc t1t2.

5. The method of claim 3, wherein the one or more glycoforms of MUC5AC is selected from the group consisting of MUC5AC:type 1 sialyl-N-acetyl-lactosamine (MUC5AC:sLacNAc t1), MUC5AC:type1type 2 sialyl-N-acetyl-lactosamine (MUC5AC:sLacNAc t1t2), MUC5AC: sialyl-Lewis A (MUC5AC:sLeA), MUC5AC:sialyl-Lewis X (MUC5AC:sLeX), MUC5AC: sulfated-Lewis A (MUC5AC:sulfo-LeA), MUC5AC: sulfated-Lewis X (MUC5AC:sulfo-LeX), MUC5AC:sulfated sialyl-Lewis A (MUC5AC:sulfo-sLeA), and MUC5AC: sulfated sialyl-Lewis X (MUC5AC:sulfo-sLeX).

6. The method of claim 3, wherein the two or more glycoforms of the Lewis A_antigen are sLeA:sLeA and sLeA:sLacNAc t1t2, and wherein the one or more glycoforms of MUC5AC is MUC5AC:sLacNAc t1t2.

7. The method of claim 3, wherein the two or more glycoforms of the Lewis A antigen and the one or more glycoforms of MUC5AC are detected with one or more antibodies or glycan-binding proteins.

8. The method of claim 6, wherein the sLeA:sLeA is detected with a CA19-9 anti-sialyl Lewis A antibody, and wherein the sLeA:sLacNAc t1t2 and the MUC5AC:sLacNAc t1t2 are detected with a TRA-1-60 anti-Lewis antigen antibody.

9. The method of claim 1, wherein the biological sample is blood serum.

10. The method of claim 3, wherein the one or more glycoforms of MUC5AC is MUC5AC: sLacNAc t1t2.

11. A method of providing medical services for a human patient suspected of having or having pancreatic cancer, said method comprising:
    requesting a biological sample from and diagnostic information about the patient, wherein the diagnostic information is a level of two or more glycoforms of a Lewis A antigen in the biological sample and wherein the two or more glycoforms of the Lewis A antigen are selected from the group consisting of sialyl-Lewis A:sialyl-Lewis A (sLeA:sLeA), sialyl-Lewis A:type1type 2 sialyl-N-acetyl-lactosamine (sLeA:sLacNAc t1t2), sialyl-Lewis A:sulfated Lewis A (sLeA:sulfo-LeA), sialyl-Lewis A:sulfated sialyl-Lewis A (sLeA:sulfo-sLeA), sialyl-Lewis A:sulfated Lewis X (sLeA:sulfo-LeX), and sialyl-Lewis A:sulfated sialyl-Lewis X (sLeA:sulfo-sLeX); and
    administering a therapeutically effective amount of a treatment for pancreatic cancer when the diagnostic information indicates that the level of the two or more glycoforms of the Lewis A antigen in the biological sample are at an elevated level as compared to control levels of the two or more glycoforms of the Lewis A antigen,
    wherein the treatment is surgically resecting a pancreatic cystic lesion in the subject, applying radiation to the pancreatic cystic lesion, or administering a chemotherapeutic agent to the subject.

12. The method of claim 11, wherein the diagnostic information differentiates pancreatic cancer from a benign pancreatic disease.

13. The method of claim 11, wherein the biological sample further includes one or more glycoforms of MUC5AC and the diagnostic information further includes a level of one or more glycoforms of MUC5AC
    wherein the administering step further includes administering a therapeutically effective amount of a treatment for pancreatic cancer when the diagnostic information indicates that the level of the two or more glycoforms of the Lewis A antigen and the level of one or more glycoforms of MUC5AC in the biological sample are at an elevated level as compared to the control levels of the two or more glycoforms of the Lewis A antigen and the one or more glycoforms of MUC5AC.

14. The method of claim 13, wherein the two or more glycoforms of the Lewis A antigen are sLeA:sLeA and sLeA:sLacNAc t1t2 and wherein the one or more glycoforms of MUC5AC is MUC5AC: sLacNAc t1t2.

15. The method of claim 14, wherein the level of the sLeA:sLeA is detected with a CA19-9 anti-sialyl Lewis A antibody, and wherein the level of the sLeA:sLacNAc t1t2 and the MUC5AC:sLacNAc t1t2 are detected with a TRA-1-60 anti-Lewis antigen antibody.

16. The method of claim 11, wherein the biological sample is blood serum.

17. The method of claim 13, wherein the one or more glycoforms of MUC5AC is MUC5AC: sLacNAc t1t2.

18. The method of claim 11, wherein the two or more glycoforms of the Lewis A antigen are sLeA:sLeA and sLeA:sLacNAc t1t2.

19. The method of claim 13, wherein the one or more glycoforms of MUC5AC is selected from the group consisting of MUC5AC:type 1 sialyl-N-acetyl-lactosamine (MUC5AC:sLacNAc t1), MUC5AC:type1type 2 sialyl-N-acetyl-lactosamine (MUC5AC: sLacNAc t1t2), MUC5AC: sialyl-Lewis A (MUC5AC:sLeA), MUC5AC:sialyl-Lewis X (MUC5AC:sLeX), MUC5AC:sulfated-Lewis A (MUC5AC: sulfo-LeA), MUC5AC: sulfated-Lewis X (MUC5AC:sulfo-LeX), MUC5AC:sulfated sialyl-Lewis A (MUC5AC:sulfo-sLeA), and MUC5AC:sulfated sialyl-Lewis X (MUC5AC: sulfo-sLeX).

* * * * *